(12) United States Patent
Hammock et al.

(10) Patent No.: US 11,123,311 B2
(45) Date of Patent: Sep. 21, 2021

(54) METHODS OF TREATING MENTAL DISORDERS

(71) Applicant: The Regents of the University of California, Oakland, CA (US)

(72) Inventors: Bruce D. Hammock, Davis, CA (US); Christophe Morisseau, West Sacramento, CA (US); Jun Yang, Davis, CA (US); Kenji Hashimoto, Chiba (JP)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/065,907

(22) PCT Filed: Dec. 15, 2016

(86) PCT No.: PCT/US2016/067024
§ 371 (c)(1),
(2) Date: Jun. 25, 2018

(87) PCT Pub. No.: WO2017/120012
PCT Pub. Date: Jul. 13, 2017

(65) Prior Publication Data
US 2019/0125696 A1 May 2, 2019

Related U.S. Application Data

(60) Provisional application No. 62/275,182, filed on Jan. 5, 2016.

(51) Int. Cl.
| | |
|---|---|
| *A61K 31/137* | (2006.01) |
| *A61K 31/185* | (2006.01) |
| *A61K 31/336* | (2006.01) |
| *A61K 31/135* | (2006.01) |
| *A61K 31/15* | (2006.01) |
| *A61K 31/4525* | (2006.01) |
| *A61P 25/30* | (2006.01) |
| *A61P 25/18* | (2006.01) |
| *A61P 25/24* | (2006.01) |
| *A61K 31/138* | (2006.01) |
| *A61K 31/165* | (2006.01) |
| *A61K 31/343* | (2006.01) |
| *A61K 31/352* | (2006.01) |
| *A61K 31/381* | (2006.01) |
| *A61K 45/06* | (2006.01) |

(52) U.S. Cl.
CPC .......... *A61K 31/137* (2013.01); *A61K 31/135* (2013.01); *A61K 31/138* (2013.01); *A61K 31/15* (2013.01); *A61K 31/165* (2013.01); *A61K 31/185* (2013.01); *A61K 31/336* (2013.01); *A61K 31/343* (2013.01); *A61K 31/352* (2013.01); *A61K 31/381* (2013.01); *A61K 31/4525* (2013.01); *A61P 25/18* (2018.01); *A61P 25/24* (2018.01); *A61P 25/30* (2018.01); *A61K 45/06* (2013.01)

(58) Field of Classification Search
CPC .... A61K 31/137; A61K 31/135; A61K 31/15; A61K 31/4525; A61K 31/138; A61K 31/165; A61K 31/343; A61K 31/352; A61K 31/381; A61K 31/185; A61K 31/336; A61K 45/06; A61P 25/30; A61P 25/18; A61P 25/24
See application file for complete search history.

(56) References Cited

U.S. PATENT DOCUMENTS

| | | | |
|---|---|---|---|
| 2013/0065936 A1* | 3/2013 | Hammock | A61K 31/00 514/424 |
| 2014/0038923 A1* | 2/2014 | Hammock | C07D 231/12 514/158 |

OTHER PUBLICATIONS

Seehusen et al. Second-generation antidepressants for depression in adults. Am Fam Physician. Nov. 15, 2013;88(10):687-9.*
Vickers, JC. A vaccine against Alzheimer's disease: developments to date. Drugs Aging 2002; 19(7):487-94.*
Perrin et al. Multimodal techniques for diagnosis and prognosis of Alzheimer's disease. Nature Oct. 15, 2009;461(7266):916-22, Published online Oct. 14, 2009.*
Hampel et al. The future of Alzheimer's disease: the next 10 years. Prog Neurobiol. Dec. 2011;95(4):718-28. Epub Nov. 22, 2011.*
Steinert et al., "Relapse rates after psychotherapy for depression—stable long-term effects? A meta-analysis", J Affect Disord, 2014, 168:107-118.
Strawbridge et al., "Inflammation and clinical response to treatment in depression: A meta-analysis", Eur Neuropsychopharmacol, 2015, 25(10):1532-1543.
Torrey et al., "The Stanley Foundation brain collection and Neuropathology consortium", Schizophr Res, 2000, 44(2):151-155.

(Continued)

*Primary Examiner* — Gregory S Emch
(74) *Attorney, Agent, or Firm* — Mintz Levin Cohn Ferris Glovsky & Popeo, P.C.

(57) ABSTRACT

This invention provides methods for preventing, mitigating, ameliorating and/or controlling psychiatric disorders, including depression, major depression, bipolar disorder, schizophrenia and substance abuse (including addiction and dependence) by administration of an agent that increases epoxy-fatty acids (e.g., an inhibitor of soluble epoxide hydrolase), as sole active agent or in combination with another agent (e.g., an antidepressant, an antipsychotic, an anxiolytic). When co-administered in combination with another agent, one or both agent may be administered at a subtherapeutic dose.

16 Claims, 21 Drawing Sheets
Specification includes a Sequence Listing.

(56) References Cited

OTHER PUBLICATIONS

Wagner et al., "The Role of Long Chain Fatty Acids and Their Epoxide Metabolites in Nociceptive Signaling", Prostaglandins Other Lipid Mediat, 2014, 113-115:2-12.

World Health Organization (WHO) Depression (2012) Fact sheet No. 369/Oct. 2012. Available at http://www.who.int/mediacentre/factsheets/fs369/en/index.html.

Yang et al., Peripheral interleukin-6 promotes resilience versus susceptibility to inescapable electric stress. Acta Neuropsychiatr, 2015, 27(5):312-316.

Yang et al., "Quantitative Profiling Method for Oxylipin Metabolome by Liquid Chromatography ElectrosprayIonization Tandem Mass Spectrometry", Anal Chem, 2009, 81(19):8085-8093.

Yang et al., "Peripheral IL-6 signaling: a promising therapeutic target for depression?", Expert Opin Investig Drugs, 2015, 24(7):989-990.

Yang et al., "Regional differences in brain-derived neurotrophic factor levels and dendritic spine density confer resilience to inescapable stress", Int J Neuropsychopharmacol, 2015, pp. 1-6.

Yang et al., "R-ketamine: a rapid-onset and sustained antidepressant without psychotomimetic side effects", Transl Psychiatry, 2015, 5.

Young et al., "A review of the relationship between pro-inflammatory cytokines and major depressive disorder", J Affect Disord, 2014, 169:15-20.

Yuan et al., "14,15-epoxyeicosatrienoic acid promotes production of BDNF from astrocytes and exerts neuroprotective effects during ischemic injury", Neuropathol Appl Neurobiol, 2016, 42:607-620.

Zhang et al., "Comparison of ketamine, 7,8-dihydroxyflavone, and ANA-12 antidepressant effects in the social defeat stress model of depression", Psychopharmacology (Berl), 2015, 232(23):4325-4335.

Zhao et al., "Effects of chronic social defeat stress on behavior and choline acetyltransferase, 78-kDa glucose-regulated protein, and CCAAT/enhancer-binding protein (C/EBP) homologous protein in adult mice", Psychopharmacology (Berl), 2013, 228(2):217-230.

Harris et al., "Soluble epoxide hydrolase: Gene structure,expression and deletion", Gene, Sep. 10, 2013, 526(2):61-74.

Abdu et al, (2011) "Epoxyeicosatrienoic acids enhance axonal growth in primary sensory and cortical neuronal cell cultures," J Neurochem , May 2011, 117(4): 632-642.

Berton et al, "Essential role of BDNF in the mesolimbic dopamine pathway in social defeat stress", 2006, Science 311(5762):864-868.

Biesheuvel-Leliefeld et al., "Effectiveness of psychological interventions in preventing recurrence of depressive disorder: meta-analysis and meta-regression", Journal of Affective Disorders, 2015, 174:400-410.

Bjorkholm et al., BDNF—a key transducer of antidepressant effects, Neuropharmacology Oct. 28, 2015. doi:10.1016/j.neuropharm.

Borhan et al., "Improved radiolabeled substrates for soluble epoxide hydrolase", Anal Biochem, 1995, 231: 188-200.

Dantzer et al., "From inflammation to sickness and depression: when the immune system subjugates the brain", Nature Rev Neurosci, 2008, 9(1):46-57.

Dargel et al., "C-reactive protein alterations in bipolar disorder: a meta-analysis", J Clin Psychiatry, Feb. 2015, 76(2):142-150.

Dean et al., "Regionally-specific changes in levels of tumour necrosis factor in the dorsolateral prefrontal cortex obtained postmortem from subjects with major depressive disorder", Journal of Affective Disorders, 2010, 120 (1-3):245-248.

Dowlati et al., "A meta-analysis of cytokines in major depression", Biol Psychiatry, 2010, 67:446-457.

Duman et al., "A neutrotrophic model for stress-related mood disorders", Biol Psychiatry, 2006, 59(12):1116-1127.

Fernandes et al., "C-reactive protein is increased in schizophrenia but is not altered by antipsychotics: meta-analysis and implications", Molecular Psychiatry, 2016, 21, 554-564.

Forte et al., "Long-term morbidity in bipolar-I, bipolar-II, and unipolar major depressive disorders", Journal of Affective Disorders, 2015, 178:71-78.

Gold, PW, "The organization of the stress system and its dysregulation in depressive illness", Molecular Psychiatry, 2015, 20:32-47.

Golden et al., "A standard protocol for repeated social defeat stress in mice", Nat Protoc, 2011 6(8):1183-1191.

Guidi et al., "The sequential integration of pharmacotherapy and psychotherapy in the treatment of major depressive disorder. A meta-analysis of the sequential model and a critical review of the literature", American Journal of Psychiatry, Oct. 20, 2015, 2015; https://doi.org/10.1176/appi.ajp.2015.15040476.

Haapakoski et al., "Cumulative meta-analysis of interleukins 6 and 1β, tumour necrosis factor α and C-reactive protein in patients with major depressive disorder", Brain Behavior Immunity, Oct. 2015, 49:206-215.

Hashimoto, Kenji, "Brain-derived neurotrophic factor as a biomarker for mood disorders: an historical overview and future directions", Psychiatry and Clinical Neurosciences, 2010, 64(4):341-357.

Hashimoto, Kenji, "Inflammatory biomarkers as differential predictors of antidepressant response", International Journal of Molecular Sciences, 2015, 16:7796-7801.

Hashimoto, Kenji, "Sigma-1 receptor chaperone and brain-derived neurotrophic factor: emerging links between cardiovascular disease and depression", Progress in Neurobiology, 2013, 100:15-29.

Hashimoto et al., "Critical role of brain-derived neurotrophic factor in mood disorders", Brain Research Reviews, F2004, Rev 45:104-114.

Hashimoto, et al., "A novel target of action of minocycline in NFG-induced neurite outgrowth in PC12 cells: translation initiation factor eIF4AI", PLoS One, 2010, 5(11):e15430.

Hodes et al., "Individual differences in the peripheral immune system promote resilience versus susceptibility to social stress", Proc Natl Acad Sci USA, Nov. 11, 2014, 111(45):16136-16141.

Imig et al., "Soluble epoxide hydrolase as a therapeutic target for cardiovascular diseases", Nat Rev Drug Discov, Oct. 2009, 8(10):794-805.

Inceoglu et al., "Epoxy fatty acids and inhibition of the soluble epoxide hydrolase selectively modulate GABA mediated neurotransmission to delay onset of seizures", PLoS One, 2013, 8(12):e80922.

Ishima et al., "Potentiation of nerve growth factor-induced neurite outgrowth in PC12 cells by ifenprodil: the role of sigma-1 and IP3 receptors", PLoS One, 2012, 7(5):e37989.

Kitamura et al., "Potent natural soluble epoxide hydrolase inhibitors from Pentadiplandra brazzeana baillon: synthesis, quantification, and measurement of biological activities in vitro and in vivo", PloS One, Feb. 6, 2015, 10(2):1-16.

Kohler et al., "Effect of anti-inflammatory treatment on depression, depressive symptoms, and adverse effects: a systematic review and meta-analysis of randomized clinical trials", JAMA Psychiatry, 2014, 71(12):1381-1391.

Krishnan et al., "Linking molecules to mood: new insight into the biology of depression", Am J Psychiatry, Nov. 2010, 167(11):1305-1320.

Krystal et al., "Rapid-acting glutamatergic antidepressants: the path to ketamine and beyond", Biol Psychiatry, Jun. 15, 2013, 73(12):1133-1141.

Liu et al., "Substituted phenyl groups improve the pharmacokinetic profile and anti-inflammatory effect of urea-based soluble epoxide hydrolase inhibitors in murine models", Eur J Pharm Sci , Mar. 12, 2013, 48(4-5):619-627.

Lopez-Vicario et al., "Inhibition of soluble epoxide hydrolase modulates inflammation and autophagy in obese adipose tissue and liver: role for omega-3 epoxides", Proc Natl Acad Sci, Jan. 13, 2015, 112(2):536-541.

Miller et al., "Inflammation and its discontents: The role of cytokines in the pathophysiology of major depression", Biol Psychiatry, May 1, 2009, 65(9):732-741.

Monteggia et al., "Antidepressant actions of ketamine: from molecular mechanisms to clinical practice", Curr Opin Neurobiol, Feb. 2015, 30:139-143.

Morisseau et al., "Epoxide hydrolases: mechanisms, inhibitor designs, and biological roles", Annu Rev Pharmacol Toxico, 2005, 45:311-333.

(56) References Cited

OTHER PUBLICATIONS

Morisseau et al., "Impact of soluble epoxide hydrolase and epoxyeicosanoids on human health", Annu Rev Pharmacol Toxicol, 2013, 53:37-58.
Munkholm et al., Cytokines in bipolar disorder vs. healthy control subjects: a systematic review and meta-analysis. Journal of Psychiatric Research, 2013, 47:1119-1133.
Na et al., "Efficacy of adjunctive celecoxib treatment for patients with major depressive disorder: a meta-analysis", Progress in Neuropsychopharmacology & Biological Psychiatry, 2014, 48:79-85.
Nestler et al., "Neurobiology of depression.", Neuron, Mar. 28, 2002, 34(1):13-25.
Newport et al., "Ketamine and other NMDA antagonusts: early clinical trials and possible mechanisms in depression", The American Journal of Psychiatry, Oct. 1, 2015, 172(10):950-956; https://doi.org/10.1176/appi.ajp.2015.15040465.
Ostermann et al., "Oral treatment of rodents with soluble epoxide hydrolase inhibitor 1-trifluoromethoxyphenyl-3-(1-propionylpiperidin-4-yl)rea (TPPU): bioavailability, resulting drug levels and modulation of oxylipin pattern", Prostaglandins Other Lipid Mediat , Sep. 2015, 121(0 0):131-137; DOI: 10.1016/j.prostaglandins.2015.06.005.
Potvin et al., "Inflammatory cytokine alterations in schizophrenia: a systematic quantitative review", Biol Psychiatry, 2008, 63:801-808.
Raison et al., "Inflammation, sanitation, and consternation: loss of contact with coevolved, tolerogenic microorganisms and the pathophysiology and treatment of major depression", Arch Gen Psychiatry, Dec. 2010, 67(12):1211-1224.
Ren et al., "BDNF-TrkB signaling in the nucleus accumbens shell of mice has key role in methamphetamine withdrawal symptoms", Transl Psychiatry, 2015, 5:e666.
Rose et al., "1-Aryl-3-(1-acylpiperidin-4-yl)urea inhibitors of human and murine soluble epoxide hydrolase: structure-activity relationships, pharmacokinetics, and reduction of inflammatory pain", J Med Chem, Oct. 14, 2010, 53(19):7067-7075.
Shelton et al., "Altered expression of genes involved in inflammation and apoptosis in frontal cortex in major depression", Mol Psychiatry, Jul. 2011, 16(7):751-762.
Shih et al., "Dysregulation of soluble epoxide hydrolase and lipidomic profiles in anorexia nervosa", Mol Psychiatry Apr. 2016,21(4):537-546; doi: 10.1038/mp.2015.26.
Shirayama et al., "Alterations in brain-derived neurotrophic factor (BDNF) and its precursor proBDNF in the brain regions of a learned helplessness rat model and the antidepressant effects of a TrkB agonist and antagonis", European Neuropsychopharmacology, 2015, 25:2449-2458; doi: 10.1016/j.euroneuro.2015.09.002.
Sim et al., "Prevention of relapse and recurrence in adults with major depressive disorder: systematic review and meta-analyses of controlled trials", International Journal of Neuropsychopharmacology, 2015,pp. 1-13; doi:10.1093/fjnp/pyv076.
Sinai et al., "Targeted disruption of soluble epoxide hydrolase reveals a role in blood pressure regulation", The Journal of Biological Chemistry, Dec. 22, 2000, 275(51):40504-40510.
Sirish et al., "Unique mechanistic insights into the beneficial effects of soluble epoxide hydrolase inhibitors in the prevention of cardiac fibrosis", Proc Natl Acad Sci, Apr. 2, 2013, 110(14):5618-5623.
Ahmed et al., Comparative Efficacy of Haloperidol and Risperidone: A Review, Pakistan Journal of Pharmacology, Jul. 2007, vol. 24, No. 2, pp. 55-64.
Boldrini et al., Benzodiazepines and the Potential Trophic Effect of Antidepressants on Dentate Gyrus Cells in Mood Disorders, International Journal of Neuropsychopharmacology, Dec. 2014, vol. 17, No. 12, pp. 1923-1933.
Cremers et al., Augmentation of SSRI Effects on Serotonin by 5-HT2C Antagonists: Mechanistic Studies, Neuropsychopharmacology, 2007, vol. 32, pp. 1550-1557.
Klein et al., Therapy of Treatment Resistant Depression: focus on the Management of TRD with Atypicalantipsychotics, CNS Spectrums, 2004, vol. 24, No. 2, No. 11, pp. 823-832.
Lourenco et al, Desvenlafaxine in the treatment of major depressive disorder, Neuropsychiatric disease and Treatment, 2009, vol. 5, pp. 127-136.
Parra et al., Effects of co-administration of amitriptyline and fluoxetine on inhibitory avoidance in mice, Behavioural Brain Research, 2010, vol. 214, pp. 343-348.
Sajatovic et al., Adjunct extended-release valproate semisodium in late life schizophrenia, International Journal of Geriatric Psychiatry, 2008, vol. 23, pp. 142-147, abstract.
Thomas et al., Combination Therapy with Monoamine Oxidase Inhibitors and Other Antidepressants or Stimulants: Strategies for the Management of Treatment-Resistant Depression, Pharmacotherapy, 2015, vol. 25, No. 4, pp. 433-449, abstract.
International Search Report for PCT/US2016/067024 dated Mar. 27, 2017, 5 pages.
Written Opinion of the International Searching Authority for PCT/US2016/067024 dated Mar. 27, 2017, 10 pages.

\* cited by examiner

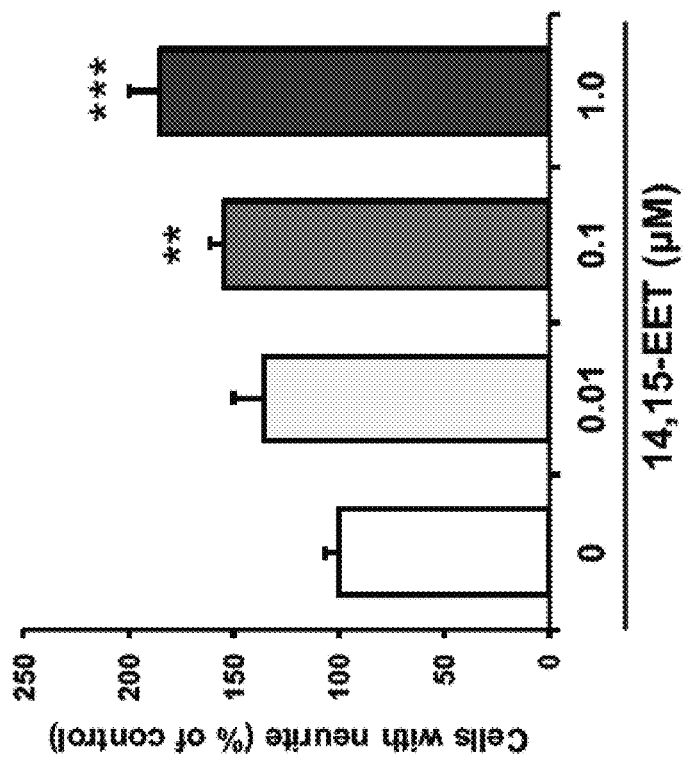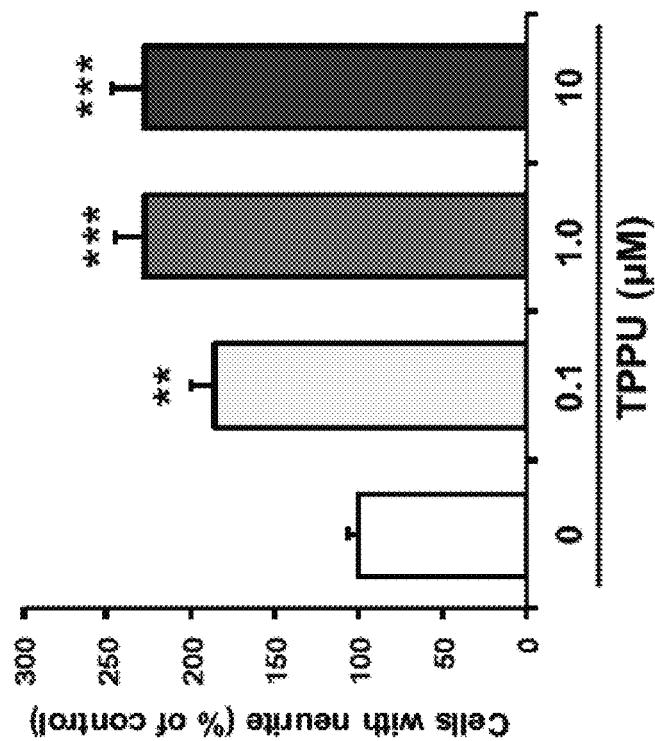
Fig. 1B

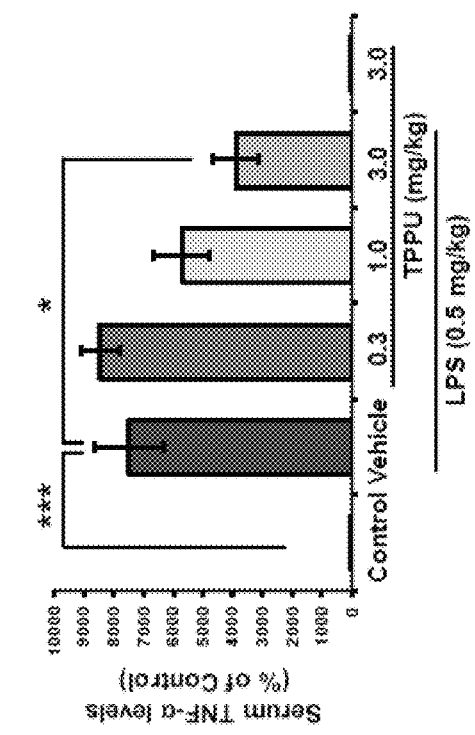
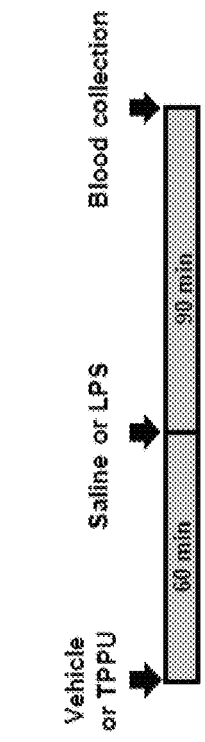
Fig. 2A-B

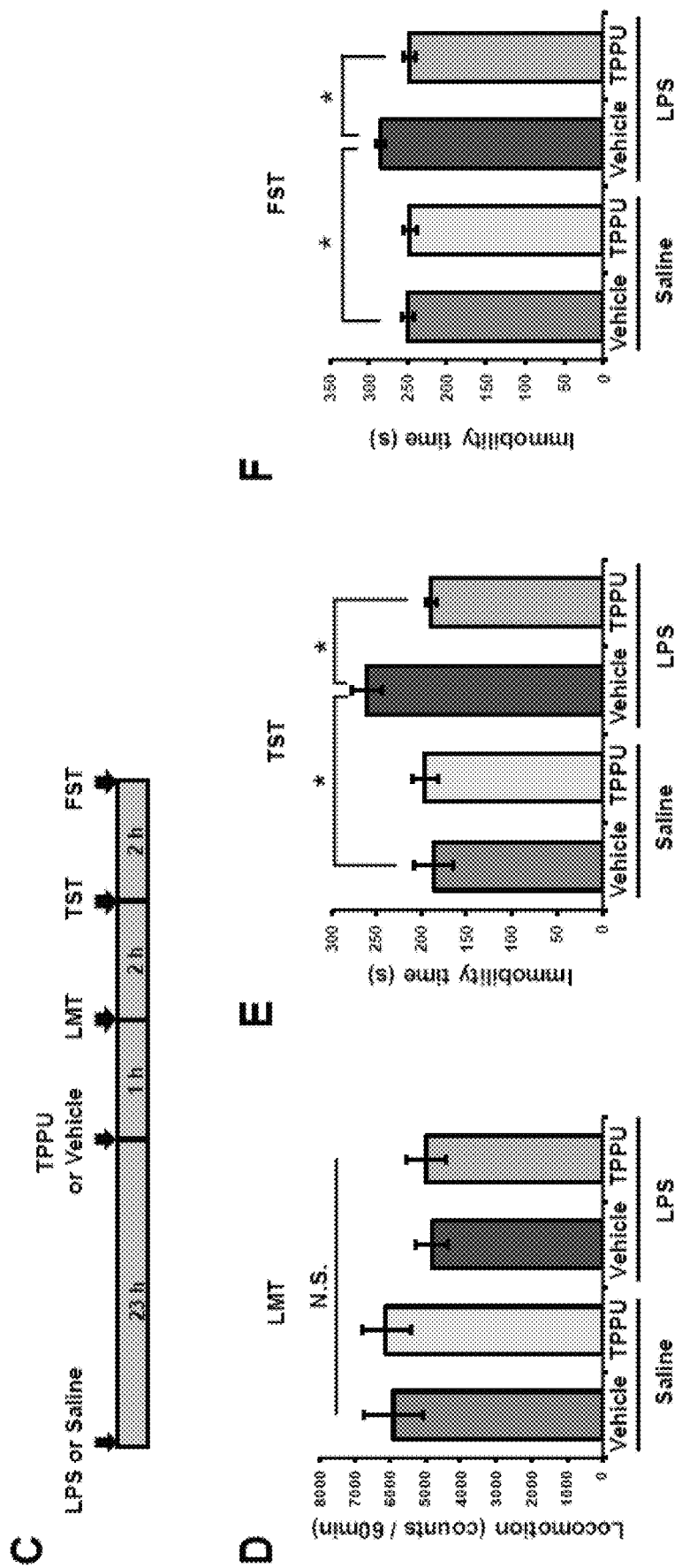
Fig. 2C-F

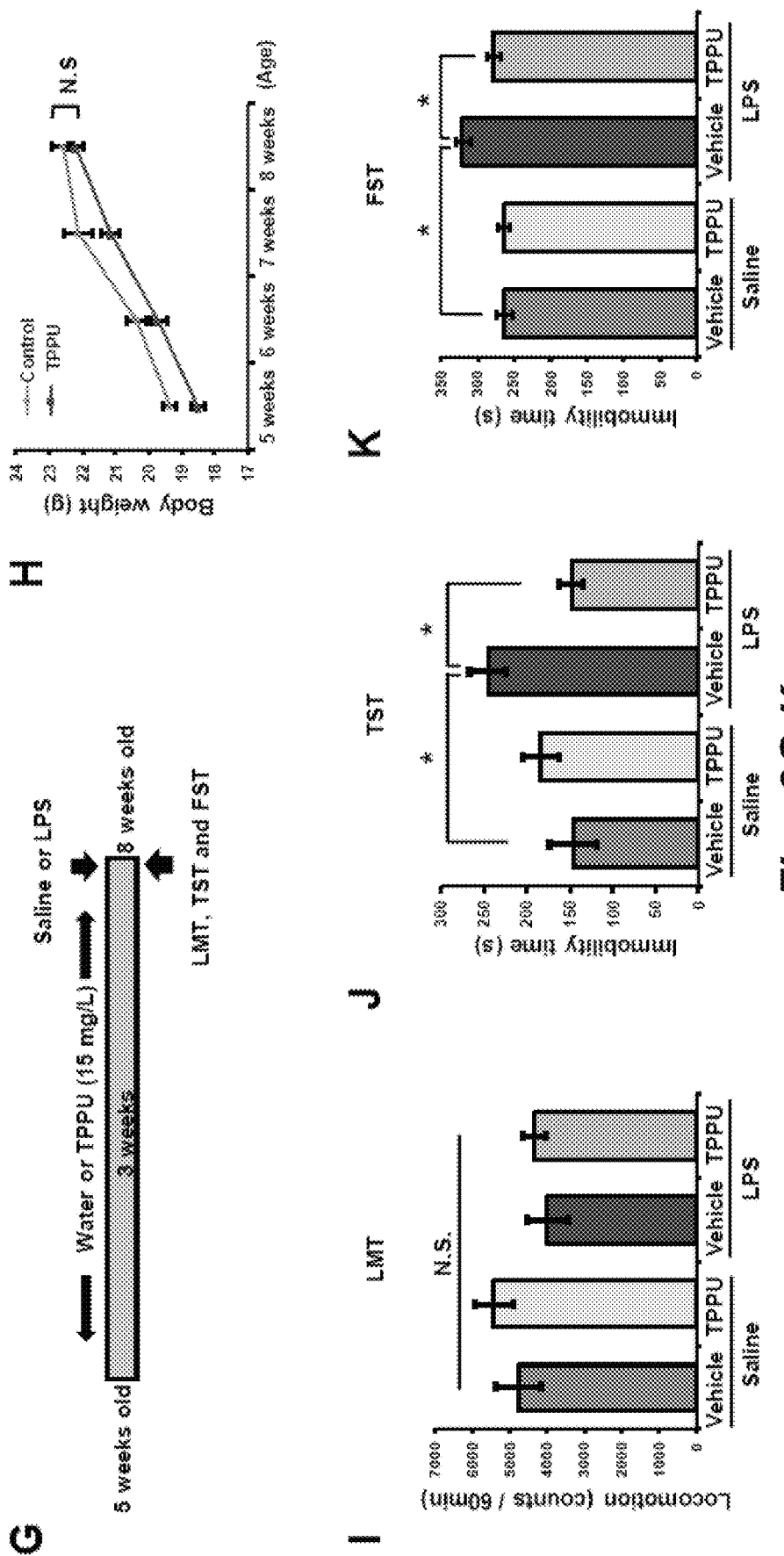
Fig. 2G-K

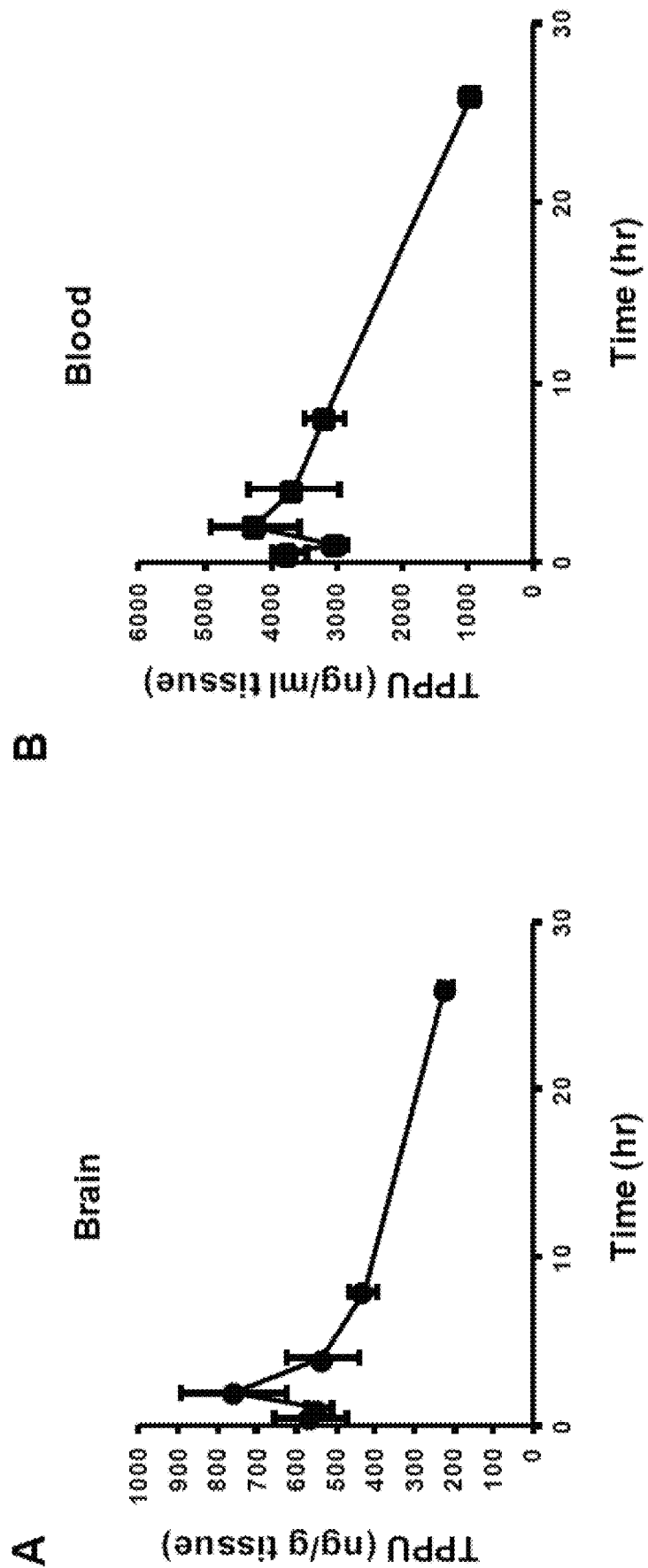
Fig. 3A-B

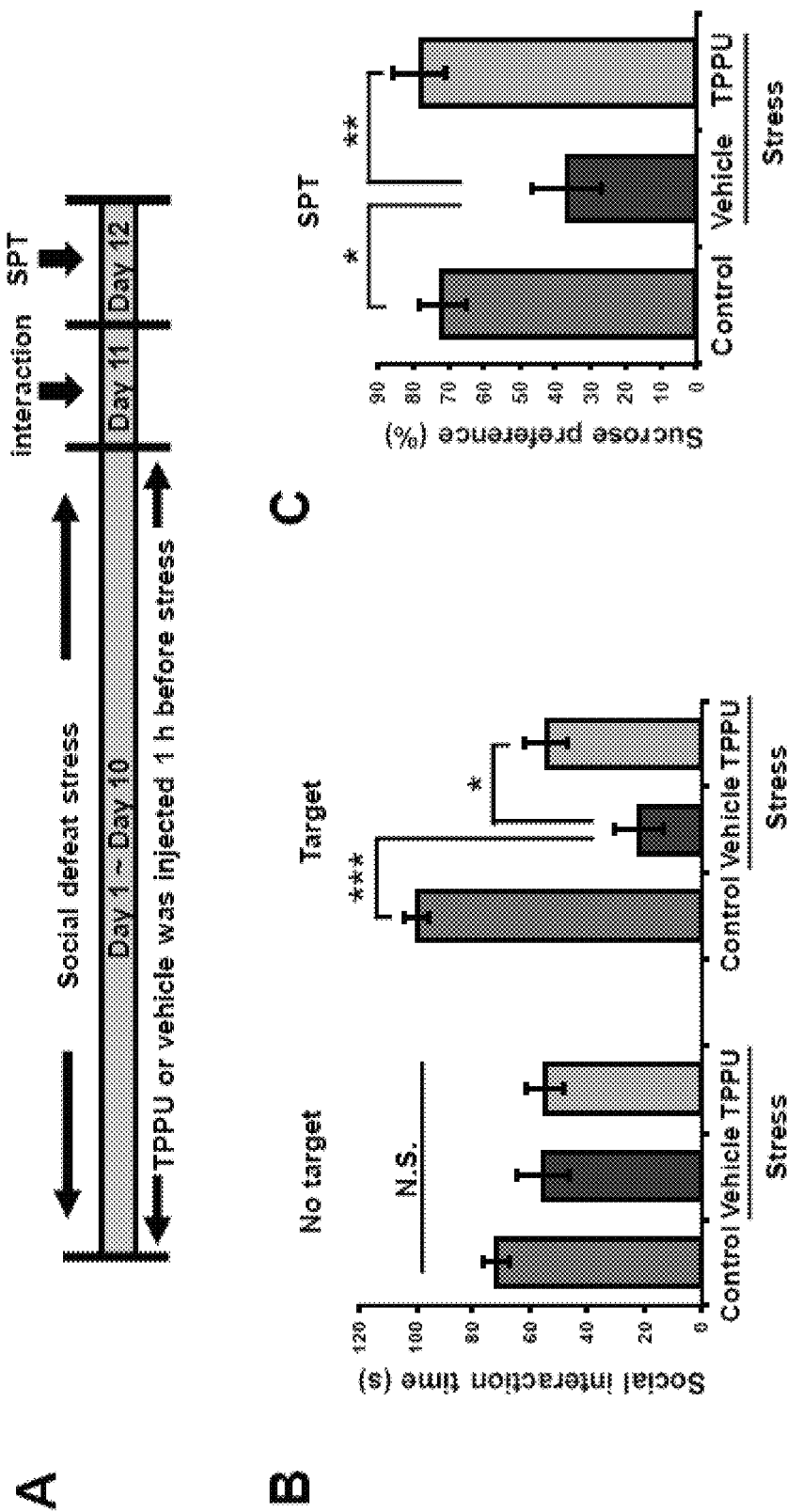
Fig. 4A-C

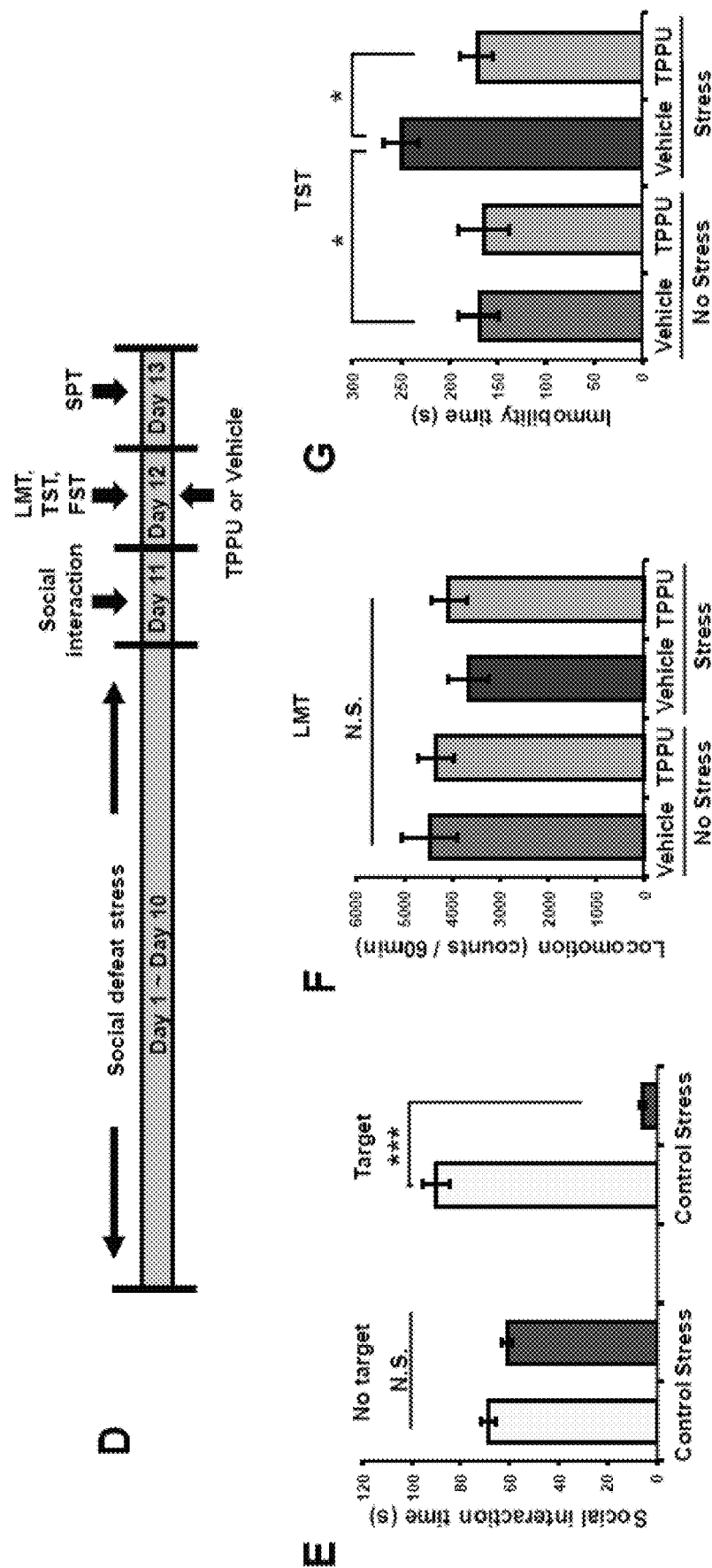
Fig. 4D-G

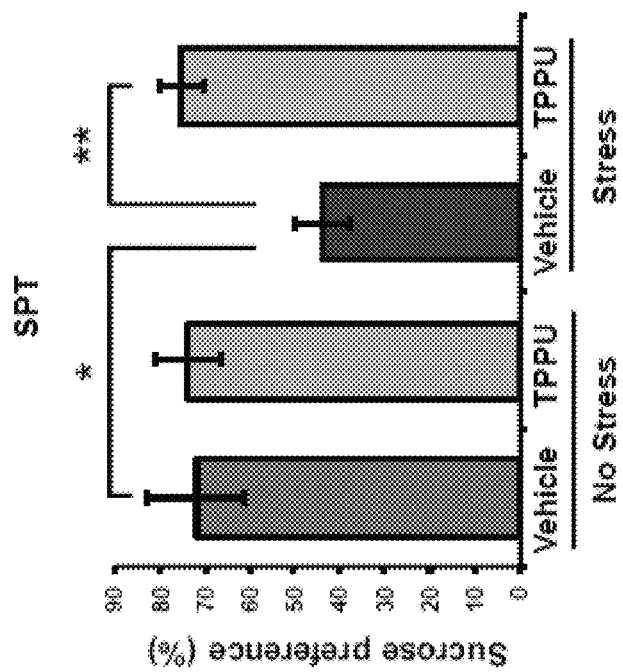
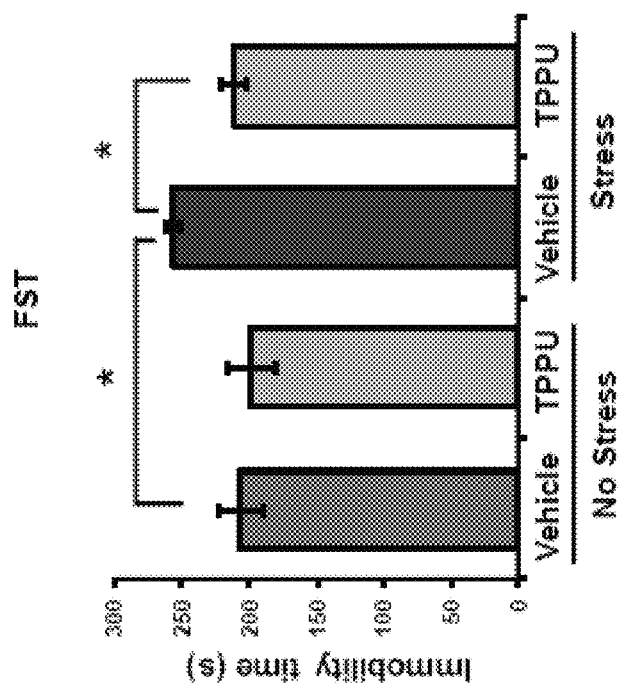
Fig. 4H-I

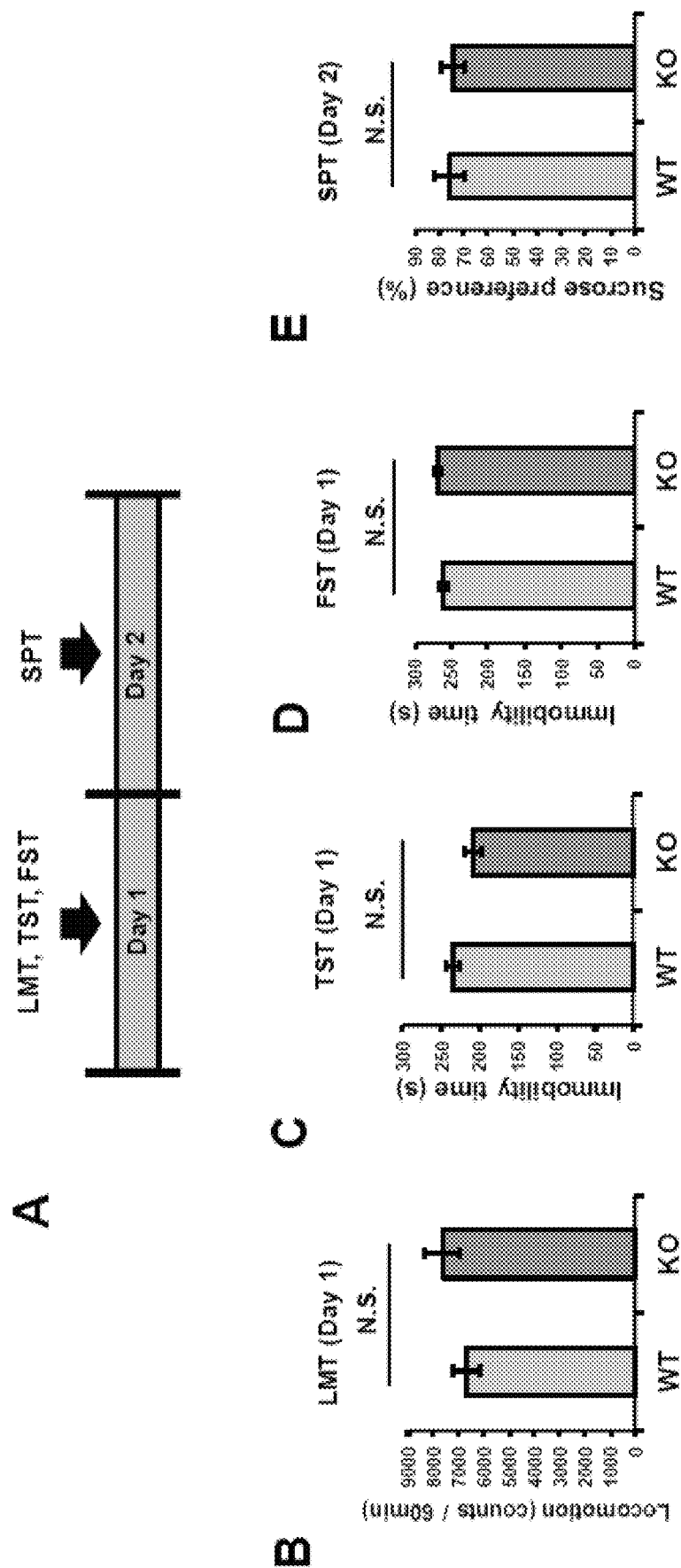
Fig. 5A-E

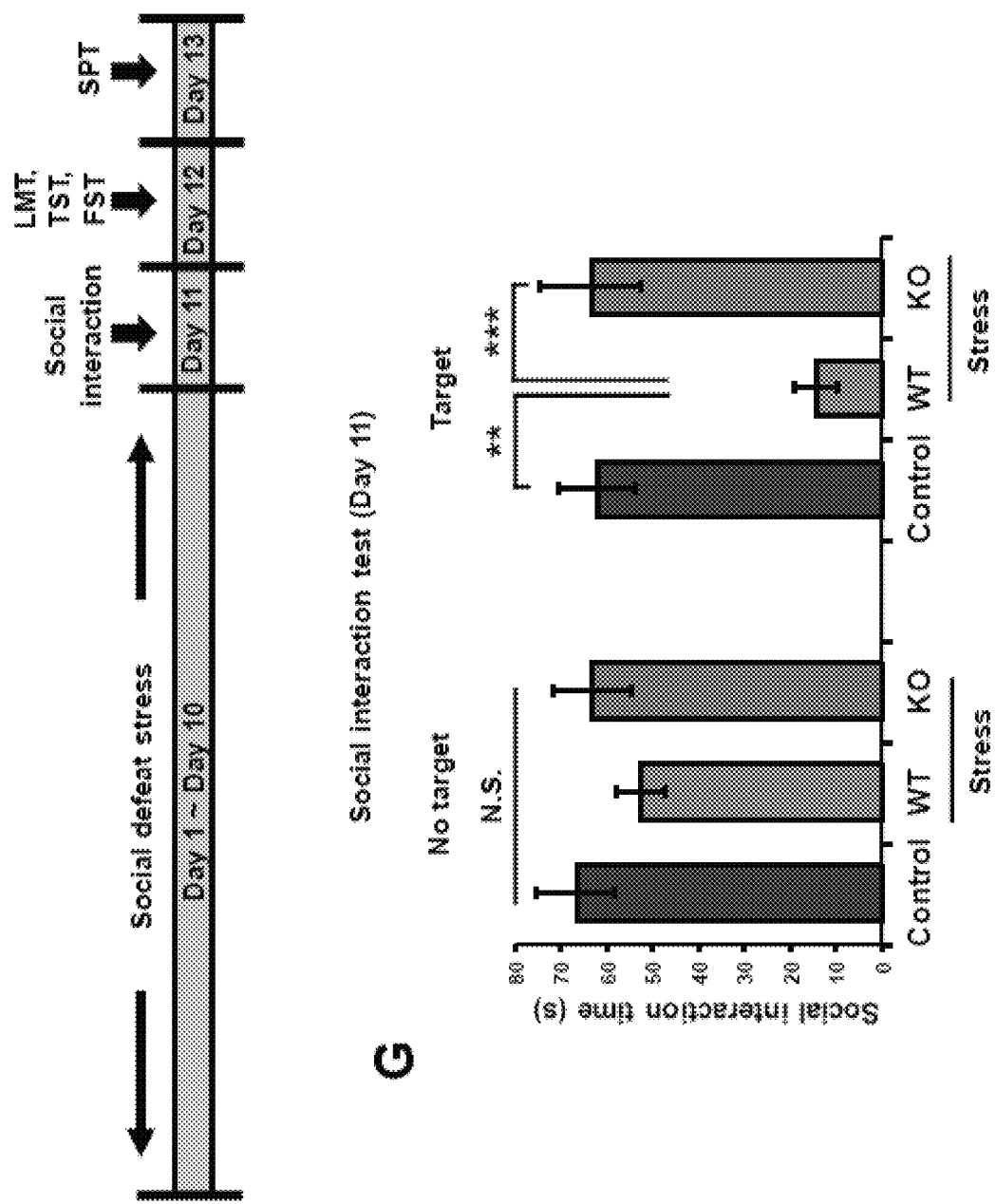
Fig. 5F-G

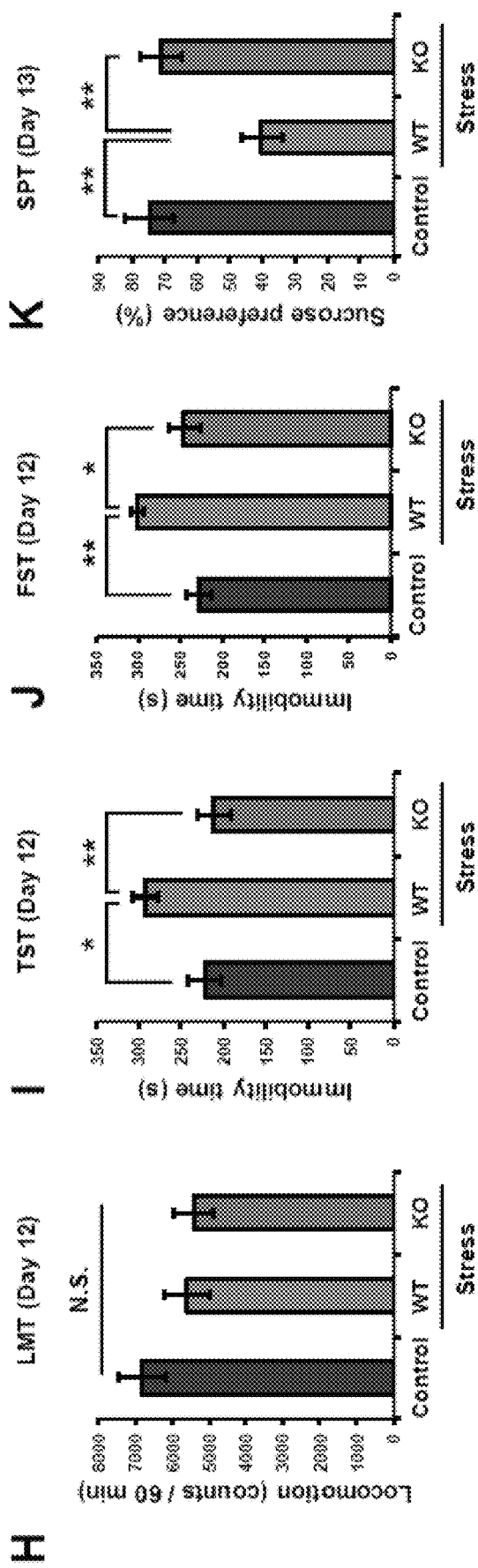
*Fig. 5H-K*

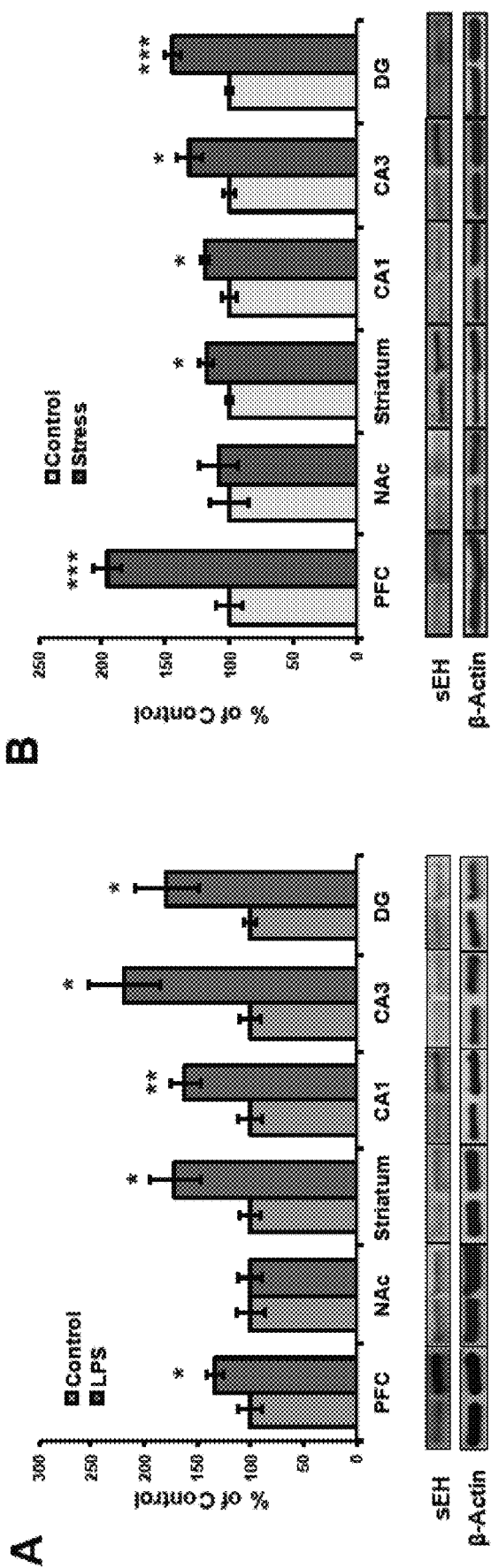
Fig. 6A-B

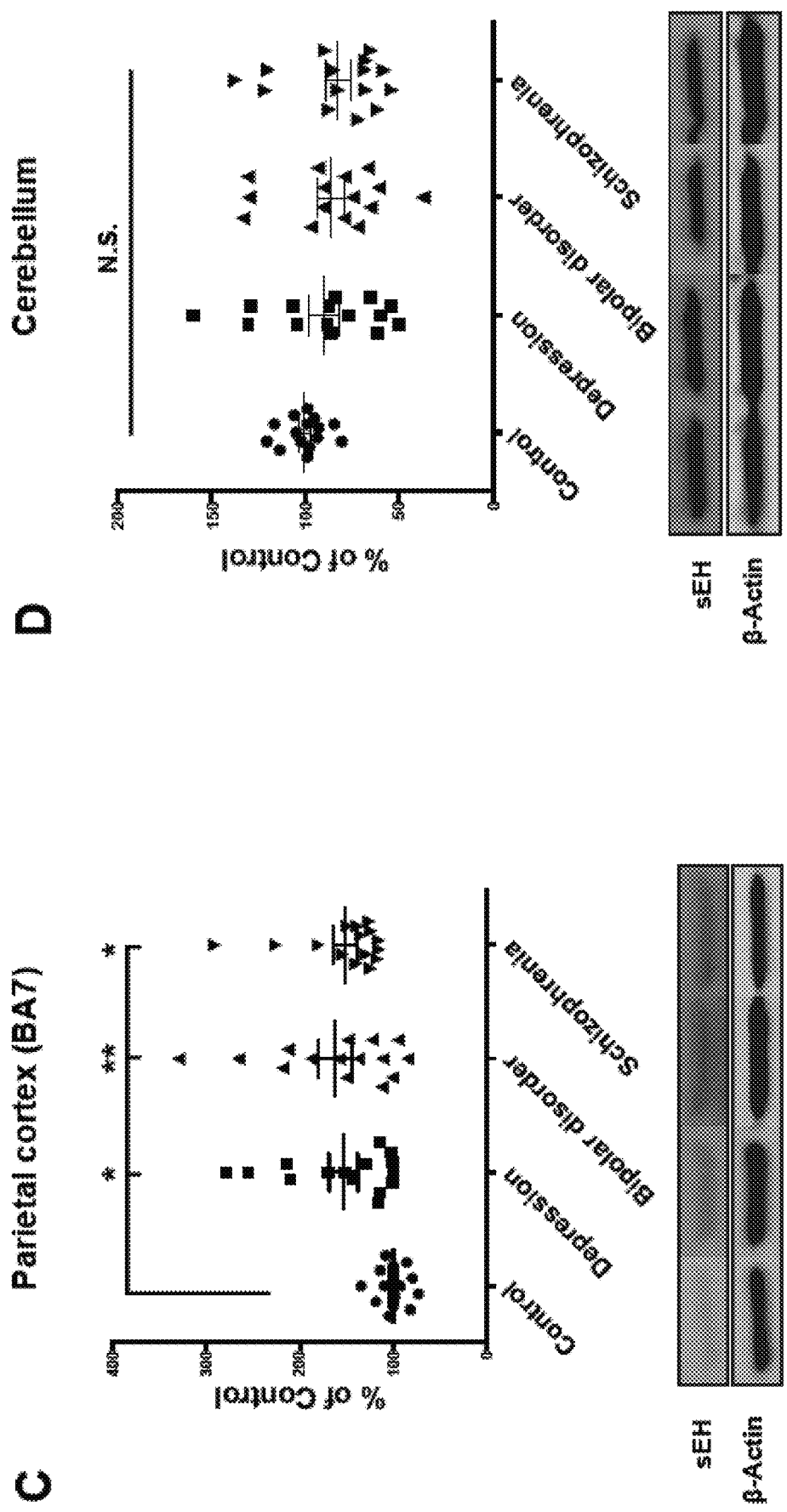
Fig. 6C-D

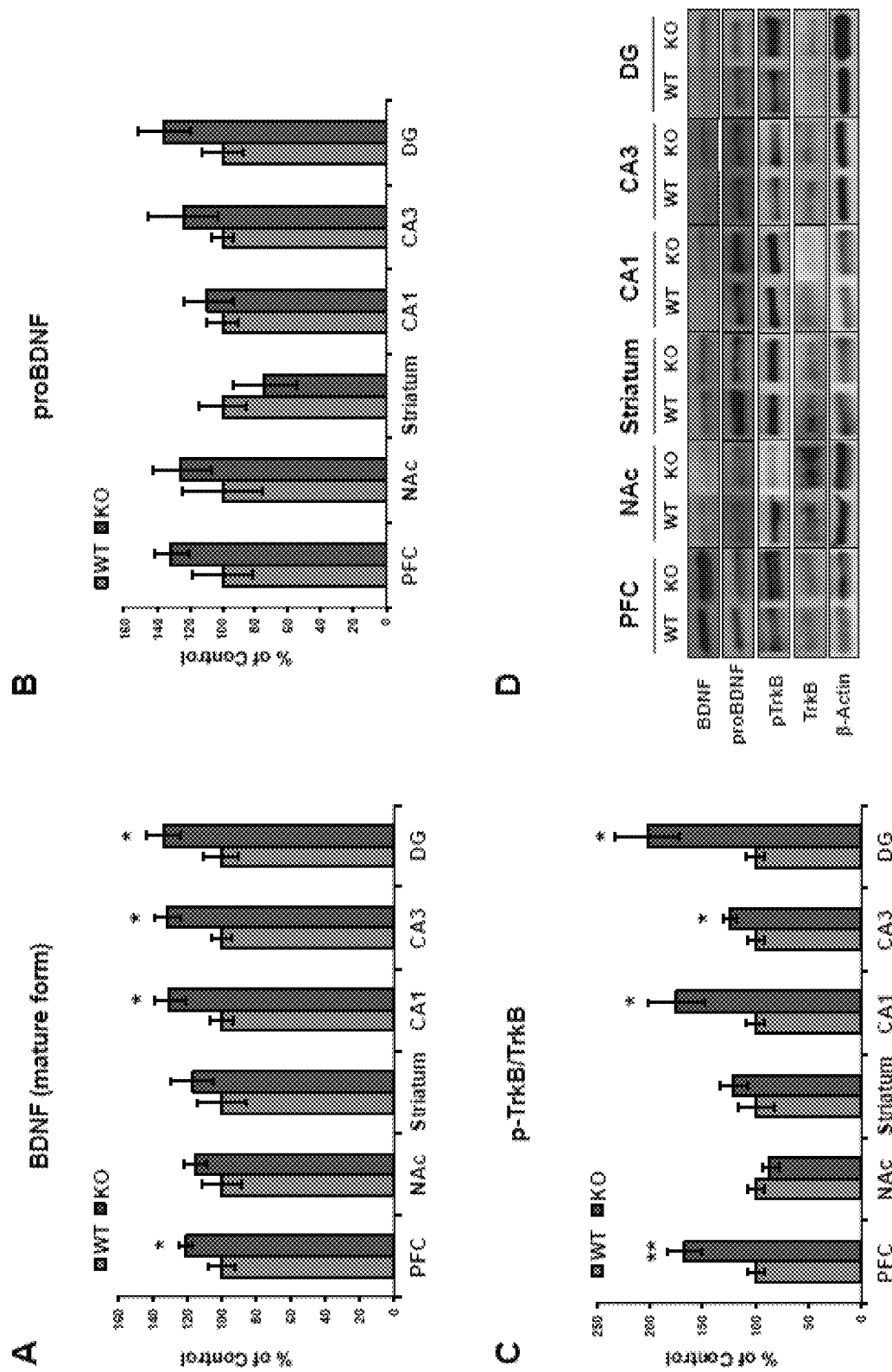
Fig. 8A-D

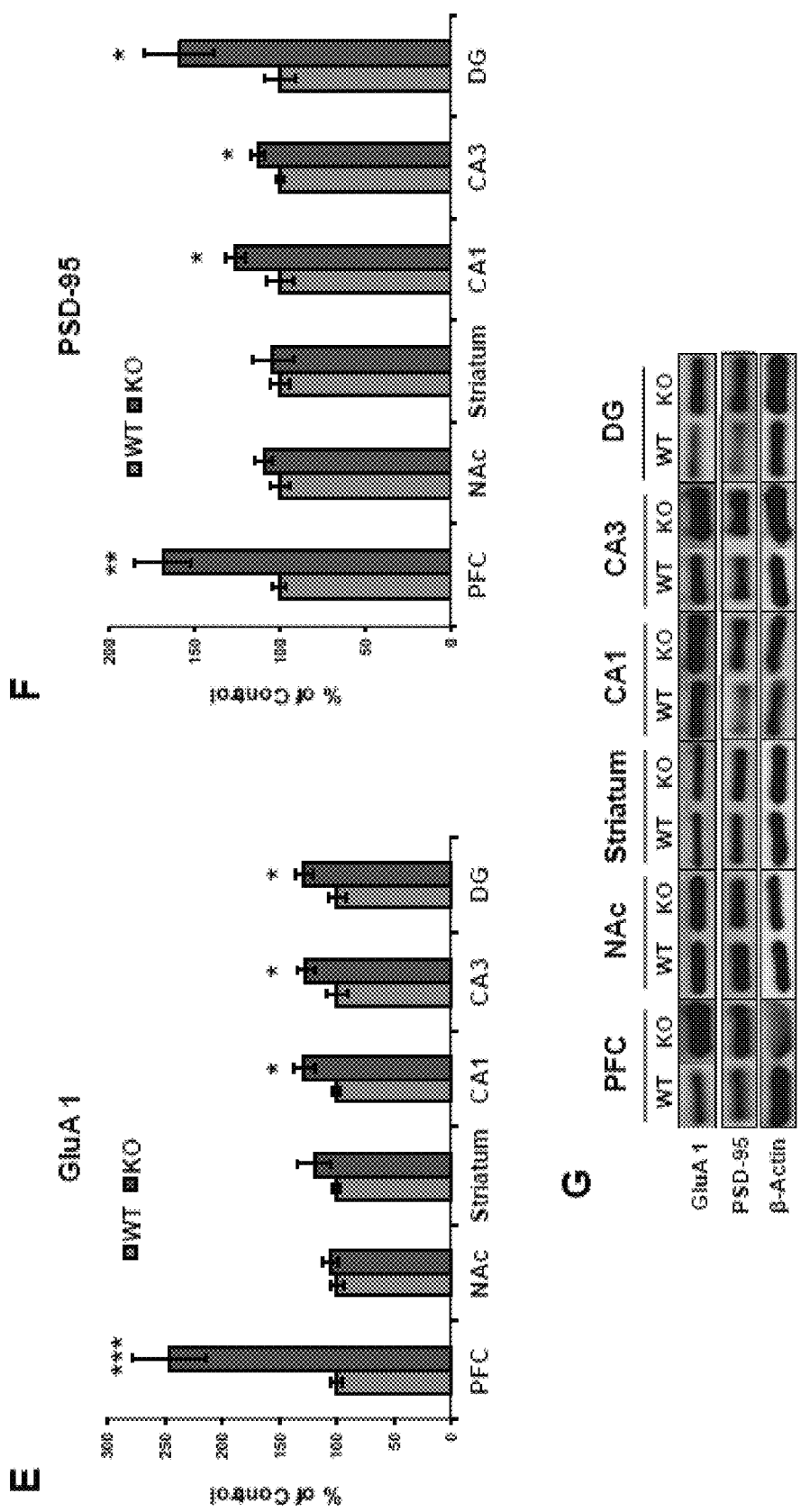
Fig. 8E-G

SEQUENCE LISTING

```
<160> NUMBER OF SEQ ID NOS: 38

<210> SEQ ID NO 1
<211> LENGTH: 555
<212> TYPE: PRT
<213> ORGANISM: Homo sapiens

<400> SEQUENCE: 1
```

-continued

```
Met Thr Leu Arg Ala Ala Val Phe Asp Leu Asp Gly Val Leu Ala Leu
1               5                   10                  15
Pro Ala Val Phe Gly Val Leu Gly Arg Thr Glu Glu Ala Leu Ala Leu
            20                  25                  30
Pro Arg Gly Leu Leu Asn Asp Ala Phe Gln Lys Gly Gly Pro Glu Gly
        35                  40                  45
Ala Thr Thr Arg Leu Met Lys Gly Glu Ile Thr Leu Ser Gln Trp Ile
    50                  55                  60
Pro Leu Met Glu Glu Asn Cys Arg Lys Cys Ser Glu Thr Ala Lys Val
65                  70                  75                  80
Cys Leu Pro Lys Asn Phe Ser Ile Lys Glu Ile Phe Asp Lys Ala Ile
                85                  90                  95
Ser Ala Arg Lys Ile Asn Arg Pro Met Leu Gln Ala Ala Leu Met Leu
                100                 105                 110
Arg Lys Lys Gly Phe Thr Thr Ala Ile Leu Thr Asn Thr Trp Leu Asp
            115                 120                 125
Asp Arg Ala Glu Arg Asp Gly Leu Ala Gln Leu Met Cys Glu Leu Lys
        130                 135                 140
Met His Phe Asp Phe Leu Ile Glu Ser Cys Gln Val Gly Met Val Lys
145                 150                 155                 160
Pro Glu Pro Gln Ile Tyr Lys Phe Leu Leu Asp Thr Leu Lys Ala Ser
                165                 170                 175
Pro Ser Glu Val Val Phe Leu Asp Asp Ile Gly Ala Asn Leu Lys Pro
                180                 185                 190
Ala Arg Asp Leu Gly Met Val Thr Ile Leu Val Gln Asp Thr Asp Thr
            195                 200                 205
Ala Leu Lys Glu Leu Glu Lys Val Thr Gly Ile Gln Leu Leu Asn Thr
        210                 215                 220
Pro Ala Pro Leu Pro Thr Ser Cys Asn Pro Ser Asp Met Ser His Gly
225                 230                 235                 240
Tyr Val Thr Val Lys Pro Arg Val Arg Leu His Phe Val Glu Leu Gly
                245                 250                 255
Ser Gly Pro Ala Val Cys Leu Cys His Gly Phe Pro Glu Ser Trp Tyr
            260                 265                 270
Ser Trp Arg Tyr Gln Ile Pro Ala Leu Ala Gln Ala Gly Tyr Arg Val
        275                 280                 285
Leu Ala Met Asp Met Lys Gly Tyr Gly Glu Ser Ser Ala Pro Pro Glu
        290                 295                 300
Ile Glu Glu Tyr Cys Met Glu Val Leu Cys Lys Glu Met Val Thr Phe
305                 310                 315                 320
Leu Asp Lys Leu Gly Leu Ser Gln Ala Val Phe Ile Gly His Asp Trp
            325                 330                 335
Gly Gly Met Leu Val Trp Tyr Met Ala Leu Phe Tyr Pro Glu Arg Val
            340                 345                 350
Arg Ala Val Ala Ser Leu Asn Thr Pro Phe Ile Pro Ala Asn Pro Asn
        355                 360                 365
Met Ser Pro Leu Glu Ser Ile Lys Ala Asn Pro Val Phe Asp Tyr Gln
    370                 375                 380
Leu Tyr Phe Gln Glu Pro Gly Val Ala Glu Ala Glu Leu Glu Gln Asn
385                 390                 395                 400
Leu Ser Arg Thr Phe Lys Ser Leu Phe Arg Ala Ser Asp Glu Ser Val
                405                 410                 415
```

```
Leu Ser Met His Lys Val Cys Glu Ala Gly Gly Leu Phe Val Asn Ser
            420                 425                 430

Pro Glu Glu Pro Ser Leu Ser Arg Met Val Thr Glu Glu Ile Gln
            435                 440                 445

Phe Tyr Val Gln Gln Phe Lys Lys Ser Gly Phe Arg Gly Pro Leu Asn
        450                 455                 460

Trp Tyr Arg Asn Met Glu Arg Asn Trp Lys Trp Ala Cys Lys Ser Leu
465                 470                 475                 480

Gly Arg Lys Ile Leu Ile Pro Ala Leu Met Val Thr Ala Glu Lys Asp
                485                 490                 495

Phe Val Leu Val Pro Gln Met Ser Gln His Met Glu Asp Trp Ile Pro
            500                 505                 510

His Leu Lys Arg Gly His Ile Glu Asp Cys Gly His Trp Thr Gln Met
            515                 520                 525

Asp Lys Pro Thr Glu Val Asn Gln Ile Leu Ile Lys Trp Leu Asp Ser
            530                 535                 540

Asp Ala Arg Asn Pro Pro Val Val Ser Lys Met
545                 550                 555

<210> SEQ ID NO 2
<211> LENGTH: 2290
<212> TYPE: DNA
<213> ORGANISM: Homo sapiens

<400> SEQUENCE: 2
gtgcccctcc ccctgcctct ttcccggcca gagtccagcc ttaacccggg cagagggcgg      60
agtcccgtta aggggtgtgt gggaggaggc ggggccaggt caggggcggg gcagagccgg     120
gccaagctgg gcgggtcatg cgccctggcc ttcgcgcatc tcccaggtta gctgcgtgtc     180
cgggtgctag gctgcagacc cgccgccatg acgctgcgcg cggccgtctt cgaccttgac     240
ggggtgctgg cgctgccagc ggtgttcggc gtcctcggcc gcacggagga ggccctggcg     300
ctgcccagag gacttctgaa tgatgctttc cagaaagggg accagagggt gccactacc      360 cggcttatga aggagagat cacactttcc cagtggatac cactcatgga agaaaactgc      420
aggaagtgct ccgagaccgc taaagtctgc ctccccaaga atttctccat aaaagaaatc     480
tttgacaagg cgatttcagc cagaaagatc aaccgcccca tgctccaggc agctctcatg     540
ctcaggaaga aaggattcac tactgccatc ctcaccaaca cctggctgga cgaccgtgct     600
gagagagatg gcctggccca gctgatgtgt gagctgaaga tgcactttga cttcctgata     660
gagtcgtgtc agtgtggaat ggtcaaacct gaacctcaga tctacaagtt tctgctggac     720 acccctgaagg ccagccccag tgaggtcgtt ttttggatg acatcggggc taatctgaag     780
ccagcccgtg acttgggaat ggtcaccatc ctggtccagg acactgacac ggccctgaaa     840
gaactggaga aagtgaccgg aatccagctt ctcaataccc cggcccctct gccgacctct     900
tgcaatccaa gtgacatgag ccatgggtac gtgacagtaa agcccagggt ccgtctgcat     960
tttgtggagc tgggctccgg ccctgctgtg tgcctctgcc atggatttcc cgagagttgg    1020
tattcttgga ggtaccagat ccctgctctg gcccaggcag gttaccgggt cctagctatg    1080
gacatgaaag gctatggaga gtcatctgct cctcccgaaa tagaagaata ttgcatggaa    1140
gtgttatgta aggagatggt aaccttcctg gataaactgg gcctctctca gcagtgttc     1200 attggccatg actgggtgg catgctggtg tggtacatgg ctctcttcta ccccgagaga    1260
gtgagggcgg tggccagttt gaatactccc ttcataccag caaatcccaa catgtcccct    1320
```

-continued

```
ttggagagta tcaaagccaa cccagtattt gattaccagc tctacttcca agaaccagga      1380
gtggctgagg ctgaactgga acagaacctg agtcggactt tcaaaagcct cttcagagca      1440
agcgatgaga gtgttttatc catgcataaa gtctgtgaag cgggaggact ttttgtaaat      1500
agcccagaag agcccagcct cagcaggatg gtcactgagg aggaaatcca gttctatgtg      1560
cagcagttca agaagtctgg tttcagaggt cctctaaact ggtaccgaaa catggaaagg      1620
aactggaagt gggcttgcaa aagcttggga cggaagatcc tgattccggc cctgatggtc      1680
acggcggaga aggacttcgt gctcgttcct cagatgtccc agcacatgga ggactggatt      1740
ccccacctga aaggggaca cattgaggac tgtgggcact ggacacagat ggacaagcca       1800
accgaggtga atcagatcct cattaagtgg ctggattctg atgcccggaa cccaccggtg      1860
gtctcaaaga tgtagaacgc agcgtgtgcc cacgctcagc aggtgtgcca tccttccacc      1920
tgctggggca ccattcttag tatacagagg tggccttaca cacatcttgc atggatggca     1980
gcattgttct gaaggggttt gcagaaaaaa aagatttctt ttacataaag tgaatcaaat      2040
ttgacattat tttagatccc agagaaatca ggtgtgatta gttctccagg catgaatgca     2100
tcgtcccttt atctgtaaga accccttagtg tcctgtaggg ggacagaatg gggtggccag    2160
gtggtgattt ctctttgacc aatgcatagt ttggcagaaa aatcagccgt tcatttagaa     2220
gaatcttagc agagattggg atgccttact caataaagct aagatgacta tgctgaaaaa     2280
aaaaaaaaa                                                             2290
```

```
<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cagtgttcat tggccatgac tgg                                               23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
guguucauug gccaugacut t                                                 21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
agucauggcc aaugaacact t                                                 21
```

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gaaaggctat ggagagtcat ctg                                              23

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
aaggcuaugg agagucauct t                                                21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
gaugacucuc cauagccuut t                                                21

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aaaggctatg gagagtcatc tgc                                              23

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
aggcuaugga gagucaucut t                                                21

<210> SEQ ID NO 11
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
agaugacucu ccauagccut t                                              21

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
caagcagtgt tcattggcca tga                                            23

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
agcaguguuc auuggccaut t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
auggccaaug aacacugcut t                                              21

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cagcacatgg aggactggat tcc                                            23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 16
gcacauggag gacuggauut t    21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
aauccagucc uccaugugct t    21

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18 ttcaagaga    9

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cagtgttcat tggccatgac tgg    23

<210> SEQ ID NO 20
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gatccccgtg ttcattggcc atgactttca agagaagtca tggccaatga acactttttt    59

<210> SEQ ID NO 21
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agctaaaaag tgttcattgg ccatgacttc tcttgaaagt catggccaat gaacacggg    59

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gaaaggctat ggagagtcat ctg                                            23

<210> SEQ ID NO 23
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gatccccaag gctatggaga gtcatcttca agagagatga ctctccatag ccttttttt    59

<210> SEQ ID NO 24
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
agctaaaaaa aggctatgga gagtcatctc tcttgaagat gactctccat agccttggg    59

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aaaggctatg gagagtcatc tgc                                            23

<210> SEQ ID NO 26
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gatccccagg ctatggagag tcatctttca agagaagatg actctccata gcctttttt    59

<210> SEQ ID NO 27
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
agctaaaaaa ggctatggag agtcatcatc tcttgaaaga tgactctcca tagcctggg    59

<210> SEQ ID NO 28
<211> LENGTH: 23
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 28
caagcagtgt tcattggcca tga                                           23

<210> SEQ ID NO 29
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gatccccagc agtgttcatt ggccatttca agagaatggc caatgaacac tgcttttt    59

<210> SEQ ID NO 30
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
agctaaaaaa gcagtgttca ttggccattc tcttgaaatg gccaatgaac actgctggg    59

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cagcacatgg aggactggat tcc                                           23

<210> SEQ ID NO 32
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gatccccgca catggaggac tggattttca agagaaatcc agtcctccat gtgctttt    59

<210> SEQ ID NO 33
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
agctaaaaag cacatggagg actggatttc tcttgaaaat ccagtcctcc atgtgcggg    59

<210> SEQ ID NO 34
<211> LENGTH: 20
<212> TYPE: RNA
<213> ORGANISM: Artificial Sequence
<220> FEATURE:
<223> OTHER INFORMATION: Description of Artificial Sequence: Synthetic

```
                        oligonucleotide

<400> SEQUENCE: 34
uguccagugc ccacaguccu                                           20

<210> SEQ ID NO 35
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
uucccaccug acacgacucu                                           20

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
guucagccuc agccacuccu                                           20

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
aguccucccg cuucacaga                                            19

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
gcccacuucc aguuccuuuc c                                         21
```

METHODS OF TREATING MENTAL DISORDERS

CROSS-REFERENCE TO RELATED APPLICATIONS

This application is the U.S. national phase under 35 U.S.C. 371 of International Application No. PCT/US2016/067024, filed on Dec. 15, 2016, which claims the benefit under 35 U.S.C. § 119(e) of U.S. Provisional Application No. 62/275,182, filed on Jan. 5, 2016, which are hereby incorporated herein by reference in their entireties for all purposes.

STATEMENT OF GOVERNMENTAL SUPPORT

This work was supported in part by Grant Nos. R01 ES002710 and P42 ES04699 from National Institutes of Health, National Institute of Environmental Health Sciences. The Government has certain rights in this invention.

BACKGROUND

Depression is the most severe and debilitating of the psychiatric illnesses. The World Health Organization estimates that more than 350 million individuals of all ages suffer from depression (1). Almost one million lives are lost annually due to suicide, which translates to 3,000 deaths daily (1). Although antidepressants are generally effective in the treatment of depression, it can still take weeks before patients feel the full antidepressant effects. However, approximately two-thirds of depressed patients fail to respond fully to pharmacotherapy. Furthermore, there is a high rate of relapse, and depressed patients have a high risk of committing suicide (2-4).

Accumulating evidence suggests that inflammation plays a central role in the pathophysiology of depression (5-9). Meta-analyses showed higher blood levels of pro-inflammatory cytokines, such as tumor necrosis factor (TNF)-α and interleukin-6 (IL-6), in drug-free depressed patients compared with healthy controls (10-13). Studies using postmortem brain samples showed elevated gene expression of pro-inflammatory cytokines in the frontal cortex of people with a history of depression (14,15). Taken together, it is likely that both peripheral and central inflammations are associated with depression and that anti-inflammatory drugs, such as cyclooxygenase inhibitors, could ameliorate depressive symptoms in depressed patients (16,17).

Epoxyeicosatrienoic acids (EETs), which produced from arachidonic acid by the action of cytochrome P450s, have potent anti-inflammatory actions. These mediators are broken down into the corresponding diols by soluble epoxide hydrolase (sEH), and inhibition of sEH enhances the beneficial effects of EETs (18-21). It is also reported that sEH inhibitors have potent anti-inflammatory effects in a number of animal models (18-20,22,23). While sEH has been associated with the onset of anorexia nervosa (24), the role of sEH in the pathophysiology of depression has not been studied to date.

SUMMARY

The present methods are based, in part, on the discovery that soluble epoxide hydrolase (sEH) plays a role in the pathophysiology of depression and other neuropsychiatric disorders.

In one aspect, provided are methods of preventing, reducing, ameliorating, mitigating, inhibiting and/or reversing one or more symptoms associated with a neuropsychiatric disorder having or characterized by depressive symptoms in a subject in need thereof. In some embodiments, the methods comprise administering to the subject an agent that increases the level of epoxy-fatty acids, or a functional derivative or mimic thereof, as sole active agent or co-administered with a second agent.

In another aspect, provided are methods of accelerating responsiveness to pharmacological treatment and/or preventing, reducing, ameliorating, mitigating, delaying, inhibiting and/or reversing recurrence and/or relapse of one or more symptoms associated with a neuropsychiatric disorder of a neuropsychiatric disorder having or characterized by depressive symptoms in a subject in need thereof. In some embodiments, the methods comprise administering to the subject an agent that increases the level of epoxy-fatty acids, or a functional derivative or mimic thereof, as sole active agent or co-administered with a second agent. In a related aspect, provided are methods of enhancing (e.g., accelerating desired effects, increasing efficacy and/or potency) the pharmacological effectiveness of an antidepressant, a mood stabilizer, an antipsychotic drug or an anti-anxiety drug. In some embodiments, the methods comprise co-administering to the subject an agent that increases the level of epoxy-fatty acids with an antidepressant, a mood stabilizer, an antipsychotic drug or an anti-anxiety drug.

In another aspect, provided are methods of potentiating nerve growth factor (NGF)-induced neurite outgrowth. In varying embodiments, the methods comprise contacting a neuron with an agent that increases the level of epoxy-fatty acids, or a functional derivative or mimic thereof. The neuron may be in vitro or in vivo.

With respect to embodiments of the methods, in some embodiments, the second agent is an antidepressant, a mood stabilizer, an antipsychotic drug or an anti-anxiety drug. In varying embodiments, the second agent is an antidepressant, a mood stabilizer, an antipsychotic drug or an anxiolytic. In varying embodiments, the antidepressant is selected from the group consisting of a selective serotonin reuptake inhibitor (SSRI), a serotonin-norepinephrine reuptake inhibitor (SNRI), a tricyclic or tetracyclic antidepressant (TCA), a monoamine oxidase inhibitor (MAOI) and an atypical antidepressant. In varying embodiments, the selective serotonin reuptake inhibitor (S SRI) is selected from the group consisting of citalopram, escitalopram, fluoxetine, fluvoxamine, fluvoxamine CR, paroxetine, paroxetine CR, and sertraline. In varying embodiments, the serotonin-norepinephrine reuptake inhibitor (SNRI) is selected from the group consisting of desvenlafaxine, duloxetine, venlafaxine, venlafaxine XR, milnacipran, and levomilnacipran. In varying embodiments, the tricyclic or tetracyclic antidepressant (TCA) is selected from the group consisting of amitriptyline, amoxapine, desipramine, doxepin, imipramine, nortriptyline, protriptyline, trimipramine and maprotiline. In varying embodiments, the monoamine oxidase inhibitor (MAOI) is selected from the group consisting of as selegiline, moclobemide, tranylcypromine, isocarboxazid and phenylzine. In varying embodiments, the mood stabilizer is selected from the group consisting of lithium carbonate, divalproex sodium, valproic acid, valproate semisodium, sodium valproate, tiagabine, levetiracetam, lamotrigine, gabapentin, carbamazepine, oxcarbazepine, topiramate, zonisamide, aripiprazole, risperidone, olanzapine, quetiapine, asenapine, paliperidone, ziprasidone, lurasidone, verapamil, clonidine, propranolol, mexiletine, guanfacine and omega-3 fatty acids. In varying embodiments, the antipsychotic is selected from the group consisting of a butyrophenone, a diphenylbutylpiperidine, a phenothiazine, a thioxanthene, or is an atypical antipsychotic agent. In varying embodiments, the antipsychotic is selected from the group consisting of benperidol. bromperidol, droperidol, haloperidol, moperone, pipamperone, timiperone, fluspirilene, penfluridol, pimozide, phenothiazines, acepromazine, chlorpromazine, cyamemazine, dixyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, thioxanthenes, chlorprothixene, clopenthixol, flupentixol, thiothixene, zuclopenthixol, clotiapine, loxapine, prothipendyl, carpipramine, clocapramine, molindone, mosapramine, sulpiride, sultopride, veralipride, amisulpride, amoxapine, aripiprazole, asenapine, cariprazine, clozapine, blonanserin, iloperidone, lurasidone, melperone, nemonapride, olanzapine, paliperidone, perospirone, quetiapine, remoxipride, risperidone, sertindole, sultopride, trimipramine, ziprasidone, zotepine, brexpiprazole, ITI-007, pimavanserin and RP5063. In varying embodiments, the anxiolytic drug is selected from the group consisting of a barbiturate, a benzodiazepine and a beta-blocker. In varying embodiments, the anxiolytic drug is selected from the group consisting of alprazolam, bromazepam, chlordiazepoxide, clonazepam, clorazepate, diazepam, flurazepam, lorazepam, oxazepam, temazepam, triazolam, tofisopam, clonidine, guanfacine, mebicar, fabomotizole, selank, bromantane, emoxypine, buspirone, tandospirone, hydroxyzine, pregabalin, menthyl isovalerate, cannabidiol (cbd), tetrahydrocannabinol, *Garcinia indica* (kokum), *Scutellaria lateriflora, Coriandrum sativum* (coriander), *Salvia elegans* (pineapple sage), picamilon, chlorpheniramine, diphenhydramine, melatonin and myo-inositol. In varying embodiments, the neuropsychiatric disorder is selected from the group consisting of depression, major depression, schizophrenia, bipolar disorder, post-traumatic disorder (PTSD), eating disorder, substance abuse, drug addiction, drug dependency, social anxiety, Alzheimer's disease, dementia, and attention-deficit hyperactivity disorder (ADHD). In varying embodiments, one or both of the agent that increases the level of epoxy-fatty acids and the second agent are administered at a subtherapeutic or therapeutically ineffective dose. In varying embodiments, one or more symptoms associated with the neuropsychiatric disorder having or characterized by depressive symptoms are improved within 1 week, e.g., within 7, 6, 5, 4, 3, 2, 1 days, or within, 24, 20, 18, 16, 14, 12, 10, 8, 6, 4, 2 hours, or less, after receiving a regime of administration of the agent that increases the level of epoxy-fatty acids. In varying embodiments, the improved symptoms (e.g., antidepressant, mood-stabilizing, anti-anxiety effects) are sustained over an extended period of time, e.g., without relapse. In varying embodiments, the regime comprises daily administration of the agent that increases the level of epoxy-fatty acids. In varying embodiments, the agent that increases the level of epoxy-fatty acids is administered via a route selected from the group consisting of oral, buccal, sublingual, intrapulmonary, intranasal, intravenous (IV), topical, transdermal, intradermal and subcutaneous. In varying embodiments, the agent that increases the level of epoxy-fatty acids comprises one or more epoxy-fatty acids. In varying embodiments, the epoxy-fatty acids are selected from the group consisting of cis-epoxyeicosantrienoic acids ("EETs"), epoxides of linoleic acid, epoxides of eicosapentaenoic acid ("EPA"), epoxides of docosahexaenoic acid ("DHA"), epoxides of the arachidonic acid ("AA"), epoxides of cis-7,10,13,16,19-docosapentaenoic acid, and mixtures thereof. In varying embodiments, the agent that increases the level of epoxy-fatty acids increases the levels of cis-epoxyeicosantrienoic acids ("EETs"). In varying embodiments, the agent that increases the level of EETs is an inhibitor of soluble epoxide hydrolase ("sEH"). In varying embodiments, the inhibitor of sEH comprises an inhibitory nucleic acid that specifically targets soluble epoxide hydrolase ("sEH"). In varying embodiments, the inhibitory nucleic acid is selected from the group consisting of short interfering RNA (siRNA), short hairpin RNA (shRNA), small temporal RNA (stRNA), and micro-RNA (miRNA). In varying embodiments, the inhibitor of sEH comprises a primary or central pharmacophore selected from the group consisting of a urea, a carbamate, and an amide. In varying embodiments, the inhibitor of sEH comprises a cyclohexyl moiety, aromatic moiety, substituted aromatic moiety or alkyl moiety attached to the pharmacophore. In varying embodiments, the inhibitor of sEH comprises a cyclohexyl ether moiety attached to the pharmacophore. In varying embodiments, the inhibitor of sEH comprises a phenyl ether or piperidine moiety attached to the pharmacophore. In varying embodiments, the inhibitor of sEH comprises a polyether secondary pharmacophore. In varying embodiments, the inhibitor of sEH has an IC50 of less than about 100 µM. In varying embodiments, the inhibitor of sEH is selected from the group consisting of:

a) 3-(4-chlorophenyl)-1-(3,4-dichlorphenyl)urea or 3,4, 4'-trichlorocarbanilide (TCC; compound 295);

b) 12-(3-adamantan-1-yl-ureido) dodecanoic acid (AUDA; compound 700);

c) 1-adamantanyl-3-{5-[2-(2-ethoxyethoxy)ethoxy]pentyl]}urea (AEPU; compound 950);

d) 1-(1-acetypiperidin-4-yl)-3-adamantanylurea (APAU; compound 1153);

e) trans-4-[4-(3-Adamantan-1-yl-ureido)-cyclohexyloxy]-benzoic acid (tAUCB; compound 1471);

f) cis-4-[4-(3-Adamantan-1-yl-ureido)-cyclohexyloxy]-benzoic acid (cAUCB; compound 1686);

g) 1-(1-methylsulfonyl-piperidin-4-yl)-3-(4-trifluoromethoxy-phenyl)-urea (TUPS; compound 1709);

h) trans-4-{4-[3-(4-Trifluoromethoxy-phenyl)-ureido]-cyclohexyloxy}-benzoic acid (tTUCB; compound 1728);

i) 1-trifluoromethoxyphenyl-3-(1-propionylpiperidin-4-yl) urea (TPPU; compound 1770);

j) 1-(1-ethylsulfonyl-piperidin-4-yl)-3-(4-trifluoromethoxy-phenyl)-urea (TUPSE; compound 2213);

k) 1-(1-(cyclopropanecarbonyl)piperidin-4-yl)-3-(4-(trifluoromethoxy)phenyl)urea (CPTU; compound 2214);

l) trans-N-methyl-4-[4-(3-Adamantan-1-yl-ureido)-cyclohexyloxy]-benzamide (tMAUCB; compound 2225);

m) trans-N-methyl-4-[4-((3-trifluoromethyl-4-chlorophenyl)-ureido)-cyclohexyloxy]-benzamide (tMTCUCB; compound 2226);

n) cis-N-methyl-4-{4-[3-(4-trifluoromethoxy-phenyl)-ureido]-cyclohexyloxy}-benzamide (cMTUCB; compound 2228);

o) 1-cycloheptyl-3-(3-(1,5-diphenyl-1H-pyrazol-3-yl) propyl)urea (HDP$_3$U; compound 2247);

p) trans-2-(4-(4-(3-(4-trifluoromethoxy-phenyl)-ureido)-cyclohexyloxy)-benzamido)-acetic acid (compound 2283);

q) N-(methylsulfonyl)-4-(trans-4-(3-(4-trifluoromethoxy-phenyl)-ureido)-cyclohexyloxy)-benzamide (compound 2728);

r) 1-(trans-4-(4-(1H-tetrazol-5-yl)-phenoxy)-cyclohexyl)-3-(4-(trifluoromethoxy)-phenyl)-urea (compound 2806);

s) 4-(trans-4-(3-(2-fluorophenyl)-ureido)-cyclohexyloxy)-benzoic acid (compound 2736);

t) 4-(4-(3-(4-(trifluoromethoxy)-phenyl)-ureido)-phenoxy)-benzoic acid (compound 2803);

u) 4-(3-fluoro-4-(3-(4-(trifluoromethoxy)-phenyl)-ureido)-phenoxy)-benzoic acid (compound 2807);

v) N-hydroxy-4-(trans-4-(3-(4-(trifluoromethoxy)-phenyl)-ureido)-cyclohexyloxy)-benzamide (compound 2761);

w) (5-methyl-2-oxo-1,3-dioxol-4-yl)methyl 4-((1r,4r)-4-(3-(4-(trifluoromethoxy)-phenyl)-ureido)-cyclohexyloxy)-benzoate (compound 2796);

x) 1-(4-oxocyclohexyl)-3-(4-(trifluoromethoxy)-phenyl)-urea (compound 2809);

y) methyl 4-(4-(3-(4-(trifluoromethoxy)-phenyl)-ureido)-cyclohexylamino)-benzoate (compound 2804);

z) 1-(4-(pyrimidin-2-yloxy)-cyclohexyl)-3-(4-(trifluoromethoxy)-phenyl)-urea (compound 2810);

aa) 4-(trans-4-(3-(4-(difluoromethoxy)-phenyl)-ureido)-cyclohexyloxy)-benzoic acid (compound 2805); and bb) (1R,3 S)—N-(4-cyano-2-(trifluoromethyl)benzyl)-3-((4-methyl-6-(methylamino)-1,3,5-triazin-2-yl)amino)cyclohexane-1-carboxamide (GSK2256294A).

In another aspect, provided are kits. In varying embodiments, the kits comprise (i) one or more first agents that increase the level of epoxy-fatty acids; and (ii) one or more second agents comprise an antidepressant, a mood stabilizer, an antipsychotic drug and/or an anxiolytic. In varying embodiments, the first agents and the second agents are mixed in a single container. In varying embodiments, the first agents and the second agents are provided in separate containers. In varying embodiments, one or both of the first agents and the second agents are provided in subtherapeutic or therapeutically ineffective unit doses.

Definitions

Units, prefixes, and symbols are denoted in their Système International d'Unités (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments, which can be had by reference to the specification as a whole. Accordingly, the terms defined immediately below are more fully defined by reference to the specification in its entirety. Terms not defined herein have their ordinary meaning as understood by a person of skill in the art.

"cis-Epoxyeicosatrienoic acids" ("EETs") are biomediators synthesized by cytochrome P450 epoxygenases. As discussed further in a separate section below, while the use of unmodified EETs is the most preferred, derivatives of EETs, such as amides and esters (both natural and synthetic), EETs analogs, and EETs optical isomers and corresponding EPA and DHA derivatives, including omega-3-derived epoxides epoxyeicosatetraenoic acids (EEQs) and epoxydocosapentaenoic acids (EDPs), can all be used in the methods, both in pure form and as mixtures of these forms. For convenience of reference, the term "EETs" as used herein refers to all of these forms unless otherwise required by context.

"Epoxide hydrolases" ("EH;" EC 3.3.2.3) are enzymes in the alpha beta hydrolase fold family that add water to 3-membered cyclic ethers termed epoxides.

"Soluble epoxide hydrolase" ("sEH"; EC 3.3.2.10) is an epoxide hydrolase which in cells converts EETs to dihydroxy derivatives called dihydroxyeicosatrienoic acids ("DHETs"). The cloning and sequence of the murine sEH is set forth in Grant et al., J. Biol. Chem. 268(23):17628-17633 (1993). The cloning, sequence, and accession numbers of the human sEH sequence are set forth in Beetham et al., Arch. Biochem. Biophys. 305(1):197-201 (1993). The amino acid sequence of human sEH is SEQ ID NO.:1, while the nucleic acid sequence encoding the human sEH is SEQ ID NO.:2. (The sequence set forth as SEQ ID NO.:2 is the coding portion of the sequence set forth in the Beetham et al. 1993 paper and in the NCBI Entrez Nucleotide Browser at accession number L05779, which include the 5' untranslated region and the 3' untranslated region.) The evolution and nomenclature of the gene is discussed in Beetham et al., DNA Cell Biol. 14(1):61-71 (1995). Soluble epoxide hydrolase represents a single highly conserved gene product with over 90% homology between rodent and human (Arand et al., FEBS Lett., 338:251-256 (1994)). Unless otherwise specified, as used herein, the terms "soluble epoxide hydrolase" and "sEH" refer to human sEH.

Unless otherwise specified, as used herein, the term "sEH inhibitor" (also abbreviated as "sEHI") refers to an inhibitor of human sEH. Preferably, the inhibitor does not also inhibit the activity of microsomal epoxide hydrolase by more than 25% at concentrations at which the inhibitor inhibits sEH by at least 50%, and more preferably does not inhibit mEH by more than 10% at that concentration. For convenience of reference, unless otherwise required by context, the term "sEH inhibitor" as used herein encompasses prodrugs which are metabolized to active inhibitors of sEH. Further for convenience of reference, and except as otherwise required by context, reference herein to a compound as an inhibitor of sEH includes reference to derivatives of that compound (such as an ester of that compound) that retain activity as an sEH inhibitor.

Cytochrome P450 ("CYP450") metabolism produces cis-epoxydocosapentaenoic acids ("EpDPEs") and cis-epoxyeicosatetraenoic acids ("EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS- (nitric oxide) and COX-derived (prostacyclin) vasodilators. Overall cytochrome P450 (CYP450) metabolism of polyunsaturated fatty acids produces epoxides, such as EETs, which are prime candidates for the active mediator(s). 14(15)-EpETE, for example, is derived via epoxidation of the 14,15-double bond of EPA and is the ω-3 homolog of 14(15)-EpETrE ("14(15)EET") derived via epoxidation of the 14,15-double bond of arachidonic acid.

"$IC_{50}$" refers to the concentration of an agent required to inhibit enzyme activity by 50%.

"Micro-RNA" ("miRNA") refers to small, noncoding RNAs of 18-25 nt in length that negatively regulate their complementary mRNAs at the posttranscriptional level in many eukaryotic organisms. See, e.g., Kurihara and Watanabe, Proc Natl Acad Sci USA 101(34):12753-12758 (2004). Micro-RNA's were first discovered in the roundworm C. elegans in the early 1990s and are now known in many species, including humans. As used herein, it refers to exogenously administered miRNA unless specifically noted or otherwise required by context.

The term "therapeutically effective amount" refers to that amount of the compound being administered sufficient to prevent or decrease the development of one or more of the symptoms of the disease, condition or disorder being treated (e.g., fibrosis and/or inflammation).

The terms "prophylactically effective amount" and "amount that is effective to prevent" refer to that amount of drug that will prevent or reduce the risk of occurrence of the biological or medical event that is sought to be prevented. In many instances, the prophylactically effective amount is the same as the therapeutically effective amount.

"Subtherapeutic dose" refers to a dose of a pharmacologically active agent(s), either as an administered dose of pharmacologically active agent, or actual level of pharmacologically active agent in a subject that functionally is insufficient to elicit the intended pharmacological effect in itself (e.g., to obtain analgesic, anti-inflammatory, and/or anti-fibrotic effects), or that quantitatively is less than the established therapeutic dose for that particular pharmacological agent (e.g., as published in a reference consulted by a person of skill, for example, doses for a pharmacological agent published in the Physicians' Desk Reference, 69th Ed., 2015, PDR Network or Brunton, et al., Goodman & Gilman's The Pharmacological Basis of Therapeutics, 12th edition, 2010, McGraw-Hill Professional). A "subtherapeutic dose" can be defined in relative terms (i.e., as a percentage amount (less than 100%) of the amount of pharmacologically active agent conventionally administered). For example, a subtherapeutic dose amount can be about 1% to about 75% of the amount of pharmacologically active agent conventionally administered. In some embodiments, a subtherapeutic dose can be about 75%, 50%, 30%, 25%, 20%, 10% or less, than the amount of pharmacologically active agent conventionally administered.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in Remington: The Science and Practice of Pharmacy, University of the Sciences in Philadelphia, Eds., 21$^{st}$ Ed., Lippencott Williams & Wilkins (2005).

The terms "sustained release" and "extended release" are used in their conventional sense to refer to a drug formulation that provides for gradual release of a drug over an extended period of time, for example, 12 hours or more, and that preferably, although not necessarily, results in substantially steady-state blood levels of a drug over an extended time period.

As used herein, the term "delayed release" refers to a pharmaceutical preparation that passes through the stomach intact and dissolves in the small intestine.

As used herein, "synergy" or "synergistic" interchangeably refer to the combined effects of two active agents that are greater than their additive effects. Synergy can also be achieved by producing an efficacious effect with combined inefficacious doses of two active agents. The measure of synergy is independent of statistical significance.

The terms "systemic administration" and "systemically administered" refer to a method of administering agent (e.g., an agent that increases epoxy-fatty acids (e.g., an inhibitor of sEH, an EET, an epoxy-fatty acid, and mixtures thereof; optionally co-administered with a second agent (e.g., antidepressant, mood stabilizer, anti-psychotic, anxiolytic)) to a mammal so that the agent/cells is delivered to sites in the body, including the targeted site of pharmaceutical action, via the circulatory system. Systemic administration includes, but is not limited to, oral, intranasal, rectal and parenteral (i.e other than through the alimentary tract, such as intramuscular, intravenous, intra-arterial, transdermal and subcutaneous) administration.

The term "co-administration" refers to the presence of both active agents/cells in the blood or body at the same time. Active agents that are co-administered can be delivered concurrently (i.e., at the same time) or sequentially.

The phrase "cause to be administered" refers to the actions taken by a medical professional (e.g., a physician), or a person controlling medical care of a subject, that control and/or permit the administration of the agent(s)/compound(s)/cell(s) at issue to the subject. Causing to be administered can involve diagnosis and/or determination of an appropriate therapeutic or prophylactic regimen, and/or prescribing particular agent(s)/compounds/cell(s) for a subject. Such prescribing can include, for example, drafting a prescription form, annotating a medical record, and the like.

The terms "patient," "subject" or "individual" interchangeably refers to a non-human mammal, including primates (e.g., macaque, pan troglodyte, pongo), a domesticated mammal (e.g., felines, canines), an agricultural mammal (e.g., bovine, ovine, porcine, equine) and a laboratory mammal or rodent (e.g., rattus, murine, lagomorpha, hamster).

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

The terms "inhibiting," "reducing," "decreasing" refers to inhibiting the disease condition of interest (e.g., neuropsychiatric illness, e.g., depression, major depression, schizophrenia, bipolar disorder, post-traumatic disorder (PTSD), eating disorder, substance abuse, drug addiction, drug dependency, social anxiety, Alzheimer's disease, dementia, and attention-deficit hyperactivity disorder (ADHD)) in a mammalian subject by a measurable amount using any method known in the art. For example, one or more symptoms of a neuropsychiatric illness is inhibited, reduced or decreased if an indicator of the neuropsychiatric illness is reduced by a measureable amount, either quantitatively or qualitatively, e.g., in comparison to the same inflammatory indicator prior to administration of an agent that increases epoxy-fatty acids (e.g., an inhibitor of sEH, an EET, an epoxy-fatty acid, and mixtures thereof). Qualitative and quantitative measures of neuropsychiatric illnesses are known in the art, and described, e.g., in the Diagnostic and Statistical Manual of Mental Disorders, 5th Edition (DSM-5) American Psychiatric Association, American Psychiatric Publishing, 2013 and/or the International Statistical Classification of Diseases and Related Health Problems (ICD)-11 of the World Health Organization (WHO) (available online at http://www.who.int/classifications/icd/en/). Symptoms for patients with psychiatric disorders can be measured and quantified using appropriate tests and scales established in the art, e.g., HAMD (Hamilton Depression Rating Scale) (Williams, *Arch Gen Psychiatry.* 1988 August; 45(8):742-7 and Zimmerman, et al., *J Affect Disord.* 2013 Sep. 5; 150(2):384-8), HAMA (Hamilton Anxiety Rating Scale) (Bruss, et al., *Psychiatry Res.* 1994 August; 53(2):191-202), YMRS (Young Mania Rating Scale) (Lukasiewicz, et al., *Int J Methods Psychiatr Res.* 2013 March; 22(1):46-58), BPRS (Brief Psychiatric Rating Scale) (Bell, et al., *J Nerv Ment Dis.* 1992 November; 180(11):723-8 and Lachar, et al., *J Am Acad Child Adolesc Psychiatry.* 2001 March; 40(3):333-40), PANSS (Positive and Negative Syndrome Scale) (Kay, et al., Schizophr Bull. 1987; 13(2):261-76 and Kay, et al., *Psychiatry Res.* 1988 January; 23(1):99-110), and/or CGS-I (Clinical Global Impression—Severity) (Pinna, et al., *Ann Gen Psychiatry.* 2015 Feb. 13; 14:6).

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than the listed active agents, e.g., an agent that increases epoxy-fatty acids (e.g., an inhibitor of sEH, an EET, an epoxy-fatty acid, and mixtures thereof) and/or an anti-inflammatory agent.

BRIEF DESCRIPTION OF THE DRAWINGS

FIGS. 1A-B illustrate TPPU and 14,15-EET potentiated NGF-induced neurite outgrowth in PC12 cells. (A): Representative photomicrographs in PC12 cells. Control: NGF (2.5 ng/ml) alone, TPPU (10 μM): NGF (2.5 ng/ml)+TPPU (10 μM), 14,15-EET (1.0 μM): NGF (2.5 ng/ml)+14,15-EET (1.0 μM). The arrow is the cells with neurite outgrowth. Bar=50 μm. (B): Effects of TPPU and 14,15-EET on NGF-induced neurite outgrowth in PC12 cells. TPPU (0.1, 1.0, or 10 μM: one-way ANOVA, $F_{3,44}$=15.591, P<0.001) and 14,15-EET (0.01, 0.1, or 1.0 μM; one-way ANOVA, $F_{3,38}$=12.687, P<0.001) potentiated NGF-induced neurite outgrowth in PC12 cells, in a concentration-dependent manner. Data show the mean±SEM (n=6-12). P<0.01, *P<0.001 compared to control group (post-hoc Tukey test).

FIGS. 2A-K illustrate the effects of TPPU in an inflammation model of depression. (A): Schedule of treatment and blood collection. (B): Pretreatment with TPPU (0.3, 1.0, or 3.0 mg/kg, PO) attenuated increased serum levels of TNF-α after a single administration of LPS (0.5 mg/kg, IP), in a dose dependent manner. Data are shown as mean±S.E.M. (n=5 or 6). *P<0.05, ***P<0.001 compared to vehicle+LPS group (one-way ANOVA, $F_{5,27}$=26.67, P<0.001, post-hoc Tukey test). (C): Schedule of treatment and behavioral tests. Vehicle or TPPU (3 mg/kg, PO) was administered 23 hours after a single administration of LPS (0.5 mg/kg, IP) or saline. Behavioral tests, including locomotion (LMT), tail suspension test (TST), and forced swimming test (FST) were performed. (D-F): Two-way ANOVA revealed the results (LMT, LPS: $F_{1,26}$=3.040, P=0.093, TPPU: $F_{1,26}$=0.078, P=0.783; interaction: $F_{1,26}$=0.001, P=0.970), (TST, LPS: $F_{1,28}$=5.357, P=0.028, TPPU: $F_{1,28}$=4.428, P=0.044; interaction: $F_{1,28}$=5.937, P=0.021) and (FST; LPS: $F_{1,27}$=5.974, P=0.021, TPPU: $F_{1,27}$=6.747, P=0.015; interaction: $F_{1,27}$=5.738, P=0.024). Data are shown as mean±S.E.M. (n=7-9). *P<0.05 compared to control group (post-hoc Tukey test). N.S.: Not significant. (G): Schedule of treatment and behavioral tests. Water alone or water including TPPU (15 mg/L) was given for 3-weeks before a single administration of LPS (0.5 mg/kg, IP). LMT, TST, and FST were performed 24, 26 and 28 hours after LPS administration. (H): There were no changes for body weight increase of two groups (repeated one-way ANOVA, $F_{3,29}$=1.894, P=0.153). (I-K): Two-way ANOVA revealed the results (LMT, TPPU: $F_{1,20}$=0.725, P=0.405, LPS: $F_{1,20}$=2.415, P=0.136; interaction: $F_{1,20}$=0.083, P=0.776), (TST, TPPU: $F_{1,20}$=4.814, P=0.040, LPS: $F_{1,20}$=5.529, P=0.029; interaction: $F_{1,20}$=13.93, P=0.001), and (FST, TPPU: $F_{1,20}$=6.708, P=0.017, LPS: $F_{1,20}$=9.939, P=0.005; interaction: $F_{1,20}$=4.542, P=0.046). Data are shown as mean±S.E.M. (n=6). *P<0.05 compared to control group (post-hoc Tukey test). N.S.: Not significant.

FIGS. 3A-B illustrate the pharmacokinetic profile of TPPU in mice. The concentration of TPPU in the brain and blood increased rapidly after a single administration of TPPU (3 mg/kg, PO). The half-life of TPPU in the blood and cerebral cortex was 17.8 and 10.7 hours, respectively. Data at each time point are shown as mean±S.E.M. (n=3).

FIGS. 4A-I illustrate the effects of TPPU in repeated social defeat stress model of depression. (A): Schedule of treatment, social defeat stress, and behavioral tests. Vehicle or TPPU (3 mg/kg/day for 10 days, Day 1-Day 10) was administered orally 60 min before each social defeat stress. One % sucrose preference test (SPT) was performed 24 hours after the social interaction test. (B, C): One-way ANOVA revealed the results (social interaction time (s); no target: $F_{2,24}$=1.859, P=0.178, target: $F_{2,24}$=29.97, P<0.001), and (SPT; $F_{2,23}$=7.362, P=0.003). Data are shown as mean±S.E.M. (n=7-10). *P<0.05, P<0.01, *P<0.001 compared to control group (post-hoc Tukey test). N.S.: Not significant. (D): Schedule of social defeat stress, drug treatment and behavioral tests. Repeated social defeat stress model was performed (Day 1-Day 10). Vehicle or TPPU (3 mg/kg, PO) was administered into depressed mice 24 hours after social interaction test. Behavioral tests, including LMT, TST, and FST were performed 2, 4, 6 hours after a single administration of vehicle or TPPU, respectively. One % SPT was performed 48 hours after a single administration of vehicle or TPPU (3 mg/kg, PO). (E): Mice with depression-like behaviors were selected by social interaction test (social interaction time (s); no target: t=1.990, P=0.052, target: t=21.46, P<0.001). N.S.: Not significant. (F-I): Two-way ANOVA showed the results (LMT, Stress; $F_{1,39}$=1.412, P=0.242; TPPU: $F_{1,39}$=0.088, P=0.769; interaction: $F_{1,39}$=0.363, P=0.551), (TST, Stress; $F_{1,34}$=4.495, P=0.025; TPPU: $F_{1,34}$=5.666, P=0.023; interaction: $F_{1,34}$=4.600, P=0.039), (FST, Stress; $F_{1,35}$=7.752, P=0.009; TPPU: $F_{1,35}$=4.490, P=0.041; interaction: $F_{1,35}$=4.262, P=0.046), and (SPT, Stress; $F_{1,39}$=4.920, P=0.032; TPPU: $F_{1,39}$=7.122, P=0.011; interaction: $F_{1,39}$=5.875, P=0.020). Data are shown as mean±S.E.M. (n=7-16). *P<0.05, **P<0.01 compared to control group (post-hoc Tukey test). N.S.: Not significant.

FIGS. 5A-K illustrate the effect of social defeat stress in sEH KO mice. (A): Schedule of behavioral tests. Behavioral tests, including LMT, TST, FST, and 1% SPT were performed at Day 1 and Day 2. (B-E): Analysis showed the results (LMT; t=1.130, P=0.395), (TST; t=1.952, P=0.386), (FST; t=0.879, P=0.387), and (SPT; t=1.069, P=0.367). Data are shown as mean±S.E.M. (n=12-16). N.S.: Not significant. (F): Schedule of social defeat stress and behavioral tests. Repeated social defeat stress was performed from Day 1-Day 10. Social interaction test was performed on Day 11. Behavioral tests, including LMT, TST, FST, and 1% SPT were performed at Day 12 and Day 13. (G): One-way ANOVA revealed the results (social interaction time (s); no target: $F_{2,30}$=0.951, P=0.398, target: $F_{2,32}$=11.91, P<0.001). N.S.: Not significant. (H-K): (C, D): One-way ANOVA showed the results (LMT; $F_{2,26}$=1.505, P=0.241), (TST; $F_{2,26}$=5.849, P=0.008), (FST; $F_{2,23}$=6.956, P=0.004), and (SPT; $F_{2,29}$=8.197, P=0.002). Data are shown as mean±S.E.M. (n=8-16). *P<0.05, P<0.01, *P<0.001 compared to control group (post-hoc Tukey test). N.S.: Not significant.

FIGS. 6A-E illustrate protein levels of sEH and enzyme activity in the brain from mice with depression-like phenotype and depressed patients. (A): Brain regions were collected 24 hours after a single administration of saline or LPS (0.5 mg/kg, IP). Western blot analysis of sEH protein was performed. PFC (t=2.511, P=0.031), NAc (t=0.035, P=0.973), striatum (t=2.523, P=0.030), CA1 (t=3.458, P=0.006), CA3 (t=2.439, P=0.041), DG (t=2.608, P=0.026). The values are the mean±S.E.M. (n=5-7). *P<0.05, **P<0.01 compared to control group (Student t-test). (B): Social defeat stress was performed 10 days. Twenty four hours after the final stress, social interaction test was performed. Brain regions (PFC, NAc, striatum, hippocampus (CA1, CA3, DG)) from chronically stressed (susceptible) mice were collected. Western blot analysis of sEH protein was performed. PFC (t=6.356, P<0.001), NAc (t=0.345, P=0.738), striatum (t=3.059, P=0.010), CA1 (t=3.016, P=0.017), CA3 (t=2.755, P=0.022), DG (t=6.483, P<0.001). The values represent the mean±S.E.M. (n=5-7). *P<0.05, ***P<0.001 compared to control group (Student t-test). (C): Western blot analysis of sEH in the parietal cortex (BA7) from control (N=15), depression (N=15), bipolar disorder (N=15), and schizophrenia (N=15). Protein levels of sEH in the parietal cortex from depression, bipolar disorder, and schizophrenia were significantly higher than those on controls. One-way ANOVA showed the results ($F_{3,56}$=4.364, P=0.008). Data are shown as mean±S.E.M. (n=15). *P<0.05, **P<0.01 compared to control group (post-hoc Tukey test). (D): Western blot analysis of sEH in the cerebellum from control (N=15), depression (N=15), bipolar disorder (N=15), and schizophrenia (N=15). Protein levels of sEH in the cerebellum from depression, bipolar disorder, and schizophrenia were not different among the four groups ($F_{3,56}$=1.389, P=0.256). Data are shown as mean±S.E.M. (n=15). N.S.: Not significance. (E): Repeated social defeat stress was performed 10 days. Twenty four hours after the final stress, social interaction test was performed. Brain regions (frontal cortex, striatum, hippocampus) from chronically stressed (susceptible) mice were used for analysis of sEH-like enzyme activity. Frontal cortex (t=4.817, P<0.001), striatum (t=2.975, P=0.010), hippocampus (t=2.920, P=0.012). The values represent the mean±S.E.M. (n=8). *P<0.05, P<0.01, *P<0.001 compared to control group (Student t-test).

FIGS. 8A-G illustrate increased levels of BDNF, TrkB phosphorylation, GluA1, and PSD-95 in the brain regions from sEH KO mice. (A, B): Western blot analysis of BDNF (A: mature form) and its precursor proBDNF (B) in PFC, NAc, striatum, CA1, CA3 and DG from sEH KO mice and WT mice was performed. The values are expressed as a percentage of that of control mice. (A): BDNF (mature form): PFC (t=2.438, P=0.041), NAc (t=1.146, P=0.285), striatum (t=0.876, P=0.407), CA1 (t=2.752, P=0.025), CA3 (t=3.130, P=0.014), DG (t=2.383, P=0.044). (B): proBDNF: PFC (t=1.478, P=0.178), NAc (t=0.820, P=0.436), striatum (t=1.050, P=0.324), CA1 (t=0.485, P=0.641), CA3 (t=1.048, P=0.325), DG (t=1.772, P=0.114). (C): The ratio of p-TrkB to total TrkB in the brain regions is shown. Total levels of TrkB protein in the all regions are not different between the two groups. p-TrkB/TrkB: PFC (t=3.591, P=0.007), NAc (t=1.255, P=0.245), striatum (t=0.984, P=0.354), CA1 (t=2.673, P=0.028), CA3 (t=2.501, P=0.037), DG (t=3.168, P=0.013). The values represent the mean±S.E.M. (n=5). *P<0.05, **P<0.01 (Student t-test). (D): Representative data of Western blot analyses of BDNF (mature form), proBDNF, p-TrkB, TrkB, and (β-actin in the mouse brain regions. (E): GluA1: PFC (t=4.472, P=0.001), NAc (t=0.590, P=0.566), striatum (t=1.185, P=0.266), CA1 (t=3.083, P=0.013), CA3 (t=2.827, P=0.018), DG (t=2.699, P=0.024). (F): PSD-95: PFC (t=4.072, P=0.002), NAc (t=1.197, P=0.254), striatum (t=0.326, P=0.751), CA1 (t=2.652, P=0.026), CA3 (t=2.819, P=0.023), DG (t=2.723, P=0.021). The values represent the mean±S.E.M. (n=5-7). *P<0.05, P<0.01, *P<0.001 (Student t-test). (G): Representative data of Western blot analyses of GluA1, PSD-95, and (β-actin in the mouse brain regions.

DETAILED DESCRIPTION

1. Introduction

Figure 1A:
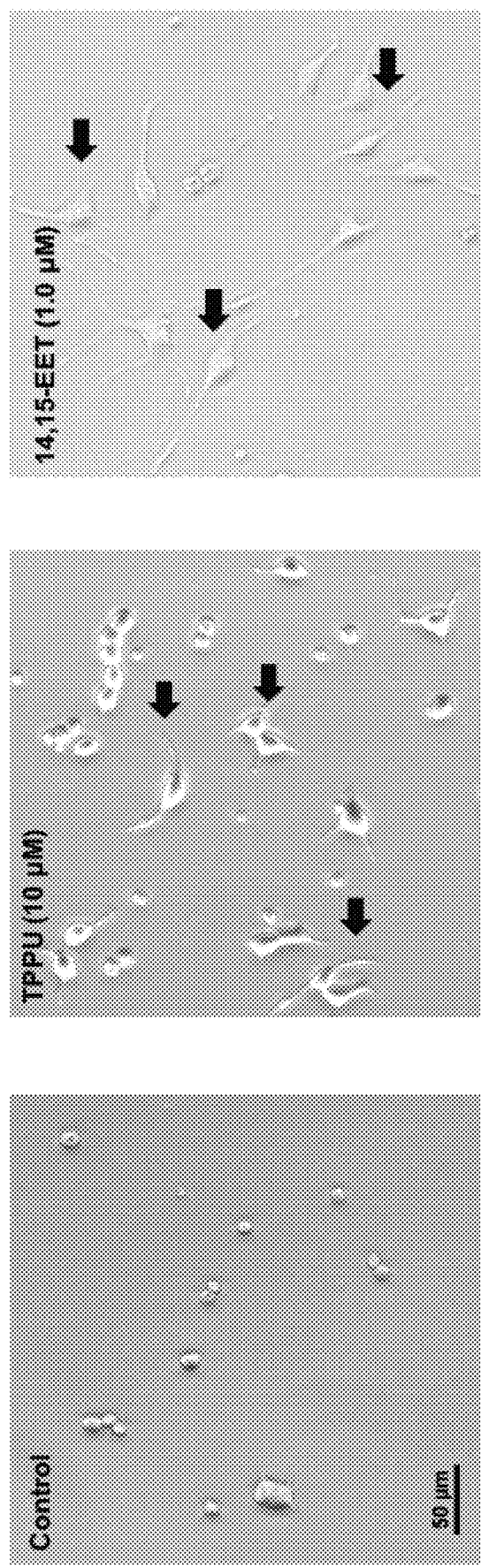

Depression is a severe and chronic psychiatric disease, affecting 350 million subjects worldwide. Although multiple antidepressants have been used in the treatment of depressive symptoms, their beneficial effects are limited. The soluble epoxide hydrolase (sEH) plays a key role in the inflammation which is involved in depression and other disorders of the central nervous system. Thus, we examined here the role of sEH in depression. In both inflammation and social defeat stress models of depression, a potent sEH inhibitor TPPU displayed rapid antidepressant effects. Expression of sEH protein in the brain from chronically stressed (susceptible) mice was higher than of control mice. Furthermore, expression of sEH protein in postmortem brain samples of patients with psychiatric diseases, including depression, bipolar disorder, and schizophrenia, was higher than controls. This is consistent with the conclusion that increased sEH levels are involved in the pathogenesis of certain psychiatric diseases. In support of this hypothesis, pretreatment with TPPU prevented the onset of depression-like behaviors after inflammation or repeated social defeat stress. Moreover, sEH knock-out (KO) mice did not show depression-like behavior after repeated social defeat stress, demonstrating stress resilience. The sEH KO mice showed increased brain-derived neurotrophic factor (BDNF) and phosphorylation of its receptor TrkB in the prefrontal cortex (PFC), hippocampus, but not the nucleus accumbens, showing that increased BDNF-TrkB signaling in the PFC and hippocampus confer stress resilience. All these findings are consistent with the conclusion that sEH plays a key role in the pathophysiology of depression, and that epoxy fatty acids, their mimics as well as sEH inhibitors could be potential therapeutic or prophylactic drugs for depression.

Accordingly, the present methods are based, in part, on the discovery that soluble epoxide hydrolase inhibitors have been shown to block the development and reverse the symptoms of severe depression in three different murine models. The target enzyme has been shown to be at high levels in human samples from psychiatric diseases including depression, bipolar disorder and schizophrenia. Interestingly, the levels are only elevated over normal brain in regions of the brain associated with these diseases. The increased target enzyme in human postmortum samples and treatment of depressed animals with soluble epoxide hydrolase inhibitors (or the use of sEH knock out mice) is associated with molecular markers associated with psychiatric disease.

2. Subjects Who May Benefit—Conditions Subject to Treatment

Subjects who may benefit generally have a neuropsychiatric disorder with depressive symptoms. Illustrative disorders include without limitation depression, major depression, schizophrenia, bipolar disorder, post-traumatic disorder (PTSD), eating disorder, substance abuse, drug addiction, drug dependency, social anxiety, Alzheimer's disease, cognitive decline, mild cognitive impairment, dementia, and attention-deficit hyperactivity disorder (ADHD). Without being bound to theory, it has been discovered that inhibitors of soluble epoxide hydrolase and other agents that increase the levels of epoxy-fatty acids increase levels of epoxyeicosantrienoic acids (EETs) and epoxydocosapentaenoic acids (EDPs), and related compounds, which in turn decrease dopamine release and decrease symptoms associated with neuropsychiatric disorders, including depression and addictive potential. The symptoms may be actively manifesting, or may be suppressed or controlled (e.g., by medication) or in remission. The subject may or may not have been diagnosed with the disorder, e.g., by a qualified medical or psychiatric practitioner or psychologist. In varying embodiments, the subject is already receiving a treatment regime for the neuropsychiatric disorder, e.g., taking a regime of antidepressants, antipsychotics, anxiolytics, and/or mood stabilizers.

Qualitative and quantitative measures of symptoms and behaviors of neuropsychiatric illnesses, including those listed above, are known in the art, and described, e.g., in the Diagnostic and Statistical Manual of Mental Disorders, 5th Edition (DSM-5) American Psychiatric Association, American Psychiatric Publishing, 2013 and/or the International Statistical Classification of Diseases and Related Health Problems (ICD)-11 of the World Health Organization (WHO) (available online at http://www.who.int/classifications/icd/en/). Symptoms for patients with psychiatric disorders can be measured and quantified using appropriate tests and scales established in the art, e.g., HAMD (Hamilton Depression Rating Scale) (Williams, *Arch Gen Psychiatry*. 1988 August; 45(8):742-7 and Zimmerman, et al., *J Affect Disord*. 2013 Sep. 5; 150(2):384-8), HAMA (Hamilton Anxiety Rating Scale) (Bruss, et al., *Psychiatry Res.* 1994 August; 53(2):191-202), YMRS (Young Mania Rating Scale) (Lukasiewicz, et al., *Int J Methods Psychiatr Res.* 2013 March; 22(1):46-58), BPRS (Brief Psychiatric Rating Scale) (Bell, et al., *J Nerv Ment Dis.* 1992 November; 180(11):723-8 and Lachar, et al., *J Am Acad Child Adolesc Psychiatry.* 2001 March; 40(3):333-40), PANSS (Positive and Negative Syndrome Scale) (Kay, et al., *Schizophr Bull.* 1987; 13(2):261-76 and Kay, et al., *Psychiatry Res.* 1988 January; 23(1):99-110), and/or CGS-I (Clinical Global Impression—Severity) (Pinna, et al., *Ann Gen Psychiatry.* 2015 Feb. 13; 14:6).

In varying embodiments, the subject is a child, a juvenile or an adult. In varying embodiments, the subject is a mammal, for example, a human or a domesticated mammal (e.g., a canine, a feline, an equine).

3. Agents that Increase Epoxy-Fatty Acids

Agents that increase epoxy-fatty acids include epoxy-fatty acids (e.g., including EETs), and inhibitors of soluble epoxide hydrolase (sEH).

a. Inhibitors of Soluble Epoxide Hydrolase (sEH)

Scores of sEH inhibitors are known, of a variety of chemical structures. Derivatives in which the urea, carbamate or amide pharmacophore are particularly useful as sEH inhibitors. As used herein, "pharmacophore" refers to the section of the structure of a ligand that binds to the sEH. In various embodiments, the urea, carbamate or amide pharmacophore is covalently bound to both an adamantane and to a 12 carbon chain dodecane. Derivatives that are metabolically stable are preferred, as they are expected to have greater activity in vivo. Selective and competitive inhibition of sEH in vitro by a variety of urea, carbamate, and amide derivatives is taught, for example, by Morisseau et al., Proc. Natl. Acad. Sci. U.S.A, 96:8849-8854 (1999), which provides substantial guidance on designing urea derivatives that inhibit the enzyme.

Derivatives of urea are transition state mimetics that form a preferred group of sEH inhibitors. Within this group, N,N'-dodecyl-cyclohexyl urea (DCU), is preferred as an inhibitor, while N-cyclohexyl-N'-dodecylurea (CDU) is particularly preferred. Some compounds, such as dicyclohexylcarbodiimide (a lipophilic diimide), can decompose to an active urea inhibitor such as DCU. Any particular urea derivative or other compound can be easily tested for its ability to inhibit sEH by standard assays, such as those discussed herein. The production and testing of urea and carbamate derivatives as sEH inhibitors is set forth in detail in, for example, Morisseau et al., Proc Natl Acad Sci (USA) 96:8849-8854 (1999).

N-Adamantyl-N'-dodecyl urea ("ADU") is both metabolically stable and has particularly high activity on sEH. (Both the 1- and the 2-admamantyl ureas have been tested and have about the same high activity as an inhibitor of sEH. Thus, isomers of adamantyl dodecyl urea are preferred inhibitors. It is further expected that N,N'-dodecyl-cyclohexyl urea (DCU), and other inhibitors of sEH, and particularly dodecanoic acid ester derivatives of urea, are suitable for use in the methods. Preferred inhibitors include without limitation:

12-(3-Adamantan-1-yl-ureido)dodecanoic acid (AUDA),

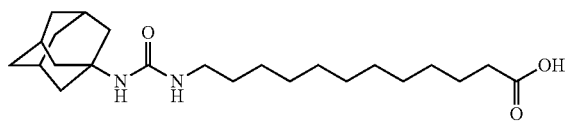 [SMILES: O=C(O)CCCCCCCCCCCNC(=O)NC12CC3CC(CC(C3)C1)C2]

12-(3-Adamantan-1-yl-ureido)dodecanoic acid butyl ester (AUDA-BE),

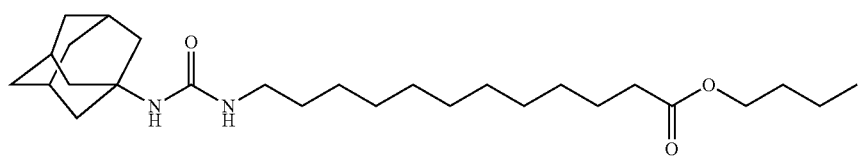 [SMILES: CCCCOC(=O)CCCCCCCCCCCNC(=O)NC12CC3CC(CC(C3)C1)C2]

Adamantan-1-yl-3-{5-[2-(2-ethoxyethoxy)ethoxy]pentyl}urea (compound 950, also referred to herein as "AEPU"), and

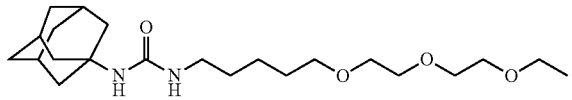 [SMILES: CCOCCOCCOCCCCCNC(=O)NC12CC3CC(CC(C3)C1)C2]

Another preferred group of inhibitors are piperidines. The following Tables sets forth some exemplar inhibitors of sEH and their ability to inhibit sEH activity of the human enzyme and sEH from equine, ovine, porcine, feline and canine, expressed as the amount needed to reduce the activity of the enzyme by 50% (expressed as "$IC_{50}$").

TABLE 1

IC$_{50}$ values for selected alkylpiperidine-based sEH inhibitors against human sEH

|  | | n = 0 | | n = 1 | |
| --- | --- | --- | --- | --- | --- |
| R: | | Compound | $IC_{50}$ (μM)$^a$ | Compound | $IC_{50}$ (μM)$^a$ |
| R: | H | I | 0.30 | II | 4.2 |
|  | (ethyl) | 3a | 3.8 | 4.a | 3.9 |
|  | (propyl) | 3b | 0.81 | 4b | 2.6 |
|  | (butyl) | 3c | 1.2 | 4c | 0.61 |
|  | (benzyl) | 3d | 0.01 | 4d | 0.11 |

$^a$As determined via a kinetic fluorescent assay.

TABLE 2 sEH inhibitors

| Structure | Name | sEHi # |
| --- | --- | --- |
| (3,4,4'-trichlorocarbanilide structure) | 3-(4-chlorophenyl)-1-(3,4-dichlorphenyl)urea or 3,4,4'-trichlorocarbanilide | 295 (TCC) |
| (adamantyl-ureido-dodecanoic acid structure) | 12-(3-adamantan-1-yl-ureido) dodecanoic acid | 700 (AUDA) |

TABLE 2-continued

| Structure | Name | sEHi # |
|---|---|---|
| | 1-adamantanyl-3-{5-[2-(2-ethoxyethoxy]pentyl]}urea | 950 (AEPU) |
| 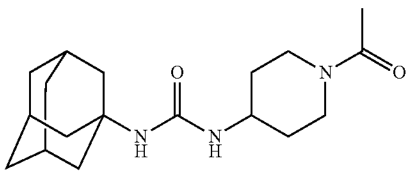 [SMILES: CC(=O)N1CCC(NC(=O)NC23CC4CC(CC(C4)C2)C3)CC1] | 1-(1-acetypiperidin-4-yl)-3-adamantanylurea | 1153 (APAU) |
| 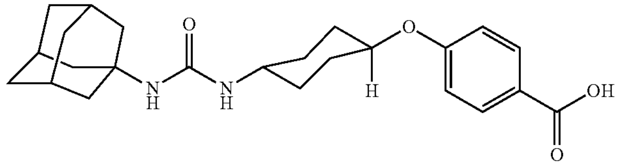 [SMILES: O=C(NC1CCC(Oc2ccc(C(=O)O)cc2)CC1)NC12CC3CC(CC(C3)C1)C2] | trans-4-[4-(3-Adamantan-1-yl-ureido)-cyclohexyloxy]-benzoic acid | 1471 (tAUCB) |
| 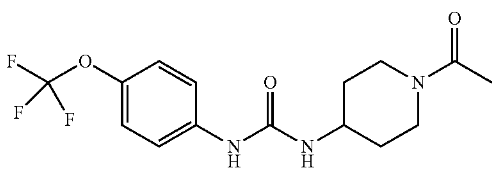 [SMILES: CC(=O)N1CCC(NC(=O)Nc2ccc(OC(F)(F)F)cc2)CC1] | 1-trifluoromethoxyphenyl-3-(1-acetylpiperidin-4-yl) urea | 1555 (TPAU) |
| 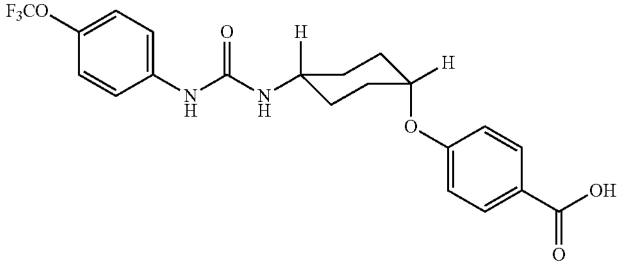 [SMILES: O=C(Nc1ccc(OC(F)(F)F)cc1)NC1CCC(Oc2ccc(C(=O)O)cc2)CC1] | cis-4-[4-(3-Adamantan-1-yl-ureido)-cyclohexyloxy]-benzoic acid | 1686 (cAUCB) |
| 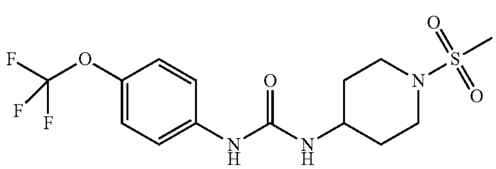 [SMILES: CS(=O)(=O)N1CCC(NC(=O)Nc2ccc(OC(F)(F)F)cc2)CC1] | 1-(1-methylsulfonyl-piperidin-4-yl)-3-(4-trifluoromethoxy-phenyl)-urea | 1709 (TUPS) |
| 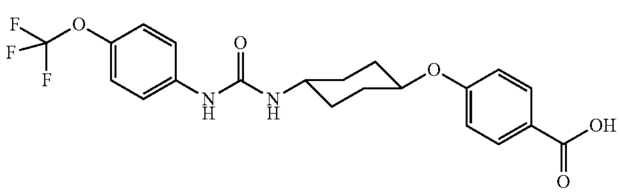 [SMILES: O=C(Nc1ccc(OC(F)(F)F)cc1)NC1CCC(Oc2ccc(C(=O)O)cc2)CC1] | trans-4-{4-[3-(4-Trifluoromethoxy-phenyl)-ureido]-cyclohexyloxy}-benzoic acid | 1728 (tTUCB) |
| 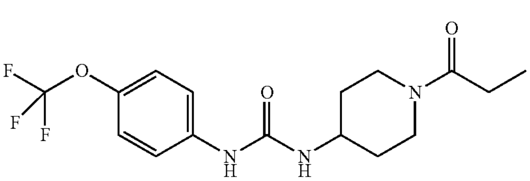 [SMILES: CCC(=O)N1CCC(NC(=O)Nc2ccc(OC(F)(F)F)cc2)CC1] | 1-trifluoromethoxyphenyl-3-(1-propionylpiperidin-4-yl) urea | 1770 (TPPU) |

TABLE 2-continued sEH inhibitors

| Structure | Name | sEHi # |
|---|---|---|
| 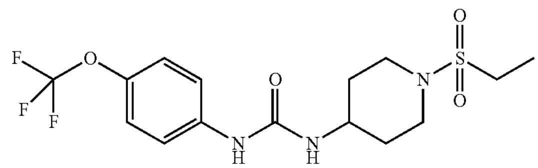 [SMILES: CCS(=O)(=O)N1CCC(NC(=O)Nc2ccc(OC(F)(F)F)cc2)CC1] | 1-(1-ethylsulfonyl-piperidin-4-yl)-3-(4-trifluoromethoxy-phenyl)-urea | 2213 (TUPSE) |
| 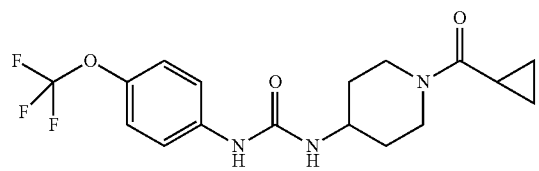 [SMILES: O=C(Nc1ccc(OC(F)(F)F)cc1)NC1CCN(C(=O)C2CC2)CC1] | 1-(1-(cyclopropanecarbonyl)piperidin-4-yl)-3-(4-(trifluoromethoxy)phenyl)urea | 2214 (CPTU) |
| 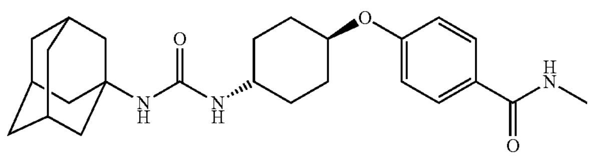 | trans-N-methyl-4-[4-(3-Adamantan-1-yl-ureido)-cyclohexyloxy]-benzamide | 2225 (tMAUCB) |
| 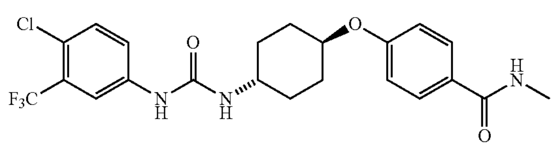 | trans-N-methyl-4-[4-((3-trifluoromethyl-4-chlorophenyl)-ureido)-cyclohexyloxy]-benzamide | 2226 (tMTCUCB) |
| 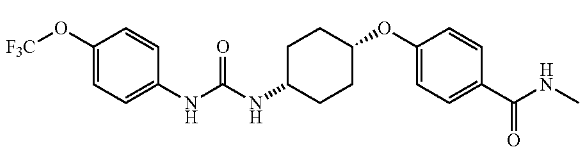 | cis-N-methyl-4-{4-[3-(4-trifluoromethoxy-phenyl)-ureido]-cyclohexyloxy}-benzamide | 2228 (cMTUCB) |
| 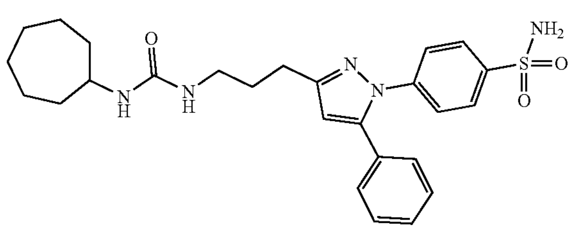 [SMILES: NS(=O)(=O)c1ccc(-n2nc(CCCNC(=O)NC3CCCCCC3)cc2-c2ccccc2)cc1] | 1-cycloheptyl-3-(3-(1,5-diphenyl-1H-pyrazol-3-yl)propyl)urea | 2247 (HDP3U) |

A number of other sEH inhibitors which can be used in the methods and compositions are described in published International Applications PCT/US2015/023048, PCT/US2013/024396, PCT/US2012/025074, PCT/US2011/064474, PCT/US2011/022901, PCT/US2008/072199, PCT/US2007/006412, PCT/US2005/038282, PCT/US2005/08765, PCT/US2004/010298 and U.S. Published Patent Application Publication Nos: 2016/0200683, 2015/0011586, 2014/0088156, 2014/0038923, 2013/0274476, 2013/0143925, 2013/0137726, 2011/0098322, 2005/0026844, each of which is hereby incorporated herein by reference in its entirety for all purposes.

In some embodiments, the sEH inhibitor is selected from the compounds disclosed in Table 2.1, below.

TABLE 2.1
sEH Inhibitors (physical properties and potency against human sEH)
| Structure and Compound No. | Mol. Weight | Exp/ logP[a] | Cal log P[b] | Ki (nM) (human sEH) | t$_{1/2}$ (min) (human sEH) |
|---|---|---|---|---|---|
| 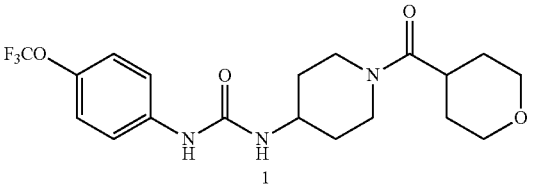 1 | 415.11 | 3.26 | 0.6 | 1.4 ± 0.01 | 14 |
| 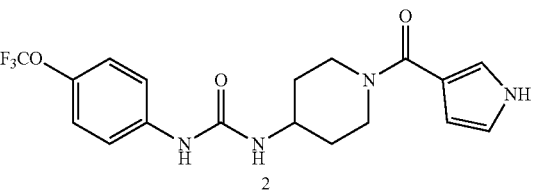 2 | 396.14 | 3.34 | 1.8 | 0.64 ± 0.17 | 15 |
| 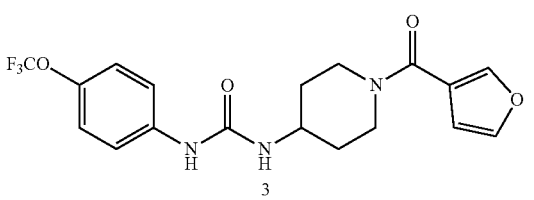 3 | 397.12 | 3.63 | 2.0 | 0.33 ± 0.34 | 17 |
| 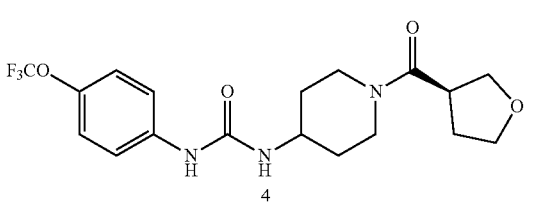 4 | 401.16 | 3.38 | 1.4 | 1.41 ± 0.11 | 17 |
| 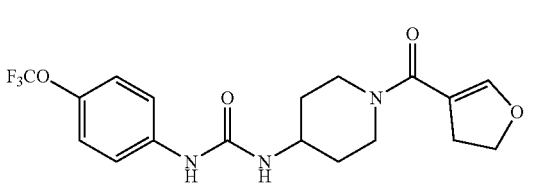 [SMILES: O=C(Nc1ccc(OC(F)(F)F)cc1)NC1CCN(C(=O)C2=COCC2)CC1] 5 | 399.14 | 3.49 | 2.6 | 0.77 ± 0.02 | 13 |
| 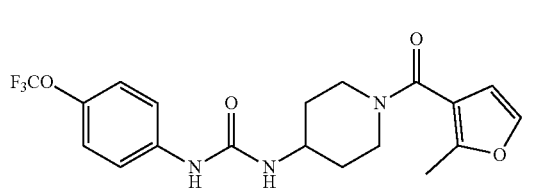 [SMILES: Cc1occc1C(=O)N1CCC(NC(=O)Nc2ccc(OC(F)(F)F)cc2)CC1] 6 | 411.14 | 4.30 | 2.5 | 0.55 ± 0.06 | 15 |
| 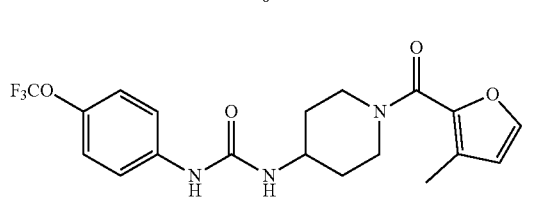 7 | 411.14 | 4.48 | 2.5 | 0.26 ± 0.11 | 21 |

TABLE 2.1-continued
sEH Inhibitors (physical properties and potency against human sEH)
| Structure and Compound No. | Mol. Weight | Exp/ logP[a] | Cal log P[b] | Ki (nM) (human sEH) | t$_{1/2}$ (min) (human sEH) |
|---|---|---|---|---|---|
| 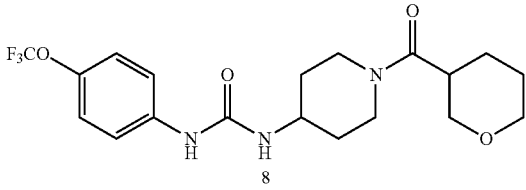 8 | 415.17 | 3.42 | 1.8 | 1.99 ± 0.23 | 13 |
| 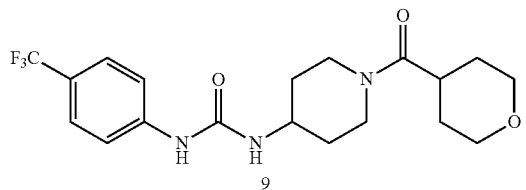 9 | 399.18 | 3.16 | 0.8 | 1.73 ± 0.01 | 11 |
| 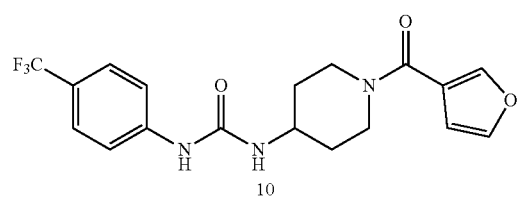 10 | 381.13 | 3.5 | 1.6 | 1.21 ± 0.2 | 11 |
| 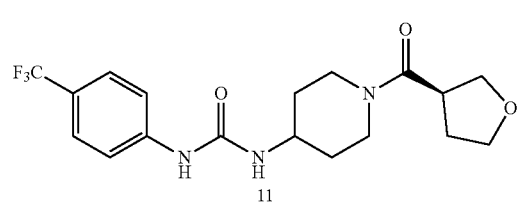 11 | 385.16 | 3.27 | 2.2 | 1.19 ± 0.08 | 13 |
| 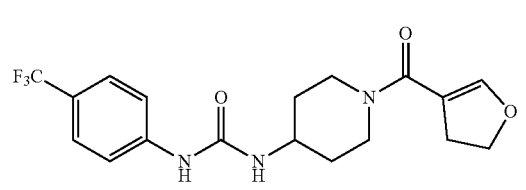 [SMILES: O=C(Nc1ccc(C(F)(F)F)cc1)NC1CCN(C(=O)C2=COCC2)CC1] 12 | 383.15 | 3.37 | 2.8 | 1.03 ± 0.20 | 8 |
| 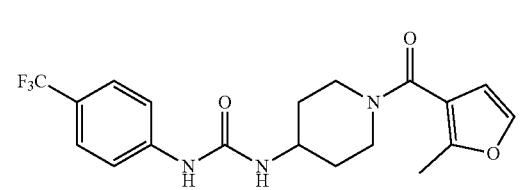 [SMILES: Cc1occc1C(=O)N1CCC(NC(=O)Nc2ccc(C(F)(F)F)cc2)CC1] 13 | 395.15 | 4.19 | 2.7 | 0.51 ± 0.03 | 11 |
| 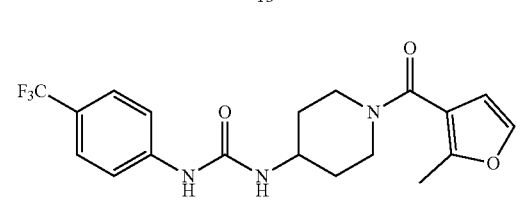 14 | 395.15 | 4.29 | 2.7 | 0.22 ± 0.01 | 15 |

TABLE 2.1-continued
sEH Inhibitors (physical properties and potency against human sEH)
| Structure and Compound No. | Mol. Weight | Exp/ logP[a] | Cal log P[b] | Ki (nM) (human sEH) | t$_{1/2}$ (min) (human sEH) |
|---|---|---|---|---|---|
| 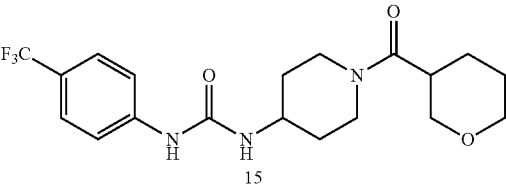 15 | 399.18 | 3.41 | 2.0 | 2.40 ± 0.08 | 11 |
| 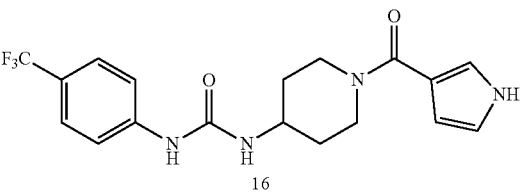 16 | 380.15 | 3.26 | 2.0 | 0.50 ± 0.01 | 10 |
| 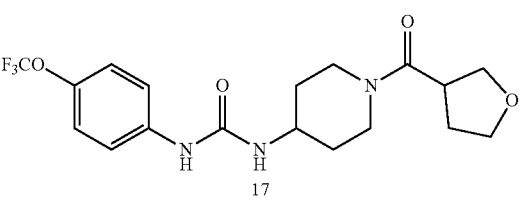 17 | 401.16 | 3.22 | 1.4 | 1.70 ± 0.01 | 12 |
| 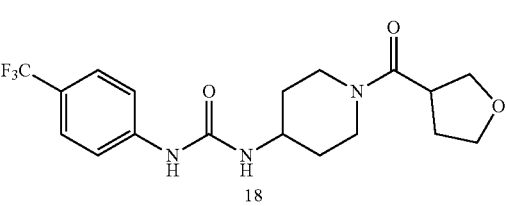 18 | 385.16 | 3.16 | 1.6 | 1.74 ± 0.11 | 10 |
| 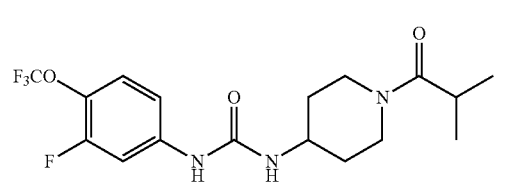 [SMILES: CC(C)C(=O)N1CCC(NC(=O)Nc2ccc(OC(F)(F)F)c(F)c2)CC1] 19 | 391.15 | 4.73 | 2.0 | 0.31 ± 0.01 | 22 |
| 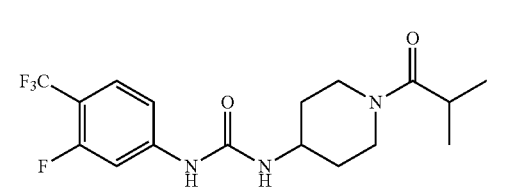 [SMILES: CC(C)C(=O)N1CCC(NC(=O)Nc2ccc(C(F)(F)F)c(F)c2)CC1] 20 | 375.16 | 4.40 | 2.3 | 0.49 ± 0.4 | 12 |
| 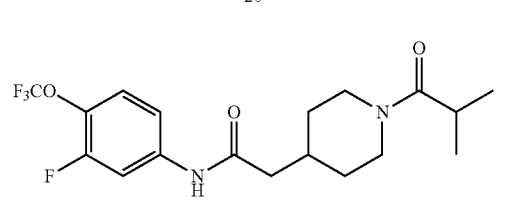 21 | 390.38 | 5.81 | 2.6 | 4.72 ± 0.70 | 3.4 |

TABLE 2.1-continued
sEH Inhibitors (physical properties and potency against human sEH)
| Structure and Compound No. | Mol. Weight | Exp/ logP[a] | Cal log P[b] | Ki (nM) (human sEH) | t₁/₂ (min) (human sEH) |
|---|---|---|---|---|---|
| 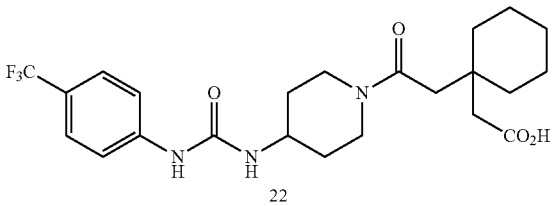 22 | 469.22 | — | — | 10.2 ± 1.1 | — |
| 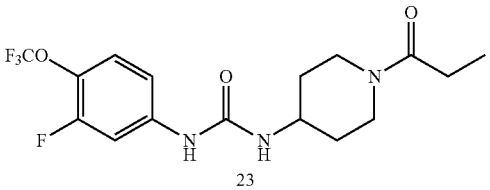 23 | 377.34 | 4.00 | 1.7 | 0.87 ± 0.13 | 11 |
| 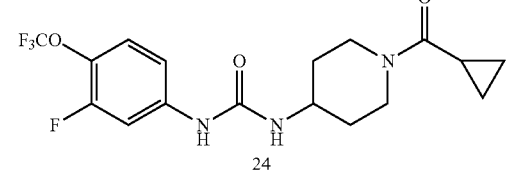 24 | 389.35 | 4.19 | 1.7 | 0.15 ± 0.04 | 19 |
| 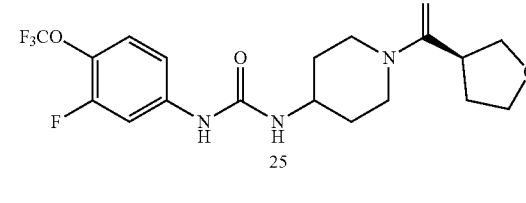 25 | 419.38 | 3.59 | 1.6 | 0.70 ± 0.01 | 13 |
| 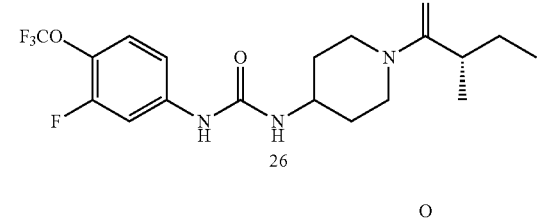 26 | 405.39 | 4.16 | 2.5 | <0.05 | 22 |
| 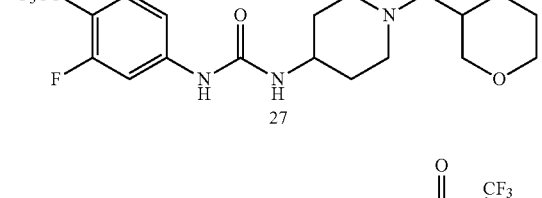 27 | 433.40 | 4.09 | 2.0 | 0.78 ± 0.19 | 12 |
| 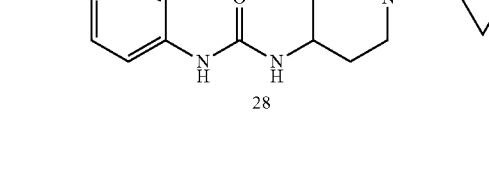 28 | 439.36 | 4.63 | 2.0 | 0.05 ± 0.04 | 24 |

TABLE 2.1-continued
sEH Inhibitors (physical properties and potency against human sEH)
| Structure and Compound No. | Mol. Weight | Exp/ logP[a] | Cal log P[b] | Ki (nM) (human sEH) | t$_{1/2}$ (min) (human sEH) |
|---|---|---|---|---|---|
| 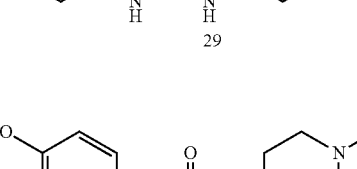 29 | 433.4 | 3.73 | 0.8 | 0.75 ± 0.05 | 11 |
| 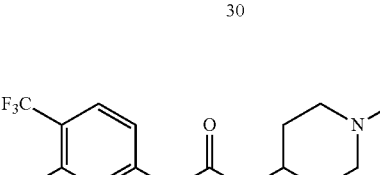 30 | 457.35 | 5.94 | 2.0 | <0.05 | 18 |
| 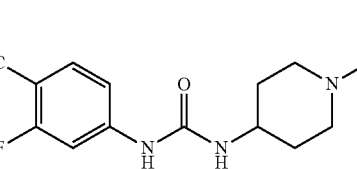 31 | 361.33 | 3.76 | 1.9 | 2.94± | 0.01 |
| 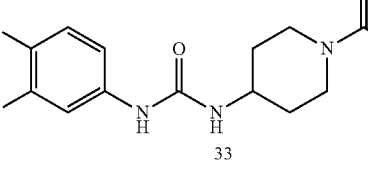 32 | 389.34 | 3.94 | 2.0 | 0.38 ± 0.08 | 8.2 |
| 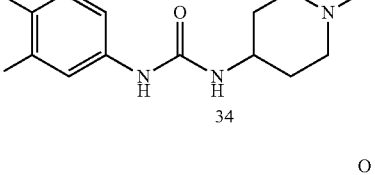 33 | 403.37 | 3.41 | 1.9 | 2.09 ± 0.24 | 5.3 |
| 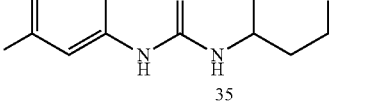 34 | 389.39 | 5.48 | 2.8 | 0.37 ± 0.03 | 13 |
|  35 | 417.40 | 3.84 | 2.3 | 2.66 ± 0.19 | 6.8 |

TABLE 2.1-continued
sEH Inhibitors (physical properties and potency against human sEH)
| Structure and Compound No. | Mol. Weight | Exp/ logP[a] | Cal log P[b] | Ki (nM) (human sEH) | t$_{1/2}$ (min) (human sEH) |
|---|---|---|---|---|---|
| 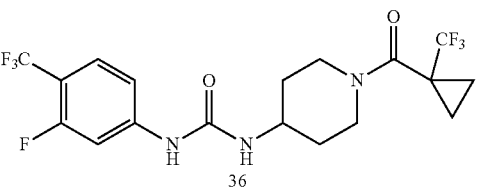 36 | 441.34 | 5.52 | 2.5 | 0.08 ± 0.01 | 21 |
| 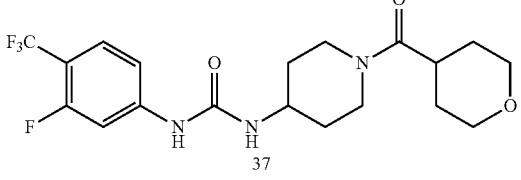 37 | 417.40 | 3.52 | 1.1 | 3.83 ± 0.41 | 6.9 |
| 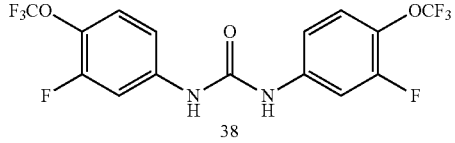 38 | 416.23 | ND | ND | 1.95 ± 0.30 | ND |
| 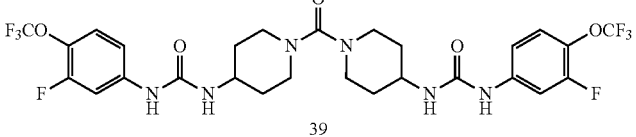 39 | 668.50 | ND | ND | 10.1 ± 1.8 | ND |
| 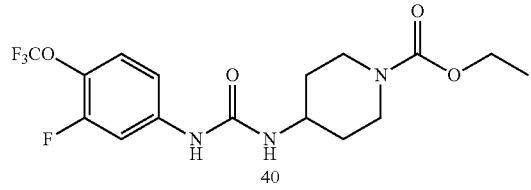 40 | 393.34 | 5.94 | 3.3 | <0.05 | 18 |
| 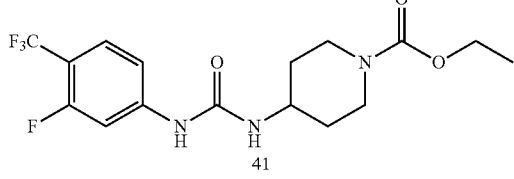 41 | 3.77.34 | 5.46 | 3.6 | 0.38 ± 0.03 | 7.6 |
| 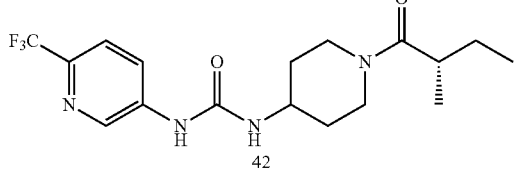 42 | 372.39 | 3.22 | 1.7 | 45.0 ± 2.3 | 3.7 |
| 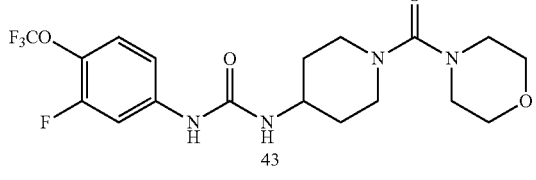 43 | 434.39 | 3.93 | 2.6 | 0.70 ± 0.06 | 15 |

TABLE 2.1-continued sEH Inhibitors (physical properties and potency against human sEH)

| Structure and Compound No. | Mol. Weight | Exp/ logP[a] | Cal log P[b] | Ki (nM) (human sEH) | $t_{1/2}$ (min) (human sEH) |
|---|---|---|---|---|---|
| 44 | 421.85 | 7.70 | 3.0 | 3.35 ± 0.42 | 10 |
| 45 | 465.29 | 8.07 | 3.2 | 3.40 ± 1.38 | 9.3 |
| 46 | 455.40 | 9.02 | 3.7 | 9.91 ± 3.37 | 5.9 |
| 47 | 471.40 | 10.62 | 3.1 | 9.07 ± 0.36 | 11 |
| 48 | 388.36 | 5.11 | 2.3 | 6.60 ± 0.01 | 3.3 |
| 49 | 404.41 | 7.68 | 3.1 | 3.14 ± 0.70 | 4.5 |
| 51 | 405.39 | ND | 2.5 | 0.06 ± 0.01 | ND |

TABLE 2.1-continued sEH Inhibitors (physical properties and potency against human sEH)

| Structure and Compound No. | Mol. Weight | Exp/logP$^a$ | Cal log P$^b$ | Ki (nM) (human sEH) | $t_{1/2}$ (min) (human sEH) |
|---|---|---|---|---|---|
| 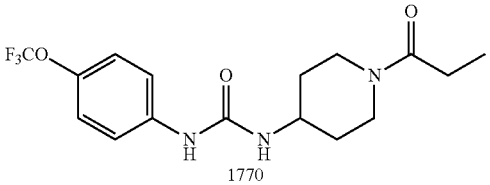 1770 | 359.34 | 3.23 | 1.50 | 0.91 ± 0.13 | 11 |
| 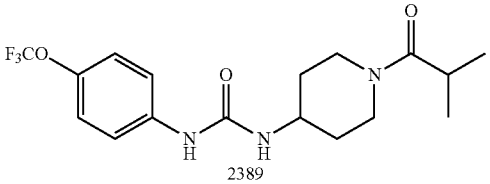 2389 | 357.37 | 3.37 | 2.00 | 0.66 ± 0.30 | 18 |
| 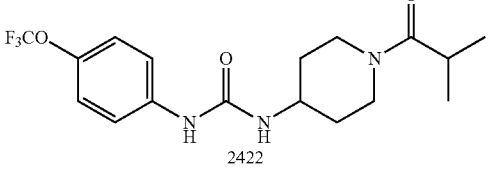 2422 | 373.37 | 3.56 | 1.81 | 0.31 ± 0.18 | 19 |
| 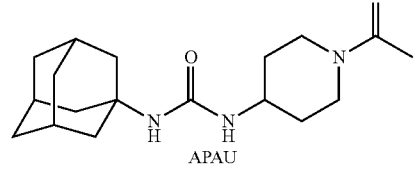 APAU | 319.44 | 1.5 | 0.8 | 19.5 ± 3.8 | 6 |

A further inhibitor of soluble epoxide hydrolase useful in the present methods is GSK2256294A (IUPAC/Chemical Name: (1R,3S)—N-(4-cyano-2-(trifluoromethyl)benzyl)-3-((4-methyl-6-(methylamino)-1,3,5-triazin-2-yl)amino)cyclohexane-1-carboxamide; CAS #: 1142090-23-0), described in Podolin, et al., *Prostaglandins Other Lipid Mediat.* (2013) 104-105:25-31, the structure of which is provided below:

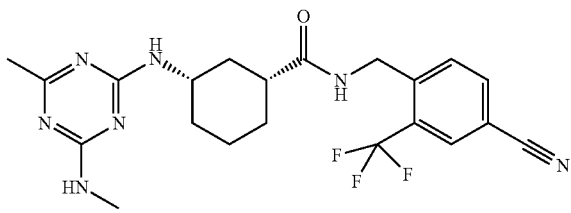 [SMILES: CNc1nc(C)nc(N[C@H]2CCC[C@@H](C(=O)NCc3ccc(C#N)cc3C(F)(F)F)C2)n1]

U.S. Pat. No. 5,955,496 (the '496 patent) also sets forth a number of sEH inhibitors which can be used in the methods. One category of these inhibitors comprises inhibitors that mimic the substrate for the enzyme. The lipid alkoxides (e.g., the 9-methoxide of stearic acid) are an exemplar of this group of inhibitors. In addition to the inhibitors discussed in the '496 patent, a dozen or more lipid alkoxides have been tested as sEH inhibitors, including the methyl, ethyl, and propyl alkoxides of oleic acid (also known as stearic acid alkoxides), linoleic acid, and arachidonic acid, and all have been found to act as inhibitors of sEH.

In another group of embodiments, the '496 patent sets forth sEH inhibitors that provide alternate substrates for the enzyme that are turned over slowly. Exemplars of this category of inhibitors are phenyl glycidols (e.g., S,S-4-nitrophenylglycidol), and chalcone oxides. The '496 patent notes that suitable chalcone oxides include 4-phenylchalcone oxide and 4-fluourochalcone oxide. The phenyl glycidols and chalcone oxides are believed to form stable acyl enzymes.

Additional inhibitors of sEH suitable for use in the methods are set forth in U.S. Pat. No. 6,150,415 (the '415 patent) and U.S. Pat. No. 6,531,506 (the '506 patent). Two preferred classes of sEH inhibitors are compounds of Formulas 1 and 2, as described in the '415 and '506 patents. Means for preparing such compounds and assaying desired compounds for the ability to inhibit epoxide hydrolases are also described. The '506 patent, in particular, teaches scores of inhibitors of Formula 1 and some twenty sEH inhibitors of Formula 2, which were shown to inhibit human sEH at concentrations as low as 0.1 μM. Any particular sEH inhibitor can readily be tested to determine whether it will work in the methods by standard assays. Esters and salts of the various compounds discussed above or in the cited patents, for example, can be readily tested by these assays for their use in the methods.

As noted above, chalcone oxides can serve as an alternate substrate for the enzyme. While chalcone oxides have half-lives which depend in part on the particular structure, as a group the chalcone oxides tend to have relatively short half-lives (a drug's half-life is usually defined as the time for the concentration of the drug to drop to half its original value. See, e.g., Thomas, G., Medicinal Chemistry: an introduction, John Wiley & Sons Ltd. (West Sussex, England, 2000)). Since the various uses contemplate inhibition of sEH over differing periods of time which can be measured in days, weeks, or months, chalcone oxides, and other inhibitors which have a half-life whose duration is shorter than the practitioner deems desirable, are preferably administered in a manner which provides the agent over a period of time. For example, the inhibitor can be provided in materials that release the inhibitor slowly. Methods of administration that permit high local concentrations of an inhibitor over a period of time are known, and are not limited to use with inhibitors which have short half-lives although, for inhibitors with a relatively short half-life, they are a preferred method of administration.

In addition to the compounds in Formula 1 of the '506 patent, which interact with the enzyme in a reversible fashion based on the inhibitor mimicking an enzyme-substrate transition state or reaction intermediate, one can have compounds that are irreversible inhibitors of the enzyme. The active structures such as those in the Tables or Formula 1 of the '506 patent can direct the inhibitor to the enzyme where a reactive functionality in the enzyme catalytic site can form a covalent bond with the inhibitor. One group of molecules which could interact like this would have a leaving group such as a halogen or tosylate which could be attacked in an SN2 manner with a lysine or histidine. Alternatively, the reactive functionality could be an epoxide or Michael acceptor such as an $\alpha/\beta$-unsaturated ester, aldehyde, ketone, ester, or nitrile.

Further, in addition to the Formula 1 compounds, active derivatives can be designed for practicing the invention. For example, dicyclohexyl thio urea can be oxidized to dicyclohexylcarbodiimide which, with enzyme or aqueous acid (physiological saline), will form an active dicyclohexylurea. Alternatively, the acidic protons on carbamates or ureas can be replaced with a variety of substituents which, upon oxidation, hydrolysis or attack by a nucleophile such as glutathione, will yield the corresponding parent structure. These materials are known as prodrugs or protoxins (Gilman et al., The Pharmacological Basis of Therapeutics, 7th Edition, MacMillan Publishing Company, New York, p. 16 (1985)) Esters, for example, are common prodrugs which are released to give the corresponding alcohols and acids enzymatically (Yoshigae et al., Chirality, 9:661-666 (1997)). The drugs and prodrugs can be chiral for greater specificity. These derivatives have been extensively used in medicinal and agricultural chemistry to alter the pharmacological properties of the compounds such as enhancing water solubility, improving formulation chemistry, altering tissue targeting, altering volume of distribution, and altering penetration. They also have been used to alter toxicology profiles.

There are many prodrugs possible, but replacement of one or both of the two active hydrogens in the ureas described here or the single active hydrogen present in carbamates is particularly attractive. Such derivatives have been extensively described by Fukuto and associates. These derivatives have been extensively described and are commonly used in agricultural and medicinal chemistry to alter the pharmacological properties of the compounds. (Black et al., Journal of Agricultural and Food Chemistry, 21(5):747-751 (1973); Fahmy et al, Journal of Agricultural and Food Chemistry, 26(3):550-556 (1978); Jojima et al., Journal of Agricultural and Food Chemistry, 31(3):613-620 (1983); and Fahmy et al., Journal of Agricultural and Food Chemistry, 29(3):567-572 (1981).)

Such active proinhibitor derivatives are within the scope of the present invention, and the just-cited references are incorporated herein by reference. Without being bound by theory, it is believed that suitable inhibitors mimic the enzyme transition state so that there is a stable interaction with the enzyme catalytic site. The inhibitors appear to form hydrogen bonds with the nucleophilic carboxylic acid and a polarizing tyrosine of the catalytic site.

In some embodiments, the sEH inhibitor used in the methods taught herein is a "soft drug." Soft drugs are compounds of biological activity that are rapidly inactivated by enzymes as they move from a chosen target site. EETs and simple biodegradable derivatives administered to an area of interest may be considered to be soft drugs in that they are likely to be enzymatically degraded by sEH as they diffuse away from the site of interest following administration. Some sEHI, however, may diffuse or be transported following administration to regions where their activity in inhibiting sEH may not be desired. Thus, multiple soft drugs for treatment have been prepared. These include but are not limited to carbamates, esters, carbonates and amides placed in the sEHI, approximately 7.5 angstroms from the carbonyl of the central pharmacophore. These are highly active sEHI that yield biologically inactive metabolites by the action of esterase and/or amidase. Groups such as amides and carbamates on the central pharmacophores can also be used to increase solubility for applications in which that is desirable in forming a soft drug. Similarly, easily metabolized ethers may contribute soft drug properties and also increase the solubility.

In some embodiments, sEH inhibition can include the reduction of the amount of sEH. As used herein, therefore, sEH inhibitors can therefore encompass nucleic acids that inhibit expression of a gene encoding sEH. Many methods of reducing the expression of genes, such as reduction of transcription and siRNA, are known, and are discussed in more detail below.

In various embodiments, a compound with combined functionality to concurrently inhibit sEH and COX-2 is administered. Urea-containing pyrazoles that function as dual inhibitors of cyclooxygenase-2 and soluble epoxide hydrolase are described, e.g., in Hwang, et al., *J Med Chem.* (2011) 28; 54(8):3037-50.

Preferably, the inhibitor inhibits sEH without also significantly inhibiting microsomal epoxide hydrolase ("mEH"). Preferably, at concentrations of 100 µM, the inhibitor inhibits sEH activity by at least 50% while not inhibiting mEH activity by more than 10%. Preferred compounds have an $IC_{50}$ (inhibition potency or, by definition, the concentration of inhibitor which reduces enzyme activity by 50%) of less than about 100 µM. Inhibitors with $IC_{50}$s of less than 100 µM are preferred, with $IC_{50}$s of less than 75 µM being more preferred and, in order of increasing preference, an $IC_{50}$ of 50 µM, 40 µM, 30 µM, 25 µM, 20 µM, 15 µM, 10 µM, 5 µM, 3 µM, 2 µM, 1 µM, 100 nM, 10 nM, 1.0 nM, or even less, being still more preferred. Assays for determining sEH activity are known in the art and described elsewhere herein. The $IC_{50}$ determination of the inhibitor can be made with respect to an sEH enzyme from the species subject to treatment (e.g., the subject receiving the inhibitor of sEH).

b. Cis-epoxyeicosantrienoic Acids ("EETs"), Epoxyeicosatetraenoic Acids (EEQs) and Epoxydocosapentaenoic Acids (EDPs)

EETs, which are epoxides of arachidonic acid, are known to be effectors of blood pressure, regulators of inflammation, and modulators of vascular permeability. Hydrolysis of the epoxides by sEH diminishes this activity. Inhibition of sEH raises the level of EETs since the rate at which the EETs are hydrolyzed into dihydroxyeicosatrienoic acids ("DHETs") is reduced.

It has long been believed that EETs administered systemically would be hydrolyzed too quickly by endogenous sEH to be helpful. For example, in one prior report of EETs administration, EETs were administered by catheters inserted into mouse aortas. The EETs were infused continuously during the course of the experiment because of concerns over the short half-life of the EETs. See, Liao and Zeldin, International Publication WO 01/10438 (hereafter "Liao and Zeldin"). It also was not known whether endogenous sEH could be inhibited sufficiently in body tissues to permit administration of exogenous EET to result in increased levels of EETs over those normally present. Further, it was thought that EETs, as epoxides, would be too labile to survive the storage and handling necessary for therapeutic use.

Studies from the laboratory of the present inventors, however, showed that systemic administration of EETs in conjunction with inhibitors of sEH had better results than did administration of sEH inhibitors alone. EETs were not administered by themselves in these studies since it was anticipated they would be degraded too quickly to have a useful effect. Additional studies from the laboratory of the present inventors have since shown, however, that administration of EETs by themselves has had therapeutic effect. Without wishing to be bound by theory, it is surmised that the exogenous EET overwhelms endogenous sEH, and allows EETs levels to be increased for a sufficient period of time to have therapeutic effect. Thus, EETs can be administered without also administering an sEHI to provide a therapeutic effect. Moreover, EETs, if not exposed to acidic conditions or to sEH are stable and can withstand reasonable storage, handling and administration.

In short, sEHI, EETs, EEQs and EDPs, or co-administration of sEHIs and one or more of EETs, EEQs and EDPs, can be used in the present methods. In some embodiments, one or more EETs, EEQs and/or EDPs are administered to the patient without also administering an sEHI. In some embodiments, one or more EETs, EEQs and/or EDPs are administered shortly before or concurrently with administration of an sEH inhibitor to slow hydrolysis of the EETs, EEQs and/or EDPs. In some embodiments, one or more EETs, EEQs and/or EDPs are administered after administration of an sEH inhibitor, but before the level of the sEHI has diminished below a level effective to slow the hydrolysis of the EETs, EEQs and/or EDPs.

EETs useful in the methods include 14,15-EET, 8,9-EET and 11,12-EET, and 5,6 EETs. Preferably, the EETs are administered as the methyl ester, which is more stable. Persons of skill will recognize that the EETs are regioisomers, such as 8S,9R- and 14R,15S-EET. 8,9-EET, 11,12-EET, and 14R,15S-EET, are commercially available from, for example, Sigma-Aldrich (catalog nos. E5516, E5641, and E5766, respectively, Sigma-Aldrich Corp., St. Louis, Mo.). EEQs of use for direct administration include without limitation 17,18-epoxyeicosatetraenoic acid (17,18-EEQ). EDPs of use for direct administration include without limitation 19,20-epoxydocosapentaenoic (19,20-EDP).

If desired, EETs, EEQs and/or EDPs, analogs, or derivatives that retain activity can be used in place of or in combination with unmodified EETs, EEQs and/or EDPs. EETs, EEQs and/or EDPs analogs are defined herein as compounds with structural substitutions or alterations in an EETs, EEQs and/or EDPs, and include structural analogs in which one or more EETs, EEQs and/or EDPs olefins are removed or replaced with acetylene or cyclopropane groups, analogs in which the epoxide moiety is replaced with oxitane or furan rings and heteroatom analogs. In other analogs, the epoxide moiety is replaced with ether, alkoxides, urea, amide, carbamate, difluorocycloprane, or carbonyl, while in others, the carboxylic acid moiety is stabilized by blocking beta oxidation or is replaced with a commonly used mimic, such as a nitrogen heterocycle, a sulfonamide, or another polar functionality. In some embodiments, olefins not critical for biological activity are removed and omega oxidation is reduced. In preferred forms, the analogs or derivatives are relatively stable as compared to an unmodified EETs, EEQs and/or EDPs because they are more resistant than an unmodified EETs, EEQs and/or EDPs to sEH and to chemical breakdown. "Relatively stable" means the rate of hydrolysis by sEH is at least 25% less than the hydrolysis of the unmodified EETs, EEQs and/or EDPs in a hydrolysis assay, and more preferably 50% or more lower than the rate of hydrolysis of an unmodified EETs, EEQs and/or EDPs. Liao and Zeldin show, for example, episulfide and sulfonamide EETs derivatives. In varying embodiments, amide and ester derivatives of EETs, EEQs and/or EDPs and that are relatively stable are administered. Whether or not a particular EETs, EEQs and/or EDPs analog or derivative has the biological activity of the unmodified EETs, EEQs and/or EDPs can be readily determined by using it in standard assays.

In some embodiments, the EETs, EEQs and/or EDPs are embedded or otherwise placed in a material that releases the EETs, EEQs and/or EDPs over time. Materials suitable for promoting the slow release of compositions such as EETs, EEQs and/or EDPs are known in the art. Optionally, one or more sEH inhibitors may also be placed in the slow release material.

Conveniently, the EETs, EEQs and/or EDPs can be administered orally. Since EETs are subject to degradation under acidic conditions, EETs intended for oral administration can be coated with a coating resistant to dissolving under acidic conditions, but which dissolve under the mildly basic conditions present in the intestines. Suitable coatings, commonly known as "enteric coatings" are widely used for products, such as aspirin, which cause gastric distress or which would undergo degradation upon exposure to gastric acid. By using coatings with an appropriate dissolution profile, the coated substance can be released in a chosen section of the intestinal tract. For example, a substance to be released in the colon is coated with a substance that dissolves at pH 6.5-7, while substances to be released in the duodenum can be coated with a coating that dissolves at pH values over 5.5. Such coatings are commercially available from, for example, Rohm Specialty Acrylics (Rohm America LLC, Piscataway, N.J.) under the trade name "Eudragit®". The choice of the particular enteric coating is not critical to the practice.

c. Phosphodiesterase Inhibitors (PDEi)

Phosphodiesterase inhibitors (PDEi) are well known anti-inflammatory agents. Many different classes of isozyme selective PDEi lead to remarkable increases in the plasma levels of a broad range of epoxy-fatty acids (EFA). The magnitude of this increase is so dramatic that PDEi can elevate epoxy-fatty acids as well as highly potent inhibitors of soluble epoxide hydrolase. Accordingly, levels of epoxy-fatty acids (e.g., in blood, plasma, serum) can be increased by administration of a phosphodiesterase inhibitor (PDEi).

The PDEi may or may not be selective, specific or preferential for cAMP. Exemplary PDEs that degrade cAMP include without limitation PDE3, PDE4, PDE7, PDE8 and PDE10. Exemplary cAMP selective hydrolases include PDE4, 7 and 8. Exemplary PDEs that hydrolyse both cAMP and cGMP include PDE1, PDE2, PDE3, PDE10 and PDE11. Isoenzymes and isoforms of PDEs are well known in the art. See, e.g., Boswell-Smith et al., Brit. J. Pharmacol. 147: S252-257 (2006), and Reneerkens, et al., Psychopharmacology (2009) 202:419-443, the contents of which are incorporated herein by reference.

In some embodiments, the PDE inhibitor is a non-selective inhibitor of PDE. Exemplary non-selective PDE inhibitors that find use include without limitation caffeine, theophylline, isobutylmethylxanthine, aminophylline, pentoxifylline, vasoactive intestinal peptide (VIP), secretin, adrenocorticotropic hormone, pilocarpine, alpha-melanocyte stimulating hormone (MSH), beta-MSH, gamma-MSH, the ionophore A23187, prostaglandin E1.

In some embodiments, the PDE inhibitor used specifically or preferentially inhibits PDE4. Exemplary inhibitors that selectively inhibit PDE4 include without limitation rolipram, roflumilast, cilomilast, ariflo, HT0712, ibudilast and mesembrine.

In some embodiments, the PDE inhibitor used specifically or preferentially inhibits a cAMP PDE, e.g., PDE4, PDE7 or PDE8. In some embodiments, the PDE inhibitor used inhibits a cAMP PDE, e.g., PDE1, PDE2, PDE3, PDE4, PDE7, PDE8, PDE10 or PDE11. Exemplary agents that inhibit a cAMP phosphodiesterase include without limitation rolipram, roflumilast, cilomilast, ariflo, HT0712, ibudilast, mesembrine, cilostamide, enoxamone, milrinone, siguazodan and BRL-50481.

In some embodiments, the PDE inhibitor used specifically inhibits PDE5. Exemplary inhibitors that selectively inhibit PDE5 include without limitation sildenafil, zaprinast, tadalafil, udenafil, avanafil and vardenafil.

d. Assays for Epoxide Hydrolase Activity

Any of a number of standard assays for determining epoxide hydrolase activity can be used to determine inhibition of sEH. For example, suitable assays are described in Gill, et al., Anal Biochem 131:273-282 (1983); and Borhan, et al., Analytical Biochemistry 231:188-200 (1995)). Suitable in vitro assays are described in Zeldin et al., J Biol. Chem. 268:6402-6407 (1993). Suitable in vivo assays are described in Zeldin et al., Arch Biochem Biophys 330:87-96 (1996). Assays for epoxide hydrolase using both putative natural substrates and surrogate substrates have been reviewed (see, Hammock, et al. In: Methods in Enzymology, Volume III, Steroids and Isoprenoids, Part B, (Law, J. H. and H. C. Rilling, eds. 1985), Academic Press, Orlando, Fla., pp. 303-311 and Wixtrom et al., In: Biochemical Pharmacology and Toxicology, Vol. 1: Methodological Aspects of Drug Metabolizing Enzymes, (Zakim, D. and D. A. Vessey, eds. 1985), John Wiley & Sons, Inc., New York, pp. 1-93. Several spectral based assays exist based on the reactivity or tendency of the resulting diol product to hydrogen bond (see, e.g., Wixtrom, supra, and Hammock. Anal. Biochem. 174: 291-299 (1985) and Dietze, et al. Anal. Biochem. 216:176-187 (1994)).

The enzyme also can be detected based on the binding of specific ligands to the catalytic site which either immobilize the enzyme or label it with a probe such as dansyl, fluorascein, luciferase, green fluorescent protein or other reagent. The enzyme can be assayed by its hydration of EETs, its hydrolysis of an epoxide to give a colored product as described by Dietze et al., 1994, supra, or its hydrolysis of a radioactive surrogate substrate (Borhan et al., 1995, supra). The enzyme also can be detected based on the generation of fluorescent products following the hydrolysis of the epoxide. Numerous methods of epoxide hydrolase detection have been described (see, e.g., Wixtrom, supra).

The assays are normally carried out with a recombinant enzyme following affinity purification. They can be carried out in crude tissue homogenates, cell culture or even in vivo, as known in the art and described in the references cited above.

e. Other Means of Inhibiting sEH Activity

Other means of inhibiting sEH activity or gene expression can also be used in the methods. For example, a nucleic acid molecule complementary to at least a portion of the human sEH gene can be used to inhibit sEH gene expression. Means for inhibiting gene expression using short RNA molecules, for example, are known. Among these are short interfering RNA (siRNA), small temporal RNAs (stRNAs), and micro-RNAs (miRNAs). Short interfering RNAs silence genes through a mRNA degradation pathway, while stRNAs and miRNAs are approximately 21 or 22 nt RNAs that are processed from endogenously encoded hairpin-structured precursors, and function to silence genes via translational repression. See, e.g., McManus et al., RNA, 8(6):842-50 (2002); Morris et al., Science, 305(5688):1289-92 (2004); He and Hannon, Nat Rev Genet. 5(7):522-31 (2004).

"RNA interference," a form of post-transcriptional gene silencing ("PTGS"), describes effects that result from the introduction of double-stranded RNA into cells (reviewed in Fire, A. Trends Genet 15:358-363 (1999); Sharp, P. Genes Dev 13:139-141 (1999); Hunter, C. Curr Biol 9:R440-R442 (1999); Baulcombe. D. Curr Biol 9:R599-R601 (1999); Vaucheret et al. Plant J 16: 651-659 (1998)). RNA interference, commonly referred to as RNAi, offers a way of specifically inactivating a cloned gene, and is a powerful tool for investigating gene function.

The active agent in RNAi is a long double-stranded (antiparallel duplex) RNA, with one of the strands corresponding or complementary to the RNA which is to be inhibited. The inhibited RNA is the target RNA. The long double stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo.

In mammalian cells other than these, however, longer RNA duplexes provoked a response known as "sequence non-specific RNA interference," characterized by the non-specific inhibition of protein synthesis.

Further studies showed this effect to be induced by dsRNA of greater than about 30 base pairs, apparently due to an interferon response. It is thought that dsRNA of greater than about 30 base pairs binds and activates the protein PKR and 2',5'-oligonucleotide synthetase (2',5'-AS). Activated PKR stalls translation by phosphorylation of the translation initiation factors eIF2α, and activated 2',5'-AS causes mRNA degradation by 2',5'-oligonucleotide-activated ribonuclease L. These responses are intrinsically sequence-nonspecific to the inducing dsRNA; they also frequently result in apoptosis, or cell death. Thus, most somatic mammalian cells undergo apoptosis when exposed to the concentrations of dsRNA that induce RNAi in lower eukaryotic cells.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. Nature 411: 494-498 (2001)). In this report, siRNA were applied to cultured cells by transfection in oligofectamine micelles. These RNA duplexes were too short to elicit sequence-nonspecific responses like apoptosis, yet they efficiently initiated RNAi. Many laboratories then tested the use of siRNA to knock out target genes in mammalian cells. The results demonstrated that siRNA works quite well in most instances.

For purposes of reducing the activity of sEH, siRNAs to the gene encoding sEH can be specifically designed using computer programs. The cloning, sequence, and accession numbers of the human sEH sequence are set forth in Beetham et al., Arch. Biochem. Biophys. 305(1):197-201 (1993). An exemplary amino acid sequence of human sEH (GenBank Accession No. L05779; SEQ ID NO:1) and an exemplary nucleotide sequence encoding that amino acid sequence (GenBank Accession No. AAA02756; SEQ ID NO:2) are set forth in U.S. Pat. No. 5,445,956. The nucleic acid sequence of human sEH is also published as GenBank Accession No. NM_001979.4; the amino acid sequence of human sEH is also published as GenBank Accession No. NP_001970.2.

A program, siDESIGN from Dharmacon, Inc. (Lafayette, Colo.), permits predicting siRNAs for any nucleic acid sequence, and is available on the World Wide Web at dharmacon.com. Programs for designing siRNAs are also available from others, including Genscript (available on the Web at genscript.com/ssl-bin/app/rnai) and, to academic and non-profit researchers, from the Whitehead Institute for Biomedical Research found on the worldwide web at "jura.wi.mit.edu/pubint/http://iona.wi.mit.edu/siRNAext/."

For example, using the program available from the Whitehead Institute, the following sEH target sequences and siRNA sequences can be generated:

```
1) Target:
                                        (SEQ ID NO: 3)
CAGTGTTCATTGGCCATGACTGG Sense-siRNA:
                                        (SEQ ID NO: 4)
5'-GUGUUCAUUGGCCAUGACUTT-3'

Antisense-siRNA:
                                        (SEQ ID NO: 5)
5'-AGUCAUGGCCAAUGAACACUTT-3'

2) Target:
                                        (SEQ ID NO: 6)
GAAAGGCTATGGAGAGTCATCTG Sense-siRNA:
                                        (SEQ ID NO: 7)
5'-AAGGCUAUGGAGAGUCAUCUTT-3'

Antisense-siRNA:
                                        (SEQ ID NO: 8)
5'-GAUGACUCUCCAUAGCCUUTT-3'

3) Target
                                        (SEQ ID NO: 9)
AAAGGCTATGGAGAGTCATCTGC
```

```
                    -continued
Sense-siRNA:
                                        (SEQ ID NO: 10)
5'-AGGCUAUGGAGAGUCAUCUTT-3'

Antisense-siRNA:
                                        (SEQ ID NO: 11)
5'-AGAUGACUCUCCAUAGCCUTT-3'

4) Target:
                                        (SEQ ID NO: 12)
CAAGCAGTGTTCATTGGCCATGA Sense-siRNA:
                                        (SEQ ID NO: 13)
5'-AGCAGUGUUCAUUGGCCAUTT-3'

Antisense-siRNA:
                                        (SEQ ID NO: 14)
5'-AUGGCCAAUGAACACUGCUTT-3'

5) Target:
                                        (SEQ ID NO: 15)
CAGCACATGGAGGACTGGATTCC Sense-siRNA:
                                        (SEQ ID NO: 16)
5'-GCACAUGGAGGACUGGAUUTT-3'

Antisense-siRNA:
                                        (SEQ ID NO: 17)
5'-AAUCCAGUCCUCCAUGUGCTT-3'
```

Alternatively, siRNA can be generated using kits which generate siRNA from the gene. For example, the "Dicer siRNA Generation" kit (catalog number T510001, Gene Therapy Systems, Inc., San Diego, Calif.) uses the recombinant human enzyme "dicer" in vitro to cleave long double stranded RNA into 22 bp siRNAs. By having a mixture of siRNAs, the kit permits a high degree of success in generating siRNAs that will reduce expression of the target gene. Similarly, the Silencer™ siRNA Cocktail Kit (RNase III) (catalog no. 1625, Ambion, Inc., Austin, Tex.) generates a mixture of siRNAs from dsRNA using RNase III instead of dicer. Like dicer, RNase III cleaves dsRNA into 12-30 bp dsRNA fragments with 2 to 3 nucleotide 3' overhangs, and 5'-phosphate and 3'-hydroxyl termini. According to the manufacturer, dsRNA is produced using T7 RNA polymerase, and reaction and purification components included in the kit. The dsRNA is then digested by RNase III to create a population of siRNAs. The kit includes reagents to synthesize long dsRNAs by in vitro transcription and to digest those dsRNAs into siRNA-like molecules using RNase III. The manufacturer indicates that the user need only supply a DNA template with opposing T7 phage polymerase promoters or two separate templates with promoters on opposite ends of the region to be transcribed.

The siRNAs can also be expressed from vectors. Typically, such vectors are administered in conjunction with a second vector encoding the corresponding complementary strand. Once expressed, the two strands anneal to each other and form the functional double stranded siRNA. One exemplar vector suitable for use in the invention is pSuper, available from OligoEngine, Inc. (Seattle, Wash.). In some embodiments, the vector contains two promoters, one positioned downstream of the first and in antiparallel orientation. The first promoter is transcribed in one direction, and the second in the direction antiparallel to the first, resulting in expression of the complementary strands. In yet another set of embodiments, the promoter is followed by a first segment encoding the first strand, and a second segment encoding the second strand. The second strand is complementary to the palindrome of the first strand. Between the first and the second strands is a section of RNA serving as a linker (sometimes called a "spacer") to permit the second strand to bend around and anneal to the first strand, in a configuration known as a "hairpin."

The formation of hairpin RNAs, including use of linker sections, is well known in the art. Typically, an siRNA expression cassette is employed, using a Polymerase III promoter such as human U6, mouse U6, or human H1. The coding sequence is typically a 19-nucleotide sense siRNA sequence linked to its reverse complementary antisense siRNA sequence by a short spacer. Nine-nucleotide spacers are typical, although other spacers can be designed. For example, the Ambion website indicates that its scientists have had success with the spacer TTCAAGAGA (SEQ ID NO:18). Further, 5-6 T's are often added to the 3' end of the oligonucleotide to serve as a termination site for Polymerase III. See also, Yu et al., Mol Ther 7(2):228-36 (2003); Matsukura et al., Nucleic Acids Res 31(15):e77 (2003).

As an example, the siRNA targets identified above can be targeted by hairpin siRNA as follows. To attack the same targets by short hairpin RNAs, produced by a vector (permanent RNAi effect), sense and antisense strand can be put in a row with a loop forming sequence in between and suitable sequences for an adequate expression vector to both ends of the sequence. The following are non-limiting examples of hairpin sequences that can be cloned into the pSuper vector:

```
1) Target:
                                    (SEQ ID NO: 19)
CAGTGTTCATTGGCCATGACTGG Sense strand:
                                    (SEQ ID NO: 20)
5'-GATCCCCGTGTTCATTGGCCATGACTTTCAA

GAGAAGTCATGGCCAATGAACACTTTTT-3'

Antisense strand:
                                    (SEQ ID NO: 21)
5'-AGCTAAAAAGTGTTCATTGGCCATGACTTCTCTT

GAAAGTCATGGCCAATGAACACGGG-3'

2) Target:
                                    (SEQ ID NO: 22)
GAAAGGCTATGGAGAGTCATCTG Sense strand:
                                    (SEQ ID NO: 23)
5'-GATCCCCAAGGCTATGGAGAGTCATCTTCAAGAGA

TGACTCTCCATAGCCTTTTTT-3'

Antisense strand:
                                    (SEQ ID NO: 24)
5'-AGCTAAAAAAGGCTATGGAGAGTCATCTCTCTTGAA

GATGACTCTCCATAGCCTTGGG-3'

3) Target:
                                    (SEQ ID NO: 25)
AAAGGCTATGGAGAGTCATCTGC Sense strand:
                                    (SEQ ID NO: 26)
5'-GATCCCCAGGCTATGGAGAGTCATCTTTCAAGAGAAG

ATGACTCTCCATAGCCTTTTTT-3'

Antisense strand:
                                    (SEQ ID NO: 27)
5'-AGCTAAAAAAGGCTATGGAGAGTCATCATCTCTTGAAAGATGACTC

TCCATAGCCTGGG-3'

4) Target:
                                    (SEQ ID NO: 28)
CAAGCAGTGTTCATTGGCCATGA Sense strand:
                                    (SEQ ID NO: 29)
5'-GATCCCCAGCAGTGTTCATTGGCCATTTCAAGAGAATG

GCCAATGAACACTGCTTTTTT-3'

Antisense strand:
                                    (SEQ ID NO: 30)
5'-AGCTAAAAAAGCAGTGTTCATTGGCCATTCTCTTGAAATG

GCCAATGAACACTGCTGGG-3'

5) Target:
                                    (SEQ ID NO: 31)
CAGCACATGGAGGACTGGATTCC Sense strand
                                    (SEQ ID NO: 32)
5'-GATCCCCGCACATGGAGGACTGGATTTTCAAGAGAAATC

CAGTCCTCCATGTGCTTTTT-3'

Antisense strand:
                                    (SEQ ID NO: 33)
5'-AGCTAAAAAGCACATGGAGGACTGGATTTCTCTTGAAAA

TCCAGTCCTCCATGTGCGGG-3'
```

In addition to siRNAs, other means are known in the art for inhibiting the expression of antisense molecules, ribozymes, and the like are well known to those of skill in the art. The nucleic acid molecule can be a DNA probe, a riboprobe, a peptide nucleic acid probe, a phosphorothioate probe, or a 2'-O methyl probe.

Generally, to assure specific hybridization, the antisense sequence is substantially complementary to the target sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to the sEH gene is retained as a functional property of the polynucleotide. In one embodiment, the antisense molecules form a triple helix-containing, or "triplex" nucleic acid. Triple helix formation results in inhibition of gene expression by, for example, preventing transcription of the target gene (see, e.g., Cheng et al., 1988, J. Biol. Chem. 263:15110; Ferrin and Camerini-Otero, 1991, Science 354:1494; Ramdas et al., 1989, J. Biol. Chem. 264:17395; Strobel et al., 1991, Science 254:1639; and Rigas et al., 1986, Proc. Natl. Acad. Sci. U.S.A. 83:9591)

Antisense molecules can be designed by methods known in the art. For example, Integrated DNA Technologies (Coralville, Iowa) makes available a program found on the worldwide web "biotools.idtdna.com/antisense/AntiSense.aspx", which will provide appropriate antisense sequences for nucleic acid sequences up to 10,000 nucleotides in length. Using this program with the sEH gene provides the following exemplar sequences:

1) UGUCCAGUGCCCACAGUCCU (SEQ ID NO: 34)

2) UUCCCACCUGACACGACUCU (SEQ ID NO: 35)

3) GUUCAGCCUCAGCCACUCCU (SEQ ID NO: 36)

4) AGUCCUCCCGCUUCACAGA (SEQ ID NO: 37)

5) GCCCACUUCCAGUUCCUUUCC (SEQ ID NO: 38)

In another embodiment, ribozymes can be designed to cleave the mRNA at a desired position. (See, e.g., Cech, 1995, Biotechnology 13:323; and Edgington, 1992, Biotechnology 10:256 and Hu et al., PCT Publication WO 94/03596).

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules may be prepared by de novo chemical synthesis or by cloning. For example, an antisense RNA can be made by inserting (ligating) a sEH gene sequence in reverse orientation operably linked to a promoter in a vector (e.g., plasmid). Provided that the promoter and, preferably termination and polyadenylation signals, are properly positioned, the strand of the inserted sequence corresponding to the noncoding strand are transcribed and act as an antisense oligonucleotide.

It are appreciated that the oligonucleotides can be made using nonstandard bases (e.g., other than adenine, cytidine, guanine, thymine, and uridine) or nonstandard backbone structures to provides desirable properties (e.g., increased nuclease-resistance, tighter-binding, stability or a desired Tm). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al., 1991, Science 254:1497) or incorporating 2'-O-methyl ribonucleotides, phosphorothioate nucleotides, methyl phosphonate nucleotides, phosphotriester nucleotides, phosphorothioate nucleotides, phosphoramidates.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996). Another subsequence, the h (hydrophobic) domain of signal peptides, was found to have similar cell membrane translocation characteristics (see, e.g., Lin et al., J. Biol. Chem. 270:14255-14258 (1995)). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

More recently, it has been discovered that siRNAs can be introduced into mammals without eliciting an immune response by encapsulating them in nanoparticles of cyclodextrin. Information on this method can be found on the worldwide web at "nature.com/news/2005/050418/full/050418-6.html."

In another method, the nucleic acid is introduced directly into superficial layers of the skin or into muscle cells by a jet of compressed gas or the like. Methods for administering naked polynucleotides are well known and are taught, for example, in U.S. Pat. No. 5,830,877 and International Publication Nos. WO 99/52483 and WO 94/21797. Devices for accelerating particles into body tissues using compressed gases are described in, for example, U.S. Pat. Nos. 6,592,545, 6,475,181, and 6,328,714. The nucleic acid may be lyophilized and may be complexed, for example, with polysaccharides to form a particle of appropriate size and mass for acceleration into tissue. Conveniently, the nucleic acid can be placed on a gold bead or other particle which provides suitable mass or other characteristics. Use of gold beads to carry nucleic acids into body tissues is taught in, for example, U.S. Pat. Nos. 4,945,050 and 6,194,389.

The nucleic acid can also be introduced into the body in a virus modified to serve as a vehicle without causing pathogenicity. The virus can be, for example, adenovirus, fowlpox virus or vaccinia virus.

miRNAs and siRNAs differ in several ways: miRNA derive from points in the genome different from previously recognized genes, while siRNAs derive from mRNA, viruses or transposons, miRNA derives from hairpin structures, while siRNA derives from longer duplexed RNA, miRNA is conserved among related organisms, while siRNA usually is not, and miRNA silences loci other than that from which it derives, while siRNA silences the loci from which it arises. Interestingly, miRNAs tend not to exhibit perfect complementarity to the mRNA whose expression they inhibit. See, McManus et al., supra. See also, Cheng et al., Nucleic Acids Res. 33(4):1290-7 (2005); Robins and Padgett, Proc Natl Acad Sci USA. 102(11): 4006-9 (2005); Brennecke et al., PLoS Biol. 3(3):e85 (2005). Methods of designing miRNAs are known. See, e.g., Zeng et al., Methods Enzymol. 392:371-80 (2005); Krol et al., J Biol Chem. 279(40):42230-9 (2004); Ying and Lin, Biochem Biophys Res Commun. 326(3):515-20 (2005).

In some embodiments, the endogenous polynucleotide encoding sEH in the subject can be rendered non-functional or non-expressing, e.g., by employing gene therapy methodologies. This can be accomplished using any method known in the art, including the working embodiment described herein. In varying embodiments, the endogenous gene encoding sEH in the subject is rendered non-functional or non-expressing in certain desired tissues, e.g., in renal tissue or more specifically in podocyte cells, as demonstrated herein. In varying embodiments, the endogenous gene encoding sEH in the subject is rendered non-functional or non-expressing by employing homologous recombination, mutating, replacing or eliminating the functional or expressing gene encoding sEH. Illustrative methods are known in the art and described, e.g., in Flynn, et al., *Exp Hematol*. (2015) June 19. pii: S0301-472X(15)00207-6 (using CRISPR); Truong, et al, *Nucleic Acids Res*. (2015) June 16. pii: gkv601 (using split-Cas9); Yang, *Mil Med Res*. (2015) May 9; 2:11 (using CRISPR-Cas9); and Imai, et al., *Intern Med*. (2004) February; 43(2):85-96.

f. Epoxy-Fatty Acids

In some embodiments, an epoxy-fatty acid is administered as an agent that increases epoxy-fatty acids. Illustrative epoxy-fatty acids include epoxides of linoleic acid, eicosapentaenoic acid ("EPA") and docosahexaenoic acid ("DHA").

The fatty acids eicosapentaenoic acid ("EPA") and docosahexaenoic acid ("DHA") have recently become recognized as having beneficial effects, and fish oil tablets, which are a good source of these fatty acids, are widely sold as supplements. In 2003, it was reported that these fatty acids reduced pain and inflammation. Sethi, S. et al., Blood 100: 1340-1346 (2002). The paper did not identify the mechanism of action, nor the agents responsible for this relief.

Cytochrome P450 ("CYP450") metabolism produces cis-epoxydocosapentaenoic acids ("EpDPEs") and cis-epoxyeicosatetraenoic acids ("EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS-(nitric oxide) and COX-derived (prostacyclin) vasodilators. Overall cytochrome P450 (CYP450) metabolism of polyunsaturated fatty acids produces epoxides, such as EETs, which are prime candidates for the active mediator(s). 14(15)-EpETE, for example, is derived via epoxidation of the 14,15-double bond of EPA and is the ω-3 homolog of 14(15)-EpETrE ("14(15)EET") derived via epoxidation of the 14,15-double bond of arachidonic acid.

As mentioned, it is beneficial to elevate the levels of EETs, which are epoxides of the fatty acid arachidonic acid. Our studies of the effects of EETs has led us to realization that the anti-inflammatory effect of EPA and DHA are likely due to increasing the levels of the epoxides of these two fatty acids. Thus, increasing the levels of epoxides of EPA, of DHA, or of both, will act to reduce, mitigate, ameliorate, improve symptoms associated with a neuropsychiatric illness characterized by depressive symptoms, in mammals in need thereof. This beneficial effect of the epoxides of these fatty acids has not been previously recognized. Moreover, these epoxides have not previously been administered as agents, in part because, as noted above, epoxides have generally been considered too labile to be administered.

Like EETs, the epoxides of EPA and DHA are substrates for sEH. The epoxides of EPA and DHA are produced in the body at low levels by the action of cytochrome P450s. Endogenous levels of these epoxides can be maintained or increased by the administration of sEHI. However, the endogenous production of these epoxides is low and usually occurs in relatively special circumstances, such as the resolution of inflammation. Our expectation is that administering these epoxides from exogenous sources will aid in the resolution of symptoms of neuropsychiatric illnesses characterized by depressive symptoms. It is further beneficial with pain or inflammation to inhibit sEH with sEHI to reduce hydrolysis of these epoxides, thereby maintaining them at relatively high levels.

EPA has five unsaturated bonds, and thus five positions at which epoxides can be formed, while DHA has six. The epoxides of EPA are typically abbreviated and referred to generically as "EpETEs", while the epoxides of DHA are typically abbreviated and referred to generically as "EpDPEs". The specific regioisomers of the epoxides of each fatty acid are set forth in the following Table 3:

TABLE 3

Regioisomers of Eicosapentaenoic acid ("EPA") epoxides:

1. Formal name: (±)5(6)- epoxy- 8Z, 11Z, 14Z, 17Z- eicosatetraenoic acid,
   Synonym 5(6)- epoxy Eicosatetraenoic acid
   Abbreviation 5(6)- EpETE
2. Formal name: (±)8(9)- epoxy- 5Z, 11Z, 14Z, 17Z - eicosatetraenoic acid,
   Synonym 8(9)- epoxy Eicosatetraenoic acid
   Abbreviation 8(9)- EpETE
3. Formal name: (±)11(12)- epoxy- 5Z, 8Z, 14Z, 17Z - eicosatetraenoic acid,
   Synonym 11(12)- epoxy Eicosatetraenoic acid
   Abbreviation 11(12)- EpETE
4. Formal name: (±)14(15)- epoxy- 5Z, 8Z, 11Z, 17Z- eicosatetraenoic acid,
   Synonym 14(15)- epoxy Eicosatetraenoic acid
   Abbreviation 14(15)- EpETE
5. Formal name: (±)17(18)- epoxy- 5Z, 8Z, 11Z, 14Z- eicosatetraenoic acid,
   Synonym 17(18)- epoxy Eicosatetraenoic acid
   Abbreviation 17(18)- EpETE Regioisomers of Docosahexaenoic acid ("DHA") epoxides:

1. Formal name: (±) 4(5)- epoxy- 7Z, 10Z, 13Z, 16Z, 19Z - docosapentaenoic acid,
   Synonym 4(5)- epoxy Docosapentaenoic acid
   Abbreviation 4(5)- EpDPE
2. Formal name: (±) 7(8)- epoxy- 4Z, 10Z, 13Z, 16Z, 19Z - docosapentaenoic acid,
   Synonym 7(8)- epoxy Docosapentaenoic acid
   Abbreviation 7(8)- EpDPE
3. Formal name: (±)10(11)- epoxy- 4Z, 7Z, 13Z, 16Z, 19Z - docosapentaenoic acid,
   Synonym 10(11)- epoxy Docosapentaenoic acid
   Abbreviation 10(11)- EpDPE
4. Formal name: (±)13(14)- epoxy- 4Z, 7Z, 10Z, 16Z, 19Z - docosapentaenoic acid,
   Synonym 13(14)- epoxy Docosapentaenoic acid
   Abbreviation 13(14)- EpDPE
5. Formal name: (±) 16(17)- epoxy- 4Z, 7Z, 10Z, 13Z, 19Z - docosapentaenoic acid,
   Synonym 16(17)- epoxy Docosapentaenoic acid
   Abbreviation 16(17)- EpDPE
6. Formal name: (±) 19(20)- epoxy- 4Z, 7Z, 10Z, 13Z, 16Z - docosapentaenoic acid,
   Synonym 19(20)- epoxy Docosapentaenoic acid
   Abbreviation 19(20)- EpDPE Any of these epoxides, or combinations of any of these, can be administered in the compositions and methods.

4. Secondary Agents that Synergize with Inhibitors of Soluble Epoxide Hydrolase

In varying embodiments, the agent that increases epoxy-fatty acids or the inhibitor of soluble epoxide hydrolase is co-administered with an enhancing or synergizing agent. Illustrative agents that enhance the activity or efficaciousness of directly inhibiting soluble epoxide hydrolase include without limitation inhibitors of cyclooxygenase-2 (COX-2), inhibitors of phosphodiesterase, agonists of peroxisome proliferator activated receptor alpha (PPARα) and agonists of peroxisome proliferator activated receptor gamma (PPARγ).

Illustrative selective or preferential inhibitors of COX-2 that may be co-administered with an inhibitor of soluble epoxide hydrolase include without limitation celecoxib, valdecoxib, lumiracoxib, etoricoxib, and rofecoxib. Illustrative inhibitors of phosphodiesterase 4 that may be co-administered with an inhibitor of soluble epoxide hydrolase include without limitation rolipram, roflumilast, cilomilast, ariflo, HT0712, ibudilast and mesembrine. Illustrative inhibitors of phosphodiesterase 5 that may be co-administered with an inhibitor of soluble epoxide hydrolase include without limitation sildenafil, zaprinast, tadalafil, udenafil, avanafil and vardenafil. Illustrative agonists of PPARα that may be co-administered with an inhibitor of soluble epoxide hydrolase include without limitation clofibrate, gemfibrozil, ciprofibrate, bezafibrate, and fenofibrate. Illustrative agonists of PPARγ that may be co-administered with an inhibitor of soluble epoxide hydrolase include without limitation thiazolidinediones (TZDs).

5. Agents for Treating Neuropsychiatric Disorders

Pharmacological agents for co-administration with an agent that increases epoxy-fatty acids include antidepressants, mood-stabilizers, anti-psychotics and anxiolytics. When co-administered with an agent that increases epoxy-fatty acids, e.g., an inhibitor of soluble epoxide hydrolase, the effectiveness of the antidepressant, mood-stabilizer, antipsychotic and/or anxiolytic in mitigating, ameliorating, reducing and/or inhibiting one or more symptoms associated with a neuropsychiatric disorder is enhanced, in terms of increased potency, reduced dosage requirements, earlier onset to effectiveness and sustained efficacy.

a. Antidepressants

Illustrative antidepressant agents that can be co-administered with an agent that increases epoxy-fatty acids include without limitation selective serotonin reuptake inhibitors (SSRIs), serotonin-norepinephrine reuptake inhibitors (SNRIs), tricyclic or tetracyclic antidepressants (TCAs), a monoamine oxidase inhibitors (MAOIs) and atypical antidepressants.

Illustrative selective serotonin reuptake inhibitors (SSRIs) include without limitation citalopram, escitalopram, fluoxetine, fluvoxamine, fluvoxamine CR, paroxetine, paroxetine CR, and sertraline.

Illustrative serotonin-norepinephrine reuptake inhibitors (SNRIs) include without limitation desvenlafaxine, duloxetine, venlafaxine, venlafaxine XR, milnacipran, and levomilnacipran.

Illustrative tricyclic or tetracyclic antidepressants (TCAs) include without limitation amitriptyline, amoxapine, desipramine, doxepin, imipramine, nortriptyline, protriptyline, trimipramine and maprotiline.

Illustrative monoamine oxidase inhibitors (MAOIs) include without limitation selegiline, moclobemide, tranylcypromine, isocarboxazid and phenylzine.

b. Mood-Stabilizers

Illustrative mood stabilizers that can be co-administered with an agent that increases epoxy-fatty acids include without limitation lithium carbonate, divalproex sodium, valproic acid, valproate semisodium, sodium valproate, tiagabine, levetiracetam, lamotrigine, gabapentin, carbamazepine, oxcarbazepine, topiramate, zonisamide, aripiprazole, risperidone, olanzapine, quetiapine, asenapine, paliperidone, ziprasidone, lurasidone, verapamil, clonidine, propranolol, mexiletine, guanfacine and omega-3 fatty acids.

c. Antipsychotics

Illustrative antipsychotics that can be co-administered with an agent that increases epoxy-fatty acids include without limitation a butyrophenone, a diphenylbutylpiperidine, a phenothiazine, a thioxanthene, or is an atypical antipsychotic agent.

In varying embodiments, the antipsychotic is selected from the group consisting of benperidol. bromperidol, droperidol, haloperidol, moperone, pipamperone, timiperone, fluspirilene, penfluridol, pimozide, phenothiazines, acepromazine, chlorpromazine, cyamemazine, dixyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, thioxanthenes, chlorprothixene, clopenthixol, flupentixol, thiothixene, zuclopenthixol, clotiapine, loxapine, prothipendyl, carpipramine, clocapramine, molindone, mosapramine, sulpiride, sultopride, veralipride, amisulpride, amoxapine, aripiprazole, asenapine, cariprazine, clozapine, blonanserin, iloperidone, lurasidone, melperone, nemonapride, olanzapine, paliperidone, perospirone, quetiapine, remoxipride, risperidone, sertindole, sultopride, trimipramine, ziprasidone, zotepine, brexpiprazole, ITI-007, pimavanserin and RP5063.

d. Anxiolytics

Illustrative anxiolytics (e.g., anti-anxiety agent, anti-panic agent) that can be co-administered with an agent that increases epoxy-fatty acids include without limitation a barbiturate, a benzodiazepine and a beta-blocker.

In varying embodiments, the anxiolytic drug is selected from the group consisting of alprazolam, bromazepam, chlordiazepoxide, clonazepam, clorazepate, diazepam, flurazepam, lorazepam, oxazepam, temazepam, triazolam, tofisopam, clonidine, guanfacine, mebicar, fabomotizole, selank, bromantane, emoxypine, buspirone, tandospirone, hydroxyzine, pregabalin, menthyl isovalerate, cannabidiol (cbd), tetrahydrocannabinol, *Garcinia indica* (kokum), *Scutellaria lateriflora, Coriandrum sativum* (coriander), *Salvia elegans* (pineapple sage), picamilon, chlorpheniramine, diphenhydramine, melatonin and myo-inositol.

6. Formulation and Administration

In various embodiments of the compositions, the agent that increases epoxy-fatty acids (e.g., an inhibitor of sEH, an EET, an epoxy-fatty acid, and mixtures thereof) is co-administered with the second agent (e.g., antidepressant, mood stabilizer, anti-psychotic, anxiolytic). In some embodiments, the agent that increases epoxy-fatty acids comprises an epoxide of EPA, an epoxide of DHA, or epoxides of both, and an sEHI.

The agent that increases epoxy-fatty acids and the second agent (e.g., antidepressant, mood stabilizer, anti-psychotic, anxiolytic) independently can be prepared and administered in a wide variety of oral, parenteral and topical dosage forms. The agent that increases epoxy-fatty acids and the second agent (e.g., antidepressant, mood stabilizer, anti-psychotic, anxiolytic) can be administered via the same or different routes of administration. In varying embodiments, the agent that increases epoxy-fatty acids and the second agent (e.g., antidepressant, mood stabilizer, anti-psychotic, anxiolytic) independently can be administered orally, by injection, that is, intravenously, intramuscularly, intracutaneously, subcutaneously, intraduodenally, or intraperitoneally. The agent that increases epoxy-fatty acids and the second agent (e.g., antidepressant, mood stabilizer, anti-psychotic, anxiolytic) can also be administered by inhalation, for example, intranasally. Additionally, the agent that increases epoxy-fatty acids and the second agent (e.g., antidepressant, mood stabilizer, anti-psychotic, anxiolytic) can be administered transdermally.

In varying embodiments, one or both of the agent that increases epoxy-fatty acids (e.g., an sEHI or a pharmaceutically acceptable salt of the inhibitor and, optionally, one or more EETs or epoxides of EPA or of DHA, or of both), and/or the second agent (e.g., antidepressant, mood stabilizer, anti-psychotic, anxiolytic) are specifically, predominantly or preferentially targeted to the brain. Methods for preferentially targeting therapeutic agents to brain tissues are known in the art and find use. Illustrative strategies useful for targeted and/or enhanced delivery of organic compounds and oligonucleotides to the brain are discussed in, e.g., Hanson, et al., *BMC Neurosci.* (2008) 9 Suppl 3:S5; Kim, et al., *Mol Ther.* (2012) 20(4):829-39; Gong, et al.,

*Biomaterials.* (2012) 33(12):3456-63; Gomez, et al., *Front Biosci* (Schol Ed). (2012) 4:74-89; Patel, et al., *CNS Drugs.* (2009) 23(1):35-58; Fonseca-Santos, et al., *Int J Nanomedicine.* (2015) 10:4981-5003; Sela, et al., *J Nanobiotechnology.* (2015) Oct. 21; 13:71; and Raj adhyaksha, et al., *Curr Drug Discov Technol.* (2011) 8(2):87-101.

In varying embodiments, in order to enhance delivery to the brain, the one or more agents or compounds can be co-administered with, conjugated to or encapsulated within an agent that facilitate transport across the blood-brain-barrier. Strategies and agents useful for facilitating delivery across the blood-brain-barrier are known in the art and can be employed in the present methods. Current strategies for delivering active agents across the blood-brain barrier and that find use in the present methods include without limitation nanocarriers and nanoparticles (Tam, et al., *Int J Pharm.* (2016) 515(1-2):331-342; Zhao, et al., *Nanoscale Res Lett.* 2016 December; 11(1):451; Song, et al., *Mol Pharm.* (2016) Oct. 4; PMID: 27700119; Lalatsa, et al., *Int Rev Neurobiol.* 2016; 130:115-53; Kundo, et al., *ACS Chem Neurosci.* (2016) Oct. 3; PMID: 27642670); functionalized carbon nanotubes (Costa, et al., *J Control Release.* (2016) 241:200-219); nanowires (Sharma, et al., *CNS Neurol Disord Drug Targets.* 2016 Aug. 19; PMID: 27538949); viral vectors (Fu, et al., *Curr Opin Virol.* (2016) 21:87-92); liposomes and exosomes (Tremmel, et al., *Int J Pharm.* (2016) 512(1):87-95; Sánchez-Purrà, et al., *Int J Pharm.* (2016) 511(2):946-56; Bender, et al. *J Vis Exp.* (2016) Jul. 23; (113). doi: 10.3791/54106; Ha, et al., *Acta Pharm Sin B.* (2016) 6(4): 287-96); dendrimers (Jiang, et al, *Colloids Surf B Biointerfaces.* (2016) 147:242-9) and ultrasound (Park, et al., *J Control Release.* (2016) Oct. 11. pii: S0168-3659(16)30955-5; Airan, et al., *Mol Imaging Biol.* (2016) Aug. 1; PMID: 27481359). In varying embodiments, the one or more compounds can be conjugated to or administered in conjunction with a peptide that promotes transcytosis and traversal of the blood-brain barrier. Illustrative peptides include without limitation Angiopep-2 (Li, et al., *Oncotarget.* 2016 Oct. 17. doi: 10.18632; PMID: 27765902); Transferrin (Nanoscale. (2016) 8(37):16662-16669); penetratin (Spencer, et al., *Ann Clin Transl Neurol.* (2016) 3(8):588-606); and M36 fungalysin metalloprotease (WO 2013/036827).

Furthermore, the agent that increases epoxy-fatty acids and the second agent (e.g., antidepressant, mood stabilizer, anti-psychotic, anxiolytic) can be co-formulated in a single composition or can be formulated for separate co-administration. Accordingly, in some embodiments, the methods contemplate administration of compositions comprising a pharmaceutically acceptable carrier or excipient, an agent that increases epoxy-fatty acids (e.g., an sEHI or a pharmaceutically acceptable salt of the inhibitor and, optionally, one or more EETs or epoxides of EPA or of DHA, or of both), and optionally the second agent (e.g., antidepressant, mood stabilizer, anti-psychotic, anxiolytic). In some embodiments, the methods comprise administration of an sEHI and one or more epoxides of EPA or of DHA, or of both.

For preparing the pharmaceutical compositions, the pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active components in water with viscous material, such as natural or synthetic gums, resins, methylcellulose, sodium carboxymethylcellulose, polyethylene glycols and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

A variety of solid, semisolid and liquid vehicles have been known in the art for years for topical application of agents to the skin. Such vehicles include creams, lotions, gels, balms, oils, ointments and sprays. See, e.g., Provost C. "Transparent oil-water gels: a review," Int J Cosmet Sci. 8:233-247 (1986), Katz and Poulsen, Concepts in biochemical pharmacology, part I. In: Brodie B B, Gilette J R, eds. Handbook of Experimental Pharmacology. Vol. 28. New York, N.Y.: Springer; 107-174 (1971), and Hadgcraft, "Recent progress in the formulation of vehicles for topical applications," Br J Dermatol., 81:386-389 (1972). A number of topical formulations of analgesics, including capsaicin (e.g., Capsin®), so-called "counter-irritants" (e.g., Icy-Hot®, substances such as menthol, oil of wintergreen, camphor, or eucalyptus oil compounds which, when applied to skin over an area presumably alter or off-set pain in joints or muscles served by the same nerves) and salicylates (e.g. BenGay®), are known and can be readily adapted for topical administration of sEHI by replacing the active ingredient or ingredient with an sEHI, with or without EETs. It is presumed that the person of skill is familiar with these various vehicles and preparations and they need not be described in detail herein.

The agent that increases epoxy-fatty acids (e.g., an inhibitor of sEH, an EET, an epoxy-fatty acid, and mixtures thereof), optionally mixed with an anti-inflammatory and/or analgesic agent, can be mixed into such modalities (creams, lotions, gels, etc.) for topical administration. In general, the concentration of the agents provides a gradient which drives the agent into the skin. Standard ways of determining flux of drugs into the skin, as well as for modifying agents to speed or slow their delivery into the skin are well known in the art and taught, for example, in Osborne and Amann, eds., Topical Drug Delivery Formulations, Marcel Dekker, 1989. The use of dermal drug delivery agents in particular is taught in, for example, Ghosh et al., eds., Transdermal and Topical Drug Delivery Systems, CRC Press, (Boca Raton, Fla., 1997).

In some embodiments, the agents are in a cream. Typically, the cream comprises one or more hydrophobic lipids, with other agents to improve the "feel" of the cream or to provide other useful characteristics. In one embodiment, for example, a cream may contain 0.01 mg to 10 mg of sEHI, with or without one or more EETs, per gram of cream in a white to off-white, opaque cream base of purified water USP, white petrolatum USP, stearyl alcohol NF, propylene glycol USP, polysorbate 60 NF, cetyl alcohol NF, and benzoic acid USP 0.2% as a preservative. In various embodiments, an agent that increases epoxy-fatty acids (e.g., an sEHI or a pharmaceutically acceptable salt of the inhibitor and, optionally, one or more EETs or epoxides of EPA or of DHA, or of both), and/or the second agent (e.g., antidepressant, mood stabilizer, anti-psychotic, anxiolytic) can be mixed into a commercially available cream, Vanicream® (Pharmaceutical Specialties, Inc., Rochester, Minn.) comprising purified water, white petrolatum, cetearyl alcohol and ceteareth-20, sorbitol solution, propylene glycol, simethicone, glyceryl monostearate, polyethylene glycol monostearate, sorbic acid and BHT.

In other embodiments, the agent or agents are in a lotion. Typical lotions comprise, for example, water, mineral oil, petrolatum, sorbitol solution, stearic acid, lanolin, lanolin alcohol, cetyl alcohol, glyceryl stearate/PEG-100 stearate, triethanolamine, dimethicone, propylene glycol, microcrystalline wax, tri (PPG-3 myristyl ether) citrate, disodium EDTA, methylparaben, ethylparaben, propylparaben, xanthan gum, butylparaben, and methyldibromo glutaronitrile.

In some embodiments, the agent is, or agents are, in an oil, such as jojoba oil. In some embodiments, the agent is, or agents are, in an ointment, which may, for example, white petrolatum, hydrophilic petrolatum, anhydrous lanolin, hydrous lanolin, or polyethylene glycol. In some embodiments, the agent is, or agents are, in a spray, which typically comprise an alcohol and a propellant. If absorption through the skin needs to be enhanced, the spray may optionally contain, for example, isopropyl myristate.

Whatever the form in which the agents that inhibit sEH are topically administered (that is, whether by solid, liquid, lotion, gel, spray, etc.), in various embodiments they are administered at a therapeutically effective dosage of about 0.01 mg to 10 mg per 10 cm$^2$. An exemplary therapeutically effective dose for systemic administration of an inhibitor of sEH is from about 0.1 µg/kg to about 100 mg/kg, e.g., about 0.001 mg/kg to about 10 mg/kg, e.g., about 0.01 mg/kg to about 1.0 mg/kg, body weight of the mammal. In various embodiments, dose and frequency of administration of an sEH inhibitor are selected to produce plasma concentrations within the range of 2.5 µM and 30 nM.

The agent that increases epoxy-fatty acids (e.g., an inhibitor of sEH, an EET, an epoxy-fatty acid, and mixtures thereof), optionally mixed with an anti-inflammatory and/or analgesic agent, can be introduced into the bowel by use of a suppository. As is known in the art, suppositories are solid compositions of various sizes and shapes intended for introduction into body cavities. Typically, the suppository comprises a medication, which is released into the immediate area from the suppository. Typically, suppositories are made using a fatty base, such as cocoa butter, that melts at body temperature, or a water-soluble or miscible base, such as glycerinated gelatin or polyethylene glycol.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification.

A therapeutically effective amount or a sub-therapeutic amount of the agent that increases epoxy-fatty acids can be co-administered with the second agent (e.g., antidepressant, mood stabilizer, anti-psychotic, anxiolytic). The dosage of the specific compounds depends on many factors that are well known to those skilled in the art. They include for example, the route of administration and the potency of the particular compound. An exemplary therapeutically effective dose is from about 0.1 µg/kg to about 100 mg/kg, e.g., about 0.001 mg/kg to about 10 mg/kg, e.g., about 0.01 mg/kg to about 1.0 mg/kg, body weight of the mammal. Determination of an effective amount is well within the capability of those skilled in the art, especially in light of the detailed disclosure provided herein. Generally, an efficacious or effective amount of a combination of one or more agents is determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the one or more agents are described, for example, in *Goodman and Gilman's The Pharmacological Basis of Therapeutics,* 12th Edition, 2010, McGraw-Hill Professional; in a Physicians' Desk Reference (PDR), 69$^{th}$ Edition, 2015 and 70$^{th}$ Edition, 2016, PDR Network; in *Remington: The Science and Practice of Pharmacy,* 21$^{st}$ Ed., 2005, supra; and in *Martindale: The Complete Drug Reference*, Sweetman, 2005, London: Pharmaceutical Press., and in Martindale, *Martindale: The Extra*

*Pharmacopoeia*, 31st Edition., 1996, Amer Pharmaceutical Assn, each of which are hereby incorporated herein by reference.

EETs, EpDPEs, or EpETEs are unstable, and can be converted to the corresponding diols, in acidic conditions, such as those in the stomach. To avoid this, EETs, EpDPEs, or EpETEs can be administered intravenously or by injection. EETs, EpDPEs, or EpETEs intended for oral administration can be encapsulated in a coating that protects the compounds during passage through the stomach. For example, the EETs, EpDPEs, or EpETEs can be provided with a so-called "enteric" coating, such as those used for some brands of aspirin, or embedded in a formulation. Such enteric coatings and formulations are well known in the art. In some formulations, the compositions are embedded in a slow-release formulation to facilitate administration of the agents over time.

It is understood that, like all drugs, sEHIs have half-lives defined by the rate at which they are metabolized by or excreted from the body, and that the sEHIs will have a period following administration during which they are present in amounts sufficient to be effective. If EETs, EpDPEs, or EpETEs are administered after the sEHI is administered, therefore, it is desirable that the EETs, EpDPEs, or EpETEs be administered during the period during which the sEHI are present in amounts to be effective in delaying hydrolysis of the EETs, EpDPEs, or EpETEs. Typically, the EETs, EpDPEs, or EpETEs are administered within 48 hours of administering an sEH inhibitor. Preferably, the EETs, EpDPEs, or EpETEs are administered within 24 hours of the sEHI, and even more preferably within 12 hours. In increasing order of desirability, the EETs, EpDPEs, or EpETEs are administered within 10, 8, 6, 4, 2, hours, 1 hour, or one half hour after administration of the inhibitor. When co-administered, the EETs, EpDPEs, or EpETEs are preferably administered concurrently with the sEHI.

7. Methods of Monitoring

Clinical efficacy can be monitored using any method known in the art. Measurable parameters to monitor efficacy will depend on the condition being treated. For monitoring the status or improvement of one or more symptoms associated with a neuropsychiatric illness, both subjective parameters (e.g., patient reporting) and objective parameters (e.g., reduction or elimination of depressive symptoms and/or other symptoms associated with the neuropsychiatric illness observable by a clinician or psychologist; brain scans; cognitive functions (e.g., verbal learning, speed of processing, attention/vigilance, working memory, visual learning, reasoning and problem solving, social cognition)). Symptoms for patients with psychiatric disorders can be measured and quantified using appropriate tests and scales established in the art, e.g., HAMD (Hamilton Depression Rating Scale) (Williams, *Arch Gen Psychiatry.* 1988 August; 45(8):742-7 and Zimmerman, et al., *J Affect Disord.* 2013 Sep. 5; 150(2):384-8), HAMA (Hamilton Anxiety Rating Scale) (Bruss, et al., *Psychiatry Res.* 1994 August; 53(2): 191-202), YMRS (Young Mania Rating Scale) (Lukasiewicz, et al., *Int J Methods Psychiatr Res.* 2013 March; 22(1):46-58), BPRS (Brief Psychiatric Rating Scale) (Bell, et al., *J Nerv Ment Dis.* 1992 November; 180(11):723-8 and Lachar, et al., *J Am Acad Child Adolesc Psychiatry.* 2001 March; 40(3):333-40), PANSS (Positive and Negative Syndrome Scale) (Kay, et al., *Schizophr Bull.* 1987; 13(2):261-76 and Kay, et al., *Psychiatry Res.* 1988 January; 23(1):99-110), and/or CGS-I (Clinical Global Impression—Severity) (Pinna, et al., *Ann Gen Psychiatry.* 2015 Feb. 13; 14:6). Applicable assays or diagnostic parameters for the monitoring neuropsychiatric illness are known in the art, e.g., as set forth in the Diagnostic and Statistical Manual of Mental Disorders, 5th Edition (DSM-5) American Psychiatric Association, American Psychiatric Publishing, 2013 and/or the International Statistical Classification of Diseases and Related Health Problems (ICD)-11 of the World Health Organization (WHO) (available online at http://www.who.int/classifications/icd/en/). Behavioral changes in the subject (e.g., attitude, mood, appetite, grooming, sociability, energy levels, increased activity levels, weight gain/loss, exhibition of increased comfort) are also relevant to neuropsychiatric disorders having depressive symptoms. These parameters can be measured using any methods known in the art. In varying embodiments, the different parameters can be assigned a score. Further, the scores of two or more parameters can be combined to provide an index for the subject.

Observation of the stabilization, improvement and/or reversal of one or more symptoms or parameters by a measurable amount indicates that the treatment or prevention regime is efficacious. Observation of the progression, increase or exacerbation of one or more symptoms indicates that the treatment or prevention regime is not efficacious. For example, in the case of a neuropsychiatric illness (e.g., depression), observation the improvement of one or both of subjective parameters (e.g., patient reporting) and objective parameters (e.g., reduction or elimination of depressive symptoms and/or other symptoms associated with the neuropsychiatric illness observable by a clinician or psychologist; brain scans; cognitive functions (e.g., verbal learning, speed of processing, attention/vigilance, working memory, visual learning, reasoning and problem solving, social cognition)) and/or behavioral changes in the subject (e.g., attitude, mood, appetite, grooming, sociability, energy levels, increased activity levels, weight gain/loss, exhibition of increased comfort) after one or more co-administrations of the agent that increases epoxy-fatty acids (e.g., an inhibitor of sEH) indicates that the treatment or prevention regime is efficacious. Likewise, observation of reduction or decline, lack of improvement or worsening of one or both of subjective parameters (e.g., patient reporting) and objective parameters (e.g., reduction or elimination of depressive symptoms and/or other symptoms associated with the neuropsychiatric illness observable by a clinician or psychologist; brain scans; cognitive functions (e.g., verbal learning, speed of processing, attention/vigilance, working memory, visual learning, reasoning and problem solving, social cognition)), and/or behavioral changes in the subject (e.g., attitude, mood, appetite, grooming, sociability, energy levels, increased activity levels, weight gain/loss, exhibition of increased comfort) after one or more co-administrations of the agent that increases epoxy-fatty acids (e.g., an inhibitor of sEH) indicates that the treatment or prevention regime is not efficacious.

In certain embodiments, the monitoring methods can entail determining a baseline value of a measurable biomarker or disease parameter in a subject before administering a dosage of the one or more active agents described herein, and comparing this with a value for the same measurable biomarker or parameter after a course of treatment.

In other methods, a control value (i.e., a mean and standard deviation) of the measurable biomarker or parameter is determined for a control population. In certain embodiments, the individuals in the control population have not received prior treatment and do not have the disease condition subject to treatment, nor are at risk of developing the disease condition subject to treatment (e.g., do not have and are not at risk of developing a neuropsychiatric illness characterized by depressive symptoms). In some cases, if the value of the measurable biomarker or clinical parameter approaches the control value, then treatment is considered efficacious. In other embodiments, the individuals in the control population have not received prior treatment and have been diagnosed with the disease condition subject to treatment (e.g., has been diagnosed with a neuropsychiatric illness characterized by depressive symptoms). In such cases, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and need not be resumed. In all of these cases, a significant difference relative to the control level (i.e., more than a standard deviation) is an indicator that treatment should be resumed in the subject.

8. Kits

Further provided are kits. In varying embodiments, the kits comprise one or more agents that increase the level of epoxy-fatty acids and one or more additional agents selected from antidepressants, mood stabilizer, antipsychotics and anxiolytics. Embodiments of the agents that increase the level of epoxy-fatty acids and embodiments of the additional agent(s) are as described above and herein. Embodiments of formulations of the agents are as described above and herein. In varying embodiments, the agent that increases the level of epoxy-fatty acids and the additional agent(s) can be co-formulated for administration as a single composition. In some embodiments, the agent that increases the level of epoxy-fatty acids and the additional agent(s) are formulated for separate administration, e.g., via the same or different route of administration. In varying embodiments, one or both the agent that increases the level of epoxy-fatty acids and the additional agent(s) are provided in unitary dosages in the kits.

EXAMPLES

The following examples are offered to illustrate, but not to limit the claimed invention.

Example 1

Gene Deficiency and Pharmacological Inhibition of Soluble Epoxide Hydrolase Confers Resilience to Repeated Social Defeat Stress: Role of BDNF-TrkB Signaling Materials and Methods Animals and animal care. Male adult C57BL/6 mice, aged 8 weeks (body weight 20-25 g, Japan SLC, Inc., Hamamatsu, Japan) and male adult CD1 (ICR) mice, aged 13-15 weeks (body weight >40 g, Japan SLC, Inc., Hamamatsu, Japan) were used for the social defeat stress model. A colony of sEH KO mice with targeted deletion of sEH gene (Ephx2) which is backcrossed to C57BL/6 background were used (57). Animals were housed under controlled temperatures and 12 hour light/dark cycles (lights on between 07:00-19:00 h), with ad libitum food (CE-2; CLEA Japan, Inc., Tokyo, Japan) and water. This study was carried out in strict accordance with the recommendations in the Guide for the Care and Use of Laboratory Animals of the National Institutes of Health. The protocol was approved by the Chiba University Institutional Animal Care and Use Committee.

Materials. The sEH inhibitor TPPU, 1-trifluoromethoxy-phenyl-3-(1-propionyl)piperidin-4-yl)urea, was synthesized in house as previously described (31). TPPU (0.3-3.0 mg/kg) was dissolved in 10% polyethylene glycol 400 (PEG400: Wako Pure Chemical Co., Tokyo, Japan). Other reagents were purchased commercially.

Effects of TPPU and 14,15-EET on neurite outgrowth. PC12 cells (RIKEN Cell Bank, Tsukuba, Japan) were cultured at 37° C., 5% $CO_2$ in Dulbecco's modified Eagle's medium (DMEM), supplemented with 5% heat-inactivated fetal bovine serum (FBS), 10% heat-inactivated horse serum, and 1% penicillin-streptomycin. Medium was changed two to three times a week. PC12 cells were plated onto 24-well tissue culture plates coated with poly-D-lysine/laminin. Cells were plated at relatively low density (0.25× $10^4$ cells/cm$^2$) in DMEM medium containing 0.5% FBS, 1% penicillin-streptomycin. Medium containing a minimal level of serum (0.5% FBS) was used as previously reported (58-60). In this study, 2.5 ng/ml of nerve growth factor (NGF: Alomone Labs Ltd., Jerusalem, Israel) was used to study the potentiating effects of TPPU and 14,15-EET on neurite outgrowth. Twenty-four hours after plating, the medium was replaced with DMEM medium containing 0.5% FBS and 1% penicillin-streptomycin with NGF (2.5 ng/ml), with or without TPPU (0.1, 1.0 or 10 µM), or 14,15-EET (0.01, 0.1 or 1.0 µM). Four days after incubation with NGF (2.5 ng/ml) with or without specified compounds, morphometric analysis was performed on digitized images of live cells taken under phase-contrast illumination, with an inverted microscope linked to a camera. Images of three fields per well were taken, with an average of 100 cells per field. Differentiated cells were counted by visual examination of the field; only cells that had at least one neurite with a length equal to the cell body diameter were counted, and were then expressed as a percentage of the total cells in the field. Counting was performed in a blinded manner.

Inflammation model of depression. The procedure of inflammation model of depression was performed as previously reported (36). Behavioral tests were performed 24 hours after a single administration of LPS (0.5 mg/kg). For experiment of cytokine level, TPPU (0.3, 1.0 or 3.0 mg/kg) was administered orally 60 min before LPS (0.5 mg/kg) administration. Serum sample was collected 90 min after LPS administration, and serum levels of TNF-α were measured using a Ready-SET-Go ELISA kit (eBioscience Inc., San Diego, Calif.), according to manufacturer's instructions. To examine the effect of a single dose of TPPU, vehicle or TPPU (3.0 mg/kg) was administered orally 23 hours after saline (10 ml/kg, IP) or LPS (0.5 mg/kg, IP) administration. Behavioral tests including locomotion (LMT), tail suspension test (TST), and forced swimming test (FST) were performed 1, 3, and 5 hours after administration. To examine the prophylactic effect of TPPU in the drinking water, mice were randomized to receive TPPU (15 mg/L) (33) in the drinking water or water alone for 3-weeks before saline (10 ml/kg, IP) or LPS (0.5 mg/kg, IP) administration. Behavioral tests including LMT, TST, and FST were performed 24, 26, and 28 hours after administration of LPS.

Social defeat stress model of depression. The procedure of social defeat stress was performed as previously reported (37,39,61,62). Every day the C57BL/6 mice were exposed to a different CD1 aggressor mouse for 10 min, total for 10 days. When the social defeat session ended, the resident CD1 mouse and the intruder mouse were housed in one half of the cage separated by a perforated Plexiglas divider to allow visual, olfactory, and auditory contact for the remainder of the 24-h period. At 24 h after the last session, all mice were housed individually. On day 11, a social avoidance test was performed to identify subgroups of mice that were susceptible and unsusceptible to social defeat stress. This was accomplished by placing mice in an interaction test box (42×42 cm) with an empty wire-mesh cage (10×4.5 cm) located at one end. The movement of the mice was tracked for 2.5 min, followed by 2.5 min in the presence of an unfamiliar aggressor confined in the wire-mesh cage. The duration of the subject's presence in the "interaction zone" (defined as the 8-cm-wide area surrounding the wiremesh cage) was recorded by a stopwatch. The interaction ratio was calculated as time spent in an interaction zone with an aggressor/time spent in an interaction zone without an aggressor. An interaction ratio of 1 was set as the cutoff: mice with scores <1 were defined as "susceptible" to social defeat stress and those with scores ≥1 were defined as "unsusceptible" (62). Only susceptible mice were used in the subsequent experiments.

Behavioral tests of antidepressant effects. Behavioral tests were performed as reported previously (36,37,39). Locomotion (LMT): the locomotor activity was measured by an animal movement analysis system SCANETMV-40 (MELQUEST Co., Ltd., Toyama, Japan), the mice were placed in experimental cages (length×width×height: 560×560×330 mm). The cumulative exercise was recorded for 60 minutes. Cages were cleaned between testing session.

Tail suspension test (TST): A small piece of adhesive tape placed approximately 2 cm from the tip of the tail for mouse. A single hole was punched in the tape and mice were hung individually, on a hook. The immobility time was recorded for 10 minutes. Mice were considered immobile only when they hung passively and completely motionless.

Forced swimming test (FST): The FST was tested by an automated forced-swim apparatus SCANETMV-40 (MELQUEST Co., Ltd., Toyama, Japan). The mice were placed individually in a cylinder (diameter: 23 cm; height: 31 cm) containing 15 cm of water, maintained at 23±1° C. Immobility time from activity time as (total)−(active) time was calculated by the apparatus analysis software. The immobility time for mouse was recorded for 6 minutes. TST and FST were also performed 2 and 4 hours after LMT, respectively Sucrose preference test (SPT): Mice were exposed to water and 1% sucrose solution for 24 h, followed by 4 hours of water and food deprivation and a 1 hour exposure to two identical bottles, one is water, and another is 1% sucrose solution. The bottles containing water and sucrose were weighed before and at the end of this period and the sucrose preference was determined.

Pharmacokinetic study of TPPU in mice. TPPU (3 mg/kg) was administered orally into adult mice. Blood and cerebral cortex were collected at 0.5, 1.0, 2.0, 4.0, 8.0 and 26 hours after a single oral administration of TPPU. Concentration of TPPU in the blood and cerebral cortex was determined using the previous method (35,63).

Enzyme activity in the brain samples. Enzyme activity of sEH in the brain samples was measured using the previous method (64). Brain regions including frontal cortex, hippocampus and striatum were resuspended in 1 mL of chilled buffer, sodium phosphate buffer (20 mM pH 7.4) containing 5 mM EDTA, 1 mM PMSF and 1 mM DTT, and then homogenized with Ultraturax (position 5.5 for 15-20 sec). The extract was centrifuged at 10,000 g for 20 min at 4° C. The supernatant was used for further analysis. The sEH activity: The supernatant was diluted in sodium phosphate buffer (0.1M pH 7.4) containing 0.1 mg/mL BSA. The reaction was started by adding 1 µL of [3H]-trans-diphenylpropene oxide (t-DPPO) to 100 µL of diluted extract ([S] final=50 µM). The reaction was carried at 37° C. The reaction was stopped by adding 60 µL of methanol, and extracted by either 200 µL of isooctane or 200 µL of hexanol. The formed diol was measured using liquid scintillation counter in water phase. Protein concentration was measured using BCA method with BSA as standard.

Oxylipin profiling. Measurement of eicosanoids was performed on brain samples from the control mice and chronically stressed (susceptible) mice by repeated social defeat stress. Concentration of eicosanoids in the frontal cortex, hippocampus and striatum was determined using the previous method (63,66).

Figure 9:
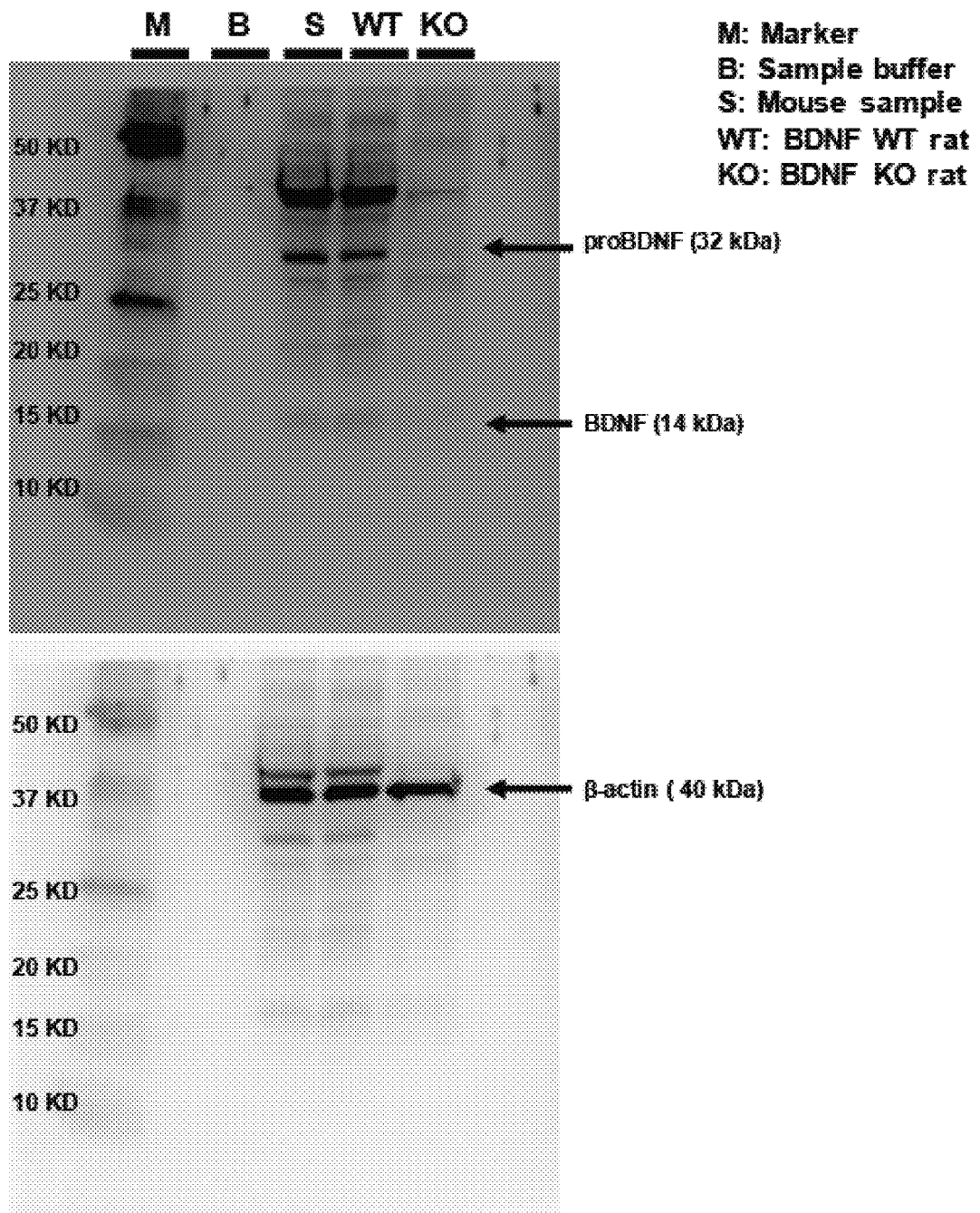
FIG. 9 illustrates Western blot analysis of proBDNF and BDNF (mature form) in the brain samples from BDNF KO rat, wild-type (WT) rat and mouse brain sample. The bands of proBDNF (ca. 32 KDa) and mature BDNF (ca, 14 KDa) were not detected in the brain samples from BDNF KO rat (SAGE Labo, Boyertown, Pa.). In this assay, the bands of β-actin were same.

Western blot analysis. To examine the selectivity of anti-BDNF (H-117; Santa Cruz Biotechnology, Inc., CA, USA) in the rat brain samples, we performed Western blot analysis of brain samples from WT and BDNF KO rats (SAGE Labs, Boyertown, Pa.). The bands for proBDNF and mature BDNF in the brain sample from BDNF KO rat were not detected (FIG. 9). Therefore, the anti-BDNF in this study could recognize both proBDNF and mature BDNF in mouse brain samples.

Western blot analysis was performed as reported previously (36,37,39,67). Mice were killed by cervical dislocation and brains were rapidly removed from the skull. Approximately 1-mm-thick coronal sections were cut and bilateral tissue punches of PFC, NAc, striatum (Str), CA1, CA3 and dentate gyms (DG) of the hippocampus were dissected on ice using a SZ-LED Kenis light microscope (Osaka, Japan), and stored at −80° C. Basically, tissue samples were homogenized in Laemmli lysis buffer. Aliquots (20 µg) of protein were measured using the DC protein assay kit (Bio-Rad, Hercules, Calif.), and incubated for 5 min at 95° C., with an equal volume of 125 mM Tris/HCl, pH 6.8, 20% glycerol, 0.1% bromophenol blue, 10% β-mercaptoethanol, 4% sodium dodecyl sulfate, and subjected to sodium dodecyl sulfate polyacrylamide gel electrophoresis, using AnyKD mini-gels (Mini-PROTEAN® TGX™ Precast Gel; Bio-Rad, Calif., USA). Proteins were transferred onto polyvinylidenedifluoride (PVDF) membranes using a Trans Blot Mini Cell (Bio-Rad). For immunodetection, the blots were blocked with 2% BSA in TBST (TBS+0.1% Tween-20) for 1 h at room temperature (RT), and kept with primary antibodies overnight at 4° C. The following primary antibodies were used: rabbit serum against mouse sEH (1:5000, prepared at UC Davis), BDNF (1:200, H-117, Cat #: sc-20981, Santa Cruz Biotechnology, Inc., CA, USA), phosphor-TrkB (Tyr 706) (1:200, Cat #: sc-135645, Santa Cruz Biotechnology, Inc., CA), TrkB (80E3) (1:1000, Cat #: 4603, Cell Signaling Technology, MA), AMPA glutamate receptor 1 (GluA1) (1 Abcam, Cambridge, Mass.), and postsynaptic density protein 95 (PSD-95) (1 μg/ml, Invitrogen, Carlsbad, Calif.). The next day, blots were washed three times in TBST and incubated with horseradish peroxidase conjugated anti-rabbit antibody (1:10000) 1 hour, at RT. After final three washes with TBST, bands were detected using enhanced chemiluminescence (ECL) plus the Western Blotting Detection system (GE Healthcare Bioscience). The blots then were washed three times in TBST and incubated with the primary antibody directed against β-actin (1:10000, Sigma-Aldrich Co, Ltd, St Louis, Mo.). Images were captured with a Fuji LAS3000-mini imaging system (Fujifilm, Tokyo, Japan), and immunoreactive bands were quantified.

Statistical analysis. The data show as the mean±standard error of the mean (S.E.M.). Analysis was performed using PASW Statistics 20 (formerly SPSS Statistics; SPSS). Comparisons between groups were performed using the one-way analysis of variance (ANOVA) or two-way ANOVA, followed by post-hoc Tukey tests. Comparisons between two groups were performed using Student t-test. The P-values of less than 0.05 were considered statistically significant.

Results

TPPU and 14,15-EET enhanced NGF-induced neurite outgrowth. Since antidepressants are known to affect the neuronal plasticity, we examined the effects of 1-trifluoromethoxyphenyl-3-(1-propionylpiperidine-4-yl)urea (TPPU: a potent sEH inhibitor)(31-33) and the endogenous eicosanoid 14,15-EET on nerve-growth factor (NGF)-induced neurite outgrowth in PC12 cells. Both TPPU and 14,15-EET potentiated NGF-induced neurite outgrowth in PC12 cells, in a concentration dependent manner (FIGS. 1A and 1B). The 14,15-EET was shown to enhance axonal growth neuronal cell cultures (34). These findings are consistent with the conclusion that TPPU and 14,15-EET can enhance neuronal plasticity, which is implicated in the action of antidepressants.

TPPU showed antidepressant effect in the inflammation-induced model of depression. First, we examined whether TPPU could attenuate an increase in serum levels of TNF-α in mice after lipopolysaccharide (LPS) administration. Oral administration of TPPU (0.3, 1.0 or 3.0 mg/kg, 60 min before) attenuated LPS (0.5 mg/kg)-induced increase of TNF-α levels, in a dose dependent manner (FIG. 2A). TPPU (3.0 mg/kg, PO) was no effect on serum levels of TNF-α in the control mice. Next, we examined whether TPPU showed antidepressant effects in mice pretreated with LPS (0.5 mg/kg). There were no differences in locomotion among the four groups (FIG. 2B). In the tail suspension test (TST) and forced swim test (FST), TPPU (3 mg/kg, PO) significantly reduced the increased immobility time in LPS-treated depressed mice. Furthermore, long-term intake of TPPU (15 mg/L for 3-weeks) as drinking water significantly prevented LPS (0.5 mg/kg, 24 hours)-induced depression-like behavior in mice although body weight was not different in the two groups (FIG. 2C). These data are consistent with the conclusion that oral administration of TPPU has therapeutic and prophylactic effects in the inflammation model of depression.

Pharmacokinetic study of TPPU in mice. Following single oral administration of TPPU (3 mg/kg), concentration of TPPU in the blood and brain increased rapidly. The average concentration of TPPU in the blood and brain 2 hours after oral administration was 4,240 ng/mL and 760 ng/g tissue, respectively. The half-life of TPPU in the plasma and cerebral cortex was 17.8 and 10.7 hours, respectively (FIGS. 3A and 3B). The pharmacokinetic data are consistent with the conclusion that TPPU can enter into the brain, consistent with a recent report (35).

TPPU showed antidepressant effect in the social defeat stress model. First, we examined the effects of TPPU pretreatment (3 mg/kg/day for 10 days, PO 60 min before each stress) on the depression-like behavior after repeated social defeat stress (FIG. 4A). In the social interaction test, TPPU-pretreated mice showed the increased social interaction time in the chronically stressed mice after social defeat stress compared with vehicle-treated mice (FIG. 4B). In the 1% sucrose preference test (SPT), TPPU-pretreated mice showed the increased sucrose preference compared with vehicle-treated mice (FIG. 4C). These findings are consistent with the conclusion that pretreatment with TPPU confers resilience to repeated social defeat stress.

Next, we examined the effects of TPPU treatment (3 mg/kg, PO) on the depression-like behavior in mice after repeated social defeat stress (FIG. 4D). In the social interaction test, susceptible mice were used as subsequent behavioral test (FIG. 4E). There were no differences in locomotion among the four groups (FIG. 4F). In the TST and FST, TPPU significantly reduced the increased immobility time in the mice after social defeat stress (FIGS. 4G and 4H). In the SPT, TPPU significantly increased the reduced preference in the mice after social defeat stress (FIG. 4I). In contrast, TPPU did not affect the sucrose preference in the control mice (FIG. 4I). These findings demonstrate that TPPU showed a rapid antidepressant effect in the social defeat stress model.

sEH KO mice showed resilience to repeated social defeat stress. Behavioral tests (locomotion (LMT), TST, FST, SPT) were first performed on the wild-type (WT), and the sEH knock-out (KO) mice (FIG. 5A). There were no differences in the all the behavioral tests among the two groups (FIG. 5B-5E). Next, the behavioral tests were performed after repeated social defeat stress (FIG. 5F). In the social interaction test, after social defeat stress, the social interaction time of KO mice was significantly higher than that of WT mice, and was similar to control no stressed mice (FIG. 5G). There were no differences in the LMT among the three groups (FIG. 5H). In the TST and FST, the immobility time of KO mice was significantly lower than that of WT mice after social defeat stress (FIGS. 5I and 5J). In the SPT, sucrose preference of KO mice was significantly higher and comparable to control animals than that of WT mice after social defeat stress (FIG. 5K). Overall, these data demonstrate that sEH KO mice show resilience to repeated social defeat stress.

Protein levels of sEH in the brain from mice with depression-like phenotype after LPS administration or social defeat stress. Previous reports demonstrated that prefrontal cortex (PFC), CA3, and dentate gyms (DG) of the hippocampus, striatum, and nucleus accumbens (NAc) play a role in the depression-like behaviors in rodents after inflammation, social defeat stress, and learned helplessness (36-40). We examined whether sEH protein is altered in the brain tissues from mice after LPS (0.5 mg/kg) administration (FIG. 6A) or repeated social defeat stress (FIG. 6B). We found significant increases of sEH protein in the PFC, striatum, CA1, CA3, and DG, but not the NAc, of both models of depression.

Increased levels of sEH protein in the brain of depressed patients. Using postmortem brain samples from Neuropathology Consortium of the Stanley Medical Research Institute (41) (Table 4), we examined whether sEH protein was also altered in the brain of patients suffering from depression, bipolar disorder, and schizophrenia. Protein levels of sEH in the parietal cortex (Brodmann area 7: BA7) from depression (N=15), bipolar disorder (N=15), and schizophrenia (N=15) were significantly higher than those of controls (N=15) (FIG. 6C). By contrast, protein levels of sEH in the cerebellum were not different among the four groups (FIG. 6D). These findings are consistent with the conclusion that increased levels of sEH in the parietal cortex is involved in the pathogenesis of these psychiatric disorders.

Figure 6E:
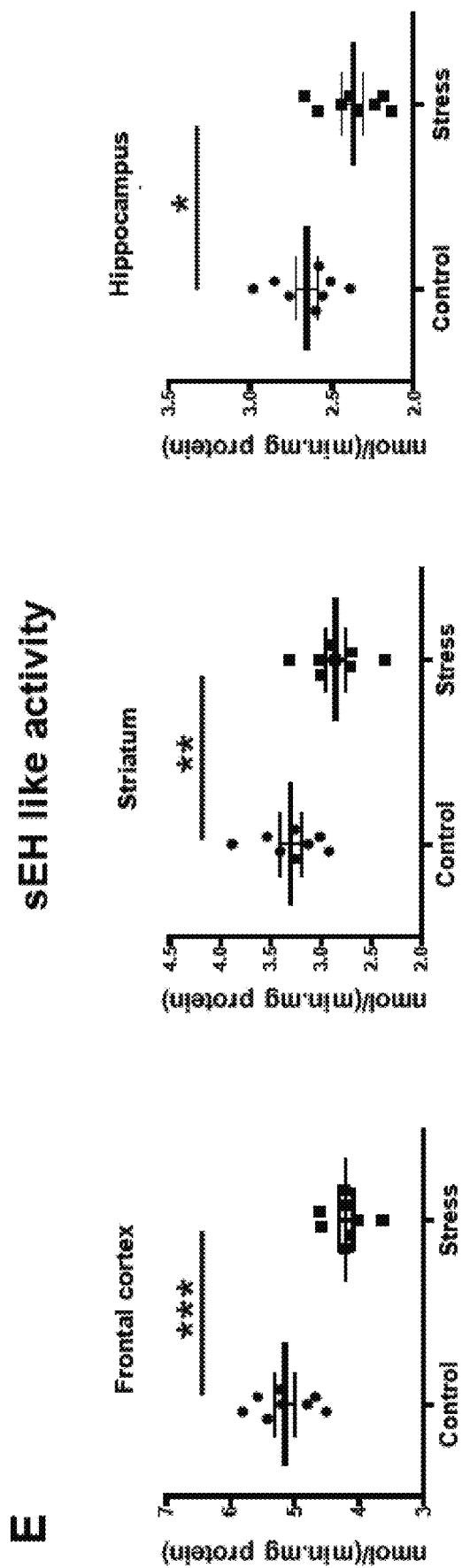

Enzyme activity of sEH and oxylipin profile of brain from mice with depression-like phenotype. Since the levels of sEH protein were increased in the brain samples from mice with depression-like behaviors, we examined whether enzyme activity of sEH and eicosanoids in the brain regions are altered in the brain from chronically stressed (susceptible) mice. Unexpectedly, enzyme activity of sEH in the frontal cortex, hippocampus and striatum from chronically stressed (susceptible) mice was significantly lower than that of control mice (FIG. 6E).

Figure 7:
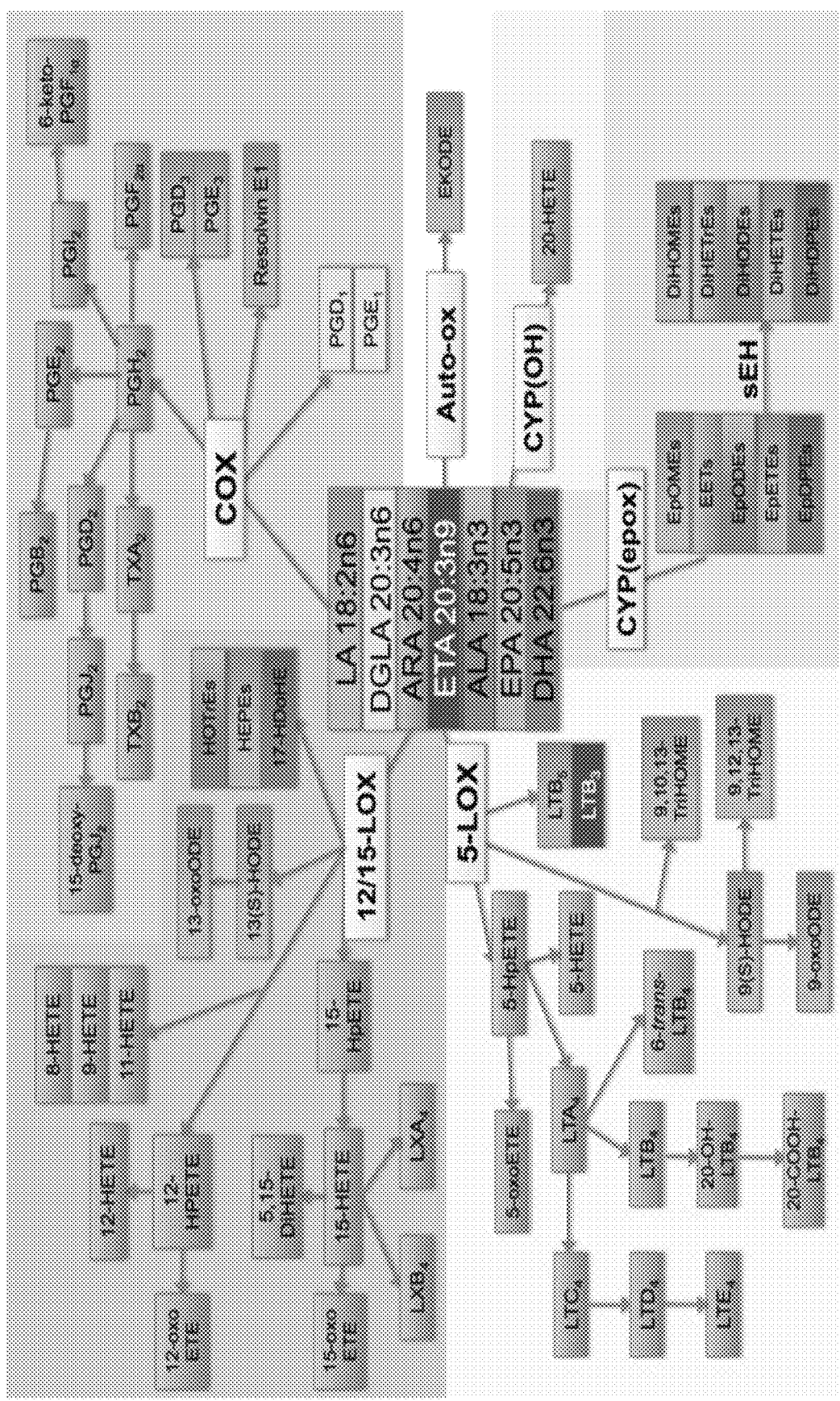
FIG. 7 illustrates eicosanoids measured in the brain regions from control and chronically stress (susceptible) mice.

Next we measured tissue levels of eicosanoids metabolites (FIG. 7) in the PFC, hippocampus and striatum from control and repeated social defeat stress (susceptible) mice. There were no changes for metabolites including EETs, and their metabolites dihydroxyeicosatrienoic acids (DHETs) in the prefrontal cortex (PFC), striatum and hippocampus (Tables 5-7).

TABLE 5-continued

Levels Of Eicosanoids Metabolites In The Prefrontal Cortex (PFC) From Control And Mice With Depression-Like Phenotype

|  | Control | Depression | P value |
| --- | --- | --- | --- |
| 13-HODE | 30.3 ± 4.4 | 24.3 ± 2.6 | 0.263 |
| 9-HODE | 21.9 ± 2.9 | 21.0± 2.1 | 0.791 |
| 15-HETE | 400.8 ± 165.0 | 384.5 ± 149.4 | 0.943 |
| 11-HETE | 322.5 ± 101.8 | 319.7 ± 112.5 | 0.986 |
| 8-HETE | 15.4 ± 6.8 | 12.3 ± 2.2 | 0.800 |
| 12-HETE | 26.9 ± 4.9 | 89.0 ± 26.9 | 0.040* |
| 15(S)-HETrE | 17.1 ± 8.5 | 16.9 ± 6.6 | 0.984 |
| 5-HETE | 21.0 ± 9.0 | 15.9 ± 5.5 | 0.636 |
| 19(20)-EpDPE | 78.4 ± 25.5 | 602.0 ± 434.1 | 0.249 |
| 12(13)-EpOME | 15.8 ± 5.3 | 101.5 ± 56.2 | 0.151 |
| 14(15)-EpETrE | 349.3 ± 88.8 | 1711.7 ± 981.4 | 0.188 |
| 9(10)-EpOME | 11.4 ± 4.6 | 82.4 ± 46.8 | 0.153 |
| 10(11)-EpDPE | 67.9 ± 21.1 | 247.5 ± 137.1 | 0.216 |
| 11(12)-EpETrE | 478.3 ± 132.0 | 2046.0 ± 1198.6 | 0.215 |
| 7(8)-EpDPE | 5730.9 ± 1755.5 | 22852.5 ± 12652.7 | 0.201 |
| 8(9)-EpETrE | 218.8 ± 59.4 | 944.2 ± 547.7 | 0.209 |
| 5(6)-EpETrE | 4031.3 ± 2321.3 | 47576.8 ± 29365.3 | 0.161 |

Student t-test:
*$P < 0.05$,
**$P < 0.01$.

TABLE 4

Characteristics Of The Postmortem Brain Tissues From Neuropathology Consortium Of The Stanley Medical Research Institute.

| Characteristics | Normal control (n = 15) | Bipolar disorder (n = 15) | Major depression (n = 15) | Schizophrenia (n = 15) | P value |
| --- | --- | --- | --- | --- | --- |
| Age at death (years) | 48.1 ± 10.7 (29-68) | 42.3 ± 11.7 (25-61) | 46.5 ± 9.3 (30-65) | 44.5 13.1 (25-62) | 0.540[a] |
| Gender (male/female) | 9/6 | 9/6 | 9/6 | 9/6 |  |
| PMI (hrs) | 23.7 ± 9.9 | 32.5 ± 16.1 | 27.5 ± 10.7 | 33.7 ± 14.6 | 0.147[a] |
| Brain pH | 6.27 ± 0.24 | 6.18 ± 0.23 | 6.18 ± 0.22 | 6.16 ± 0.26 | 0.616[a] |
| Brain hemispheres (right/left) | 7/8 | 8/7 | 6/9 | 6/9 | 0.864[b] |
| Brain weight (g) | 1501.0 ± 164.1 | 1441.2 ± 171.5 | 1462.0 ± 142.1 | 1471.7 ± 108.2 | 0.740[a] |
| Storage Days | 338.2 ± 234.3 | 620.5 ± 172.3 | 434.1 ± 290.0 | 621.1 ± 233.1 | 0.003[a] |
| Age of onset (years) |  | 21.5 ± 8.3 | 33.9 ± 13.3 | 23.2 ± 8.0 | 0.003[a] |
| Duration of disease (years) |  | 20.1 ± 9.7 | 12.7 ± 11.1 | 21.3 ± 11.4 | 0.068[a] |
| History of Psychosis |  | 11 with (4 without) |  | 15 (all) | 0.100[c] |
| Fluphenazine equivalent (mg) |  | 20827 ± 24016 (3 never) |  | 52267 ± 62062 (1 never) | 0.078[d] |

[a]One-way ANOVA,
[b]x2 test for independence,
[c]Fisher's exact probability test,
[d]Unpaired t-test.

TABLE 5

Levels Of Eicosanoids Metabolites In The Prefrontal Cortex (PFC) From Control And Mice With Depression-Like Phenotype

|  | Control | Depression | P value |
| --- | --- | --- | --- |
| 6-keto-PGF1a | 53.8 ± 8.9 | 55.7 ± 4.1 | 0.849 |
| TXB2 | 239.5 ± 17.9 | 312.2 ± 33.2 | 0.075 |
| 9,12,13-TriHOME | 14.7 ± 2.4 | 15.1 ± 3.0 | 0.932 |
| 9,10,13-TriHOME | 10.0 ± 2.2 | 10.6 ± 2.0 | 0.854 |
| PGF2a | 247.4 ± 24.6 | 326.2 ± 26.7 | 0.048* |
| PGE2 | 56.7 ± 6.7 | 83.3 ± 10.9 | 0.057 |
| PGD2 | 309.4 ± 31.8 | 344.3 ± 48.9 | 0.560 |
| PGJ2 | 23.7 ± 2.7 | 13.8 ± 1.5 | 0.006** |
| 12,13-DiHOME | 2.9 ± 0.7 | 1.4 ± 0.2 | 0.141 |
| 9,10-DiHOME | 2.5 ± 0.7 | 1.6 ± 0.2 | 0.237 |
| 11,12-DiHETrE | 0.6 ± 0.1 | 0.7 ± 0.1 | 0.919 |
| 15-deoxy-PGJ2 | 2.9 ± 0.4 | 1.5 ± 0.2 | 0.009** |
| 15-HEPE | 1.9 ± 0.8 | 4.0 ± 1.6 | 0.429 |
| 12-HEPE | 74.2 ± 38.3 | 287.4 ± 240.3 | 0.466 |

TABLE 6

Levels Of Eicosanoids Metabolites In The Striatum From Control And Mice With Depression-Like Phenotype

|  | Control | Depression | P value |
| --- | --- | --- | --- |
| 6-keto-PGF1a | 38.3 ± 5.1 | 72.7 ± 9.2 | 0.006** |
| TXB2 | 229.1 ± 32.5 | 325.9 ± 47.3 | 0.114 |
| 9,12,13-TriHOME | 23.5 ± 5.3 | 26.7 ± 4.8 | 0.656 |
| 9,10,13-TriHOME | 13.3 ± 3.3 | 23.1 ± 5.4 | 0.144 |
| PGF2a | 233.0 ± 36.0 | 320.2 ± 27.5 | 0.075 |
| PGE2 | 43.4 ± 10.5 | 46.4 ± 1.8 | 0.782 |
| PGD2 | 221.6 ± 33.5 | 236.7 ± 31.7 | 0.749 |
| PGJ2 | 13.6 ± 2.2 | 13.4 ± 1.3 | 0.951 |
| 12,13-DiHOME | 2.2 ± 1.1 | 3.5 ± 1.3 | 0.545 |
| 9,10-DiHOME | 2.5 ± 0.4 | 4.2 ± 1.1 | 0.156 |
| 11,12-DiHETrE | 1.2 ± 0.3 | 1.3 ± 0.1 | 0.714 |
| 15-deoxy-PGJ2 | 1.4 ± 0.3 | 1.3 ± 0.2 | 0.839 |
| 15-HEPE | 1.0 ± 0.4 | 11.7 ± 3.9 | 0.093 |
| 12-HEPE | 93.8 ± 43.7 | 123.2 ± 28.8 | 0.646 |

TABLE 6-continued

Levels Of Eicosanoids Metabolites In The Striatum From Control And Mice With Depression-Like Phenotype

|  | Control | Depression | P value |
|---|---|---|---|
| 13-HODE | 24.0 ± 1.8 | 32.2 ± 5.7 | 0.190 |
| 9-HODE | 21.0 ± 1.5 | 29.6 ± 4.8 | 0.110 |
| 15-HETE | 310.8 ± 81.2 | 418.5 ± 97.8 | 0.411 |
| 11-HETE | 272.6 ± 64.4 | 327 ± 85.9 | 0.620 |
| 8-HETE | 17.8 ± 8.1 | 7.5 ± 1.9 | 0.306 |
| 12-HETE | 56.0 ± 20.3 | 150.1 ± 108.2 | 0.407 |
| 15(S)-HETrE | 10.4 ± 3.9 | 14.8 ± 5.8 | 0.537 |
| 5-HETE | 14.0 ± 3.4 | 36.1 ± 13.8 | 0.144 |
| 19(20)-EpDPE | 141.5 ± 29.3 | 96.8 ± 35.5 | 0.370 |
| 12(13)-EpOME | 16.8 ± 3.9 | 32.7 ± 19.4 | 0.466 |
| 14(15)-EpETrE | 551.4 ± 95.9 | 518.8 ± 300.1 | 0.924 |
| 9(10)-EpOME | 21.0 ± 5.4 | 13.5 ± 5.3 | 0.357 |
| 10(11)-EpDPE | 101.4 ± 20.3 | 38.4 ± 12.7 | 0.023* |
| 11(12)-EpETrE | 647.4 ± 111.9 | 435.0 ± 187.2 | 0.372 |
| 7(8)-EpDPE | 10779.9 ± 2125.3 | 5171.9 ± 1978.1 | 0.084 |
| 8(9)-EpETrE | 286.5 ± 57.1 | 174.1 ± 62.5 | 0.224 |
| 5(6)-EpETrE | 7466.5 ± 1913.8 | 3279.7 ± 1522.0 | 0.119 |

Student t-test:
*P < 0.05,
**P < 0.01.

TABLE 7

Levels Of Eicosanoids Metabolites In The Hippocampus From Control And Mice With Depression-Like Phenotype

|  | Control | Depression | P value |
|---|---|---|---|
| 6-keto-PGF1a | 51.2 ± 3.3 | 77.9 ± 9.3 | 0.009** |
| TXB2 | 305.5 ± 31.5 | 357.7 ± 47.6 | 0.031* |
| 9,12,13-TriHOME | 28.0 ± 6.4 | 20.3 ± 1.6 | 0.706 |
| 9,10,13-TriHOME | 18.5 ± 4.7 | 15.3 ± 3.4 | 0.772 |
| PGF2a | 324.0 ± 33.7 | 405.7 ± 31.4 | 0.059 |
| PGE2 | 48.7 ± 3.6 | 69.5 ± 5.2 | 0.011* |
| PGD2 | 236.9 ± 28.4 | 291.5 ± 54.9 | 0.219 |
| PGJ2 | 17.0 ± 1.4 | 11.2 ± 1.1 | 0.544 |
| 12,13-DiHOME | 2.7 ± 0.6 | 1.5 ± 0.4 | 0.204 |
| 9,10-DiHOME | 2.9 ± 0.5 | 2.5 ± 0.5 | 0.875 |
| 11,12-DiHETrE | 0.9 ± 0.1 | 1.0 ± 0.1 | 0.301 |
| 15-deoxy-PGJ2 | 2.1 ± 0.3 | 1.2 ± 0.2 | 0.450 |
| 15-HEPE | 4.6 ± 1.4 | 7.9 ± 1.9 | 0.202 |
| 12-HEPE | 61.6 ± 7.5 | 113.4 ± 35.6 | 0.125 |
| 13-HODE | 38.8 ± 8.2 | 30.7 ± 4.9 | 0.59 |
| 9-HODE | 29.4 ± 6.2 | 25.1 ± 3.1 | 0.662 |
| 15-HETE | 289.0 ± 54.4 | 435.7 ± 94.2 | 0.104 |
| 11-HETE | 245.5 ± 39.5 | 456.5 ± 125.4 | 0.076 |
| 8-HETE | 7.3 ± 1.9 | 12.3 ± 2.8 | 0.228 |
| 12-HETE | 123.6 ± 95.6 | 104.3 ± 33.1 | 0.630 |
| 15(S)-HETrE | 6.4 ± 4.1 | 20.9 ± 5.5 | 0.011* |
| 5-HETE | 17.7 ± 5.2 | 24.9 ± 9.0 | 0.308 |
| 19(20)-EpDPE | 232.2 ± 82.3 | 177.9 ± 68.3 | 0.658 |
| 12(13)-EpOME | 33.0 ± 13.2 | 36.7 ± 12.5 | 0.928 |
| 14(15)-EpETrE | 957.0 ± 411.1 | 863.1 ± 339.4 | 0.679 |
| 9(10)-EpOME | 35.1 ± 15.3 | 23.0 ± 10.6 | 0.434 |
| 10(11)-EpDPE | 142.5 ± 63.9 | 86.1 ± 42.9 | 0.359 |
| 11(12)-EpETrE | 1477.3 ± 784.1 | 1161.9 ± 492.7 | 0.524 |
| 7(8)-EpDPE | 19478.4 ± 8391.2 | 10095.0 ± 4691.2 | 0.267 |
| 8(9)-EpETrE | 623.1 ± 286.6 | 425.6 ± 203.7 | 0.433 |
| 5(6)-EpETrE | 17414.8 ± 9708.9 | 14116.5 ± 8585.6 | 0.651 |

Student t-test:
*P < 0.05,
**P < 0.01.

Role of BDNF-TrkB signaling and synaptogenesis in the stress resilience of sEH KO mice. Since BDNF-TrkB signaling pathway play a key role in depression-like phenotype in rodents (25-30), we examined this signaling pathway in selected brain regions of sEH KO mice. Western blot analyses of BDNF, its precursor proBDNF, TrkB, and phosphorylated TrkB (p-TrkB) in the selected brain regions (PFC, NAc, striatum, DG, CA1 and CA3 of the hippocampus) in WT mice and sEH KO mice were performed. Levels of BDNF in the PFC, CA1, CA3, DG, but not NAc and striatum, of KO mice were significantly higher than those of WT mice (FIGS. 8A and 8D). In contrast, tissue levels of proBDNF in the all tested regions did not differ between the two groups (FIGS. 8B and 8D).

To clarify the role of TrkB phosphorylation in the stress resilience of sEH KO mice, we performed Western blot analyses of TrkB and p-TrkB, an activated form of TrkB, in samples from PFC, NAc, striatum, and hippocampus (CA1, CA3, DG). Tissue levels of TrkB in the all tested regions did not differ among the four groups (FIG. 8D). KO mice showed an increased ratio of p-TrkB/TrkB protein in the PFC, CA1, CA3 and DG, but not NAc and striatum (FIG. 8C). These findings are consistent with the conclusion that increased BDNF-TrkB signaling in PFC and hippocampus (CA1, CA3, DG) of KO mice is involved in the resilience to repeated social defeat stress.

Next, we performed Western blot analysis on the synaptogenesis markers, GluA1 (a subtype of AMPA receptor) and postsynaptic density protein 95 (PSD-95), in selected brain regions (FIG. 8E-8G). Levels of GluA1 and PSD-95 in the PFC, CA1, CA3, DG, but not NAc and striatum, of KO mice were significantly higher than those of WT mice (FIG. 8E-8G).

Discussion

Overall, our results demonstrate a key role of sEH in the pathogenesis of depression. The major findings of the present study are: First, a potent sEH inhibitor TPPU and 14,15-EET potentiated NGF-induced neurite outgrowth in PC12 cells, demonstrating that sEH inhibitors can enhance neuronal plasticity associated with depression. Second, TPPU showed prophylactic and therapeutic effects in the inflammation and social defeat stress models of depression. Third, protein levels of sEH in the brain from mice with depression-like behaviors or postmortem brain from depressed patients were higher than those of controls. Fourth, sEH KO mice show resilience to social defeat stress, and increased BDNF-TrkB signaling in the PFC and hippocampus of KO mice might be implicated in the stress resilience. These all findings are consistent with the conclusion that sEH inhibitors find use as therapeutic drugs for depression.

In this study, we found that a single dose of TPPU has a rapid antidepressant effect in both the inflammation and the repeated social defeat stress models of depression. Interestingly, current antidepressants (paroxetine and venlafaxine) do not have any effect in the LPS-induced inflammation model of depression (36). In addition, most current antidepressants can take weeks before patients or animal models feel the full antidepressant effects (42,43). Recently, we reported that a single dose of N-methyl-D-aspartate (NMDA) receptor antagonist ketamine (or R-ketamine) showed a rapid antidepressant effect in the social defeat stress model (37,39), consistent with rapid antidepressant effects of ketamine in treatment-resistant patients with depression (44-46). However, ketamine leads to psychotomimetic side effects and abuse liability that appears to be absent in the case of TPPU. These results demonstrate that sEH inhibitors have the ability to be more effective, faster acting, and have fewer side effects than current antidepressant drugs.

Tissue levels of sEH protein in the PFC, striatum and hippocampus of mice with depression-like behaviors were higher than those on control mice. Interestingly, we also found that levels of sEH in the parietal cortex from patients with major psychiatric disorders (depression, bipolar disorder and schizophrenia) were higher than controls. Inflammation is also implicated in these psychiatric disorders (6-10,47-50). Recent studies showed that peripheral interleukin-6 (IL-6) is critical in regulating stress-related depression-like phenotypes in rodents (51-53). Because sEH plays an active role in the inflammatory response (18-20), it is possible that increased levels of sEH protein in the parietal cortex may play a role in the pathogenesis of these psychiatric disorders. In contrast, the enzyme activity of sEH in these regions from mice with depression-like phenotype was lower than that of control mice. In addition, we found no changes in the eicosanoid metabolites such as EETs and their metabolites DHETs. Although the reasons underlying this discrepancy are currently unclear, it seems that compensatory response by increased levels of sEH protein in mice with depression-like phenotype may be involved.

Accumulating evidence are consistent with the conclusion that BDNF-TrkB signaling plays a key role in the depression-like phenotype in rodents (25-30). In this study, we found that BDNF protein in the PFC and hippocampus, but not NAc, of sEH KO mice was higher than that of WT mice, and that p-TrkB/TrkB ratio in the PFC and hippocampus of sEH KO mice was also higher than that of WT mice, indicating increased BDNF-TrkB signaling in the PFC and hippocampus in the sEH KO mice. Previously, we reported that inflammation, social defeat stress, and learned helplessness caused decreased BDNF-TrkB signaling in PFC and hippocampus, while increasing signals in the NAc, inducing depression-like behavior in rodents (36-40). Interestingly, we reported that regional differences in BDNF levels in PFC and hippocampus of rat brain may contribute to resilience to inescapable stress (38). A recent study demonstrated that 14,15-EET could promote the production of BDNF from astrocyte (54). Since sEH KO mice show a higher level of 14,15-EET, it is likely that increased level of 14,15-EET by sEH deletion might contribute to increased BDNF expression in the frontal cortex and hippocampus. Given the key role of BDNF-TrkB signaling in the depression-like phenotype, it is likely that increased BDNF-TrkB signaling in the PFC and hippocampus might be implicated in the stress resilience of sEH KO mice.

Many depressed patients become chronically ill, with several relapses (early return of symptoms within the expected duration of a current episode, of perhaps 3-12 months) or later recurrences (new episodes) following initial short-term improvement or remission (55,56). Recurrence rates are over 85% within a decade of an index depressive episode, and average approximately 50% or more within six months of apparent clinical emission (56). Therefore, the prevention of relapse and recurrence is very important in the management of depression. In this study, we found the prophylactic effects of TPPU in the inflammation and repeated social defeat stress models of depression, showing that TPPU prevents the onset of depression-like phenotype by inflammation or repeated social defeat stress. Therefore, sEH inhibitors find use as prophylactic and/or therapeutic drugs to prevent or minimize the relapse by inflammation and/or stress in the remission state of depressed patients.

In conclusion, our study shows that a single dose of the sEH inhibitor TPPU can produce a rapid antidepressant effect in the inflammation and social defeat stress models of depression. Furthermore, it is likely that increased BDNF-TrkB signaling in the PFC and the hippocampus in sEH KO mice may confer stress resilience. Finally, unlike to ketamine, sEH inhibitors operate as rapid antidepressants without psychotomimetic side effects and abuse liability.

REFERENCES

1. World Health Organization (WHO) Depression (2012) Fact sheet No. 369/October 2012. Available at http://www.who.int/mediacentre/factsheets/fs369/en/index.html.
2. Steinert C, Hofmann M, Kruse J, Leichsenring F (2014) Relapse rates after psychotherapy for depression—stable long-term effects? A meta-analysis. J Affect Disord 168: 107-118.
3. Biesheuvel-Leliefeld K E et al. (2015) Effectiveness of psychological interventions in preventing recurrence of depressive disorder: meta-analysis and meta-regression. J Affect Disord 174:400-410.
4. Guidi J, Tomba E, Fava G A (2015) The sequential integration of pharmacotherapy and psychotherapy in the treatment of major depressive disorder: A meta-analysis of the sequential model and a critical review of the literature. Am J Psychiatry 2015 Oct. 20, doi: 10.1176/appi.ajp.2015.15040476.
5. Dantzer R, O'Connor J C, Freund G G, Johnson R W, Kelly K W (2008) From inflammation to sickness and depression: when the immune system subjugates the brain. Nature Rev Neurosci 9(1):46-57.
6. Miller A H, Maletic V, Raison C L (2009) Inflammation and its discontents: The role of cytokines in the pathophysiology of major depression. Biol Psychiatry 65(9): 732-741.
7. Raison C L, Lowry C A, Rook G A (2010) Inflammation, sanitation, and consternation: loss of contact with coevolved, tolerogenic microorganisms and the pathophysiology and treatment of major depression. Arch Gen Psychiatry 67(12):1211-1224.
8. Hashimoto K (2015) Inflammatory biomarkers as differential predictors of antidepressant response. Int J Mol Sci 16(4):7796-7801.
9. Gold P W (2015) The organization of the stress system and its dysregulation in depressive illness. Mol Psychiatry 20(1): 32-47.
10. Dowlati Y, et al (2010) A meta-analysis of cytokines in major depression. Biol Psychiatry 67(5):446-457.
11. Young J J, Bruno D, Pomara N (2014) A review of the relationship between pro-inflammatory cytokines and major depressive disorder. J Affect Disord 169:15-20.
12. Haapakoski R, et al (2015) Cumulative meta-analysis of interleukins 6 and 1β, tumour necrosis factor α and C-reactive protein in patients with major depressive disorder. Brain Behav Immun 49:206-215.
13. Strawbridge R, et al (2015) Inflammation and clinical response to treatment in depression: A meta-analysis. Eur Neuropsychopharmacol 25(10):1532-1543.
14. Dean B, et al (2010) Regionally-specific changes in levels of tumour necrosis factor in the dorsolateral prefrontal cortex obtained postmortem from subjects with major depressive disorder. J Affect Disord 120(1-3):245-248.
15. Shelton R C, et al (2011) Altered expression of genes involved in inflammation and apoptosis in frontal cortex in major depression. Mol Psychiatry 16(7):751-762.
16. Na K S, Lee K J, Lee J S, Cho Y S, Jung H Y (2014) Efficacy of adjunctive celecoxib treatment for patients with major depressive disorder: a meta-analysis. Prog Neuropsychopharmacol Biol Psychiatry 48:79-85.

17. Köhler O, et al (2014) Effect of anti-inflammatory treatment on depression, depressive symptoms, and adverse effects: a systematic review and meta-analysis of randomized clinical trials. JAMA Psychiatry 71(12): 1381-1391.
18. Morisseau C, Hammock B D (2005) Epoxide hydrolases: mechanisms, inhibitor designs, and biological roles. Annu Rev Pharmacol Toxicol 45:311-333.
19. Imig J D, Hammock B D (2009) Soluble epoxide hydrolase as a therapeutic target for cardiovascular diseases. Nat Rev Drug Discov 8(10):794-805.
20. Morisseau C, Hammock B D (2013) Impact of soluble epoxide hydrolase and epoxyeicosanoids on human health. Annu Rev Pharmacol Toxicol 53:37-58.
21. Harris T R, Hammock B D (2013) Soluble epoxides hydrolase: gene structure, expression and deletion. Gene 526(2):61-74.
22. Wagner K, Vito S, Inceoglu B, Hammock B D (2014) The role of long chain fatty acids and their epoxide metabolites in nociceptive signaling. Prostaglandins Other Lipid Mediat 113-115:2-12.
23. López-Vicario C, et al (2015) Inhibition of soluble epoxide hydrolase modulates inflammation and autophagy in obese adipose tissue and liver: role for omega-3 epoxides. Proc Natl Acad Sci USA 112(2):536-541.
24. Shih P B, et al (2015) Dysregulation of soluble epoxide hydrolase and lipidomic profiles in anorexia nervosa. Mol Psychiatry 2015 Mar. 31. doi: 10.1038/mp.2015.26.
25. Nestler E J, et al. (2002) Neurobiology of depression. Neuron 34(1):13-25.
26. Hashimoto K, Shimizu E, Iyo M (2004) Critical role of brain-derived neurotrophic factor in mood disorders. Brain Res Brain Res Rev 45(2):104-114.
27. Duman R S, Monteggia L M (2006) A neutrotrophic model for stress-related mood disorders. Biol Psychiatry 59(12):1116-1127.
28. Hashimoto K (2010) Brain-derived neurotrophic factor as a biomarker for mood disorders: an historical overview and future directions. Psychiatry Clin Neurosci 64(4): 341-357.
29. Hashimoto K (2013) Sigma-1 receptor chaperone and brain-derived neurotrophic factor: emerging links between cardiovascular disease and depression. Prog Neurobiol 100:15-29.
30. Björkholm C, Monteggia L M (2015) BDNF-a key transducer of antidepressant effects. Neuropharmacology 2015 Oct. 28. doi: 10.1016/j.neuropharm.
31. Rose et al (2010) 1-Aryl-3-(1-acylpiperidin-4-yl)urea inhibitors of human and murine soluble epoxide hydrolase: structure-activity relationships, pharmacokinetics, and reduction of inflammatory pain. J Med Chem 53(19): 7067-7075.
32. Liu J Y, et al (2013) Substituted phenyl groups improve the pharmacokinetic profile and anti-inflammatory effect of urea-based soluble epoxide hydrolase inhibitors in murine models. Eur J Pharm Sci 48(4-5):619-627.
33. Sirish P, et al (2013) Unique mechanistic insights into the beneficial effects of soluble epoxide hydrolase inhibitors in the prevention of cardiac fibrosis. Proc Natl Acad Sci USA 110(4):5618-5623.
34. Abdu E, et al (2011) Epoxyeicosatrienoic acids enhance axonal growth in primary sensory and cortical neuronal cell cultures. J Neurochem 117(4): 632-642.
35. Ostermann A I, et al (2015) Oral treatment of rodents with soluble epoxide hydrolase inhibitor 1-trifluoromethoxyphenyl-3-(1-propionylpiperidin-4-yl)rea (TPPU): bioavailability, resulting drug levels and modulation of oxylipin pattern. Prostaglandins Other Lipid Mediat DOI: 10.1016/j.prostaglandins.2015.06.005.
36. Zhang J C, et al. (2015) Antidepressant effects of TrkB ligands on depression-like behavior and dendritic changes in mice after inflammation. Int J Neuropsychopharmacol 18(4):pyu077.
37. Zhang J C, et al (2015) Comparison of ketamine, 7,8-dihydroxyflavone, and ANA-12 antidepressant effects in the social defeat stress model of depression. Psychopharmacology (Berl) 232(23):4325-4335.
38. Yang C, Shirayama Y, Zhang J C, Ren Q, Hashimoto K (2015) Regional differences in brain-derived neurotrophic factor levels and dendritic spine density confer resilience to inescapable stress. Int J Neuropsychopharmacol 18(7): pyu121.
39. Yang C, et al (2015) R-ketamine: a rapid-onset and sustained antidepressant without psychotomimetic side effects. Transl Psychiatry 5:e632.
40. Shirayama Y, et al (2015) Alterations in brain-derived neurotrophic factor (BDNF) and its precursor proBDNF in the brain regions of a learned helplessness rat model and the antidepressant effects of a TrkB agonist and antagonist. Eur Neuropsychopharmacol doi: 10.1016/j.euroneuro.2015.09.002.
41. Torrey E F, Webster M, Knable M, Johnston N, Yolken R H (2000) The stanley foundation brain collection and neuropathology consortium. Schizophr Res 44(2):151-155.
42. Berton O, et al (2006) Essential role of BDNF in the mesolimbic dopamine pathway in social defeat stress. Science 311(5762):864-868.
43. Krishnan V, Nestler E J (2010) Linking molecules to mood: new insight into the biology of depression. Am J Psychiatry 167(11):1305-1320.
44. Krystal J H, Sanacora G, Duman R S (2013) Rapid-acting glutamatergic antidepressants: the path to ketamine and beyond. Biol Psychiatry 73(12):1133-1141.
45. Monteggia L M, Zarate C, Jr (2015) Antidepressant actions of ketamine: from molecular mechanisms to clinical practice. Curr Opin Neurobiol 30:139-143.
46. Newport D J, et al (2015) Ketamine and other NMDA antagonusts: early clinical trials and possible mechanisms in depression. Am J Psychiatry 172(10):950-956.
47. Munkholm K, Braüner J V, Kessing L V, Vinberg M (2013) Cytokines in bipolar disorder vs. healthy control subjects: a systematic review and meta-analysis. J Psychiatr Res 47(9):1119-1133.
48. Dargél A A, Godin O, Kapczinski F, Kupfer D J, Leboyer M (2015) C-reactive protein alterations in bipolar disorder: a meta-analysis. J Clin Psychiatry 76(2):142-150.
49. Potvin S, et al (2008) Inflammatory cytokine alterations in schizophrenia: a systematic quantitative review. Biol Psychiatry 63(8):801-808.
50. Fernandes B S, et al (2015) C-reactive protein is increased in schizophrenia but is not altered by antipsychotics: meta-analysis and implications. Mol Psychiatry 2015 Jun. 30. doi: 10.1038/mp.2015.86.
51. Hodes G E, et al (2014) Individual differences in the peripheral immune system promote resilience versus susceptibility to social stress. Proc Natl Acad Sci USA 111(45):16136-16141.
52. Yang C, Shirayama Y, Zhang J C, Ren Q, Hashimoto K (2015) Peripheral interleukin-6 promotes resilience versus susceptibility to inescapable electric stress. Acta Neuropsychiatr 27(5):312-316.

53. Yang C, Hashimoto K (2015) Peripheral IL-6 signaling: a promising therapeutic target for depression. Expert Opin Investig Drugs 24(7):989-990.
54. Yuan L, et al (2015) 14,15-epoxyeicosatrienoic acid promotes production of BDNF from astrocytes and exerts neuroprotective effects during ischemic injury. Neuropathol Appl Neurobiol 2015 Nov. 3. doi: 10.1111/nan.12291
55. Forte A, et al (2015) Long-term morbidity in bipolar-I, bipolar-II, and unipolar major depressive disorders. J Affect Disord 178:71-78.
56. Sim K, Lau W K, Sim J, Sum M Y, Baldessarini R J (2015) Prevention of relapse and recurrence in adults with major depressive disorder: systematic review and meta-analyses of controlled trials. Int J Neuropsychopharmacol 18:pyv076.
57. Sinai C J, et al (2000) Targeted disruption of soluble epoxide hydrolase reveals a role in blood pressure regulation. J Biol Chem 275(51):40504-40510.
58. Hashimoto K, Ishima T (2010) A novel target of action of minocycline in NGF-induced neurite outgrowth in PC12 cells: translation initiation factor eIF4AI. PLoS One 5(11):e15430.
59. Ishima T, Hashimoto K (2012) Potentiation of nerve growth factor-induced neurite outgrowth in PC12 cells by ifenprodil: the role of sigma-1 and IP3 receptors. PLoS One 7(5):e37989.
60. Golden S A, Covington H E III, Berton O, Russo S J (2011) A standard protocol for repeated social defeat stress in mice. Nat Protoc 6(8):1183-1191.
61. Zhao T, et al. (2013) Effects of chronic social defeat stress on behavior and choline acetyltransferase, 78-kDa glucose-regulated protein, and CCAAT/enhancer-binding protein (C/EBP) homologous protein in adult mice. Psychopharmacology (Berl) 228(2):217-230.
62. Inceoglu B, et al (2013) Epoxy fatty acids and inhibition of the soluble epoxide hydrolase selectively modulate GABA mediated neurotransmission to delay onset of seizures. PLoS One 8(12):e80922.
63. Yang J, Schmelzer K, Georgi K, Hammock B D (2009) Quantitative profiling method for oxylipin metabolome by liquid chromatography electrospray ionization tandem mass spectrometry. Anal Chem 81(19):8085-8093.
64. Borhan B, Mebrahtu T, Nazarian S, Kurth M J, Hammock B D (1995) Improved radiolabeled substrates for soluble epoxide hydrolase. Anal Biochem 231: 188-200.
65. Kitamura S, et al (2015) Potent natural soluble epoxide hydrolase inhibitors from Pentadiplandra brazzeana baillon: synthesis, quantification, and measurement of biological activities in vitro and in vivo. PloS One 10(2): e0117438.
66. Yang J, Schmelzer K, Georgi K, Hammock B D (2009) Quantitative profiling method for oxylipin metabolome by liquid chromatography electrospray ionization tandem mass spectrometry. Anal Chem 81(19):8085-8093.
67. Ren Q, et al (2015) BDNF-TrkB signaling in the nucleus accumbens shell of mice has key role in methamphetamine withdrawal symptoms. Transl Psychiatry 5:e666.

Example 2

Inhibition of Soluble Epoxide Hydrolase Reduces or Reverses Addictive Behaviors

Effects of TPPU on the Development of Behavioral Sensitization After Repeated Administration of Methamphetamine (METH)

Mice were divided into the following four groups: vehicle (10 ml/kg, p.o.)+saline (10 ml/kg, s.c.); vehicle (10 ml/kg, p.o.)+METH (Dainippon Pharmaceutical Ltd., Osaka, Japan, 3.0 mg/kg, s.c.); TPPU (10 mg/kg, p.o.)+METH (3.0 mg/kg, s.c.) and TPPU (10 mg/kg, p.o.)+vehicle (10 ml/kg, s.c.). The interval between the pretreatment injection and second injection was 60 minutes. After the administration of METH or saline, mice were returned to their home cages. This cycle of injections was performed on each mouse, for 5 consecutive days. Seven days after the final administration, all mice were given a low dose of METH (1.0 mg/kg, s.c.), and locomotor activity was measured using an animal movement analysis system (SCANET MV-40, Melquest, Toyama, Japan). The results are depicted in FIG. 9. The results show that TPPU prevented the development of behavioral sensitization in mice after repeated administration of methamphetamine.

Role of sEH on the Development of Behavioral Sensitization After Repeated Administration of Methamphetamine (METH)

Figure 10:
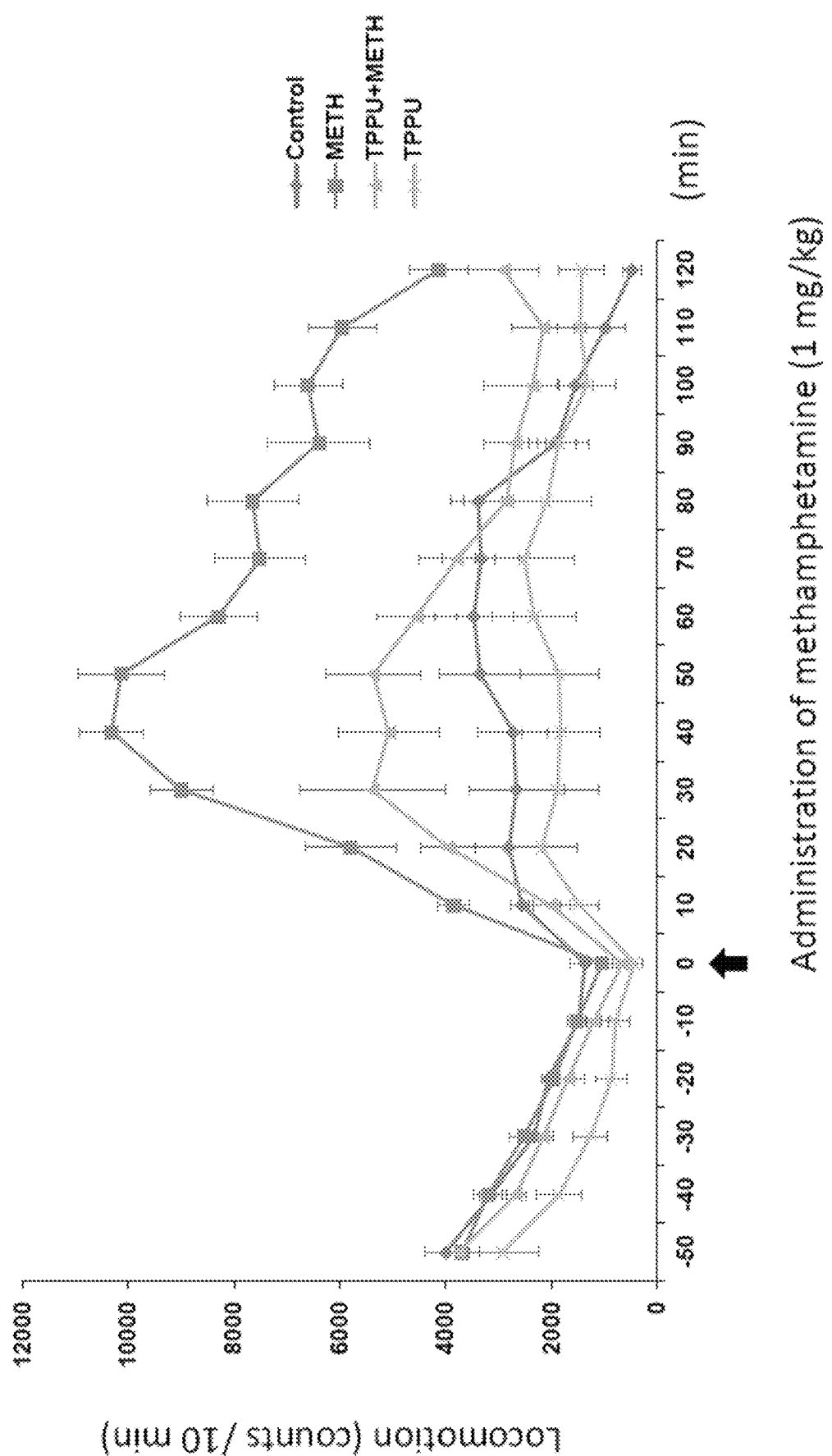
FIG. 10 illustrates that TPPU prevented the development of behavioral sensitization in mice after repeated administration of methamphetamine.
Figure 11:
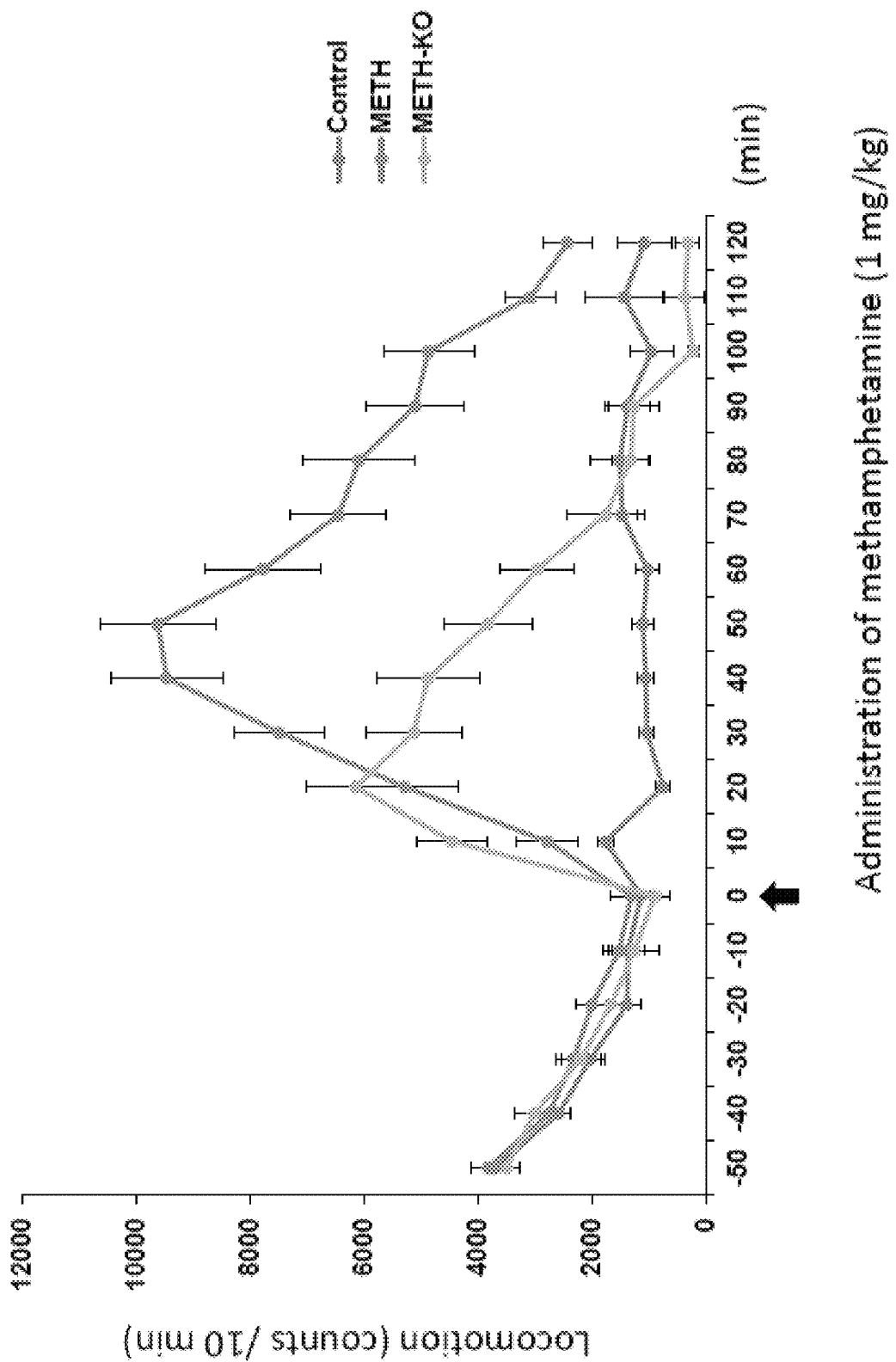
FIG. 11 illustrates that the development of behavioral sensitization in sEH KO mice after repeated administration of methamphetamine was weaker than wild-type mice.

Wild-type and sEH mice were divided into the following two groups (saline or METH (3 mg/kg/day for 5 days), respectively. Saline (10 ml/kg/day, s.c.) or METH (Dainippon Pharmaceutical Ltd., Osaka, Japan, 3.0 mg/kg/day, s.c.) were administered for consecutive 5 days. After the administration of METH or saline, mice were returned to their home cages. Seven days after the final administration, all mice were given a low dose of METH (1.0 mg/kg, s.c.), and locomotor activity was measured using an animal movement analysis system (SCANET MV-40, Melquest, Toyama, Japan). The results are depicted in FIG. 10. The results show that the development of behavioral sensitization in sEH KO mice after repeated administration of methamphetamine was weaker than wild-type mice.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of reducing, ameliorating, mitigating, and/or inhibiting depression in a subject in need thereof, comprising administering to the subject a compound having the formula

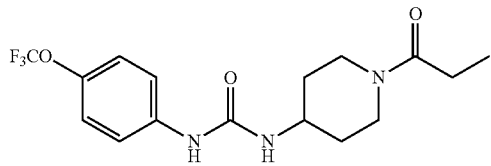 [SMILES: CCC(=O)N1CCC(NC(=O)Nc2ccc(OC(F)(F)F)cc2)CC1]

1-trifluoromethoxyphenyl-3-(1-propionylpiperidin-4-yl) urea (TPPU; compound 1770) or

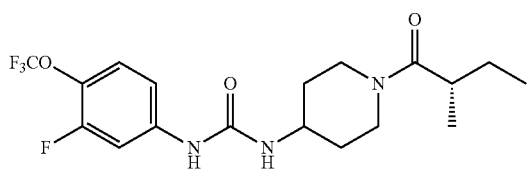 [SMILES: CC[C@H](C)C(=O)N1CCC(NC(=O)Nc2ccc(OC(F)(F)F)c(F)c2)CC1]

(S)-1-(3-fluoro-4-(trifluoromethoxy)phenyl)-3-(1-(2-methylbutanoyl)piperidin-4-yl)urea or a pharmaceutically acceptable salt thereof.

2. The method of claim 1, wherein the subject is administered a compound having the formula

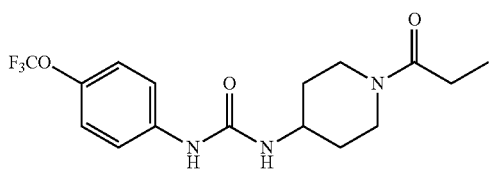 [SMILES: CCC(=O)N1CCC(NC(=O)Nc2ccc(OC(F)(F)F)cc2)CC1]

1-trifluoromethoxyphenyl-3-(1-propionylpiperidin-4-yl) urea (TPPU; compound 1770) or a pharmaceutically acceptable salt thereof.

3. The method of claim 1, wherein the subject is administered a compound having the formula

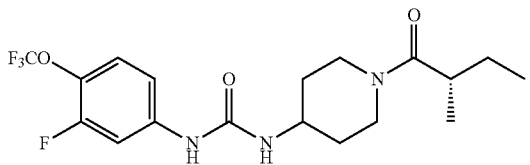 [SMILES: CC[C@H](C)C(=O)N1CCC(NC(=O)Nc2ccc(OC(F)(F)F)c(F)c2)CC1]

(S)-1-(3-fluoro-4-(trifluoromethoxy)phenyl)-3-(1-(2-methylbutanoyl)piperidin-4-yl)urea or a pharmaceutically acceptable salt thereof.

4. A method of accelerating responsiveness to pharmacological treatment and/or reducing, ameliorating, mitigating, inhibiting, delaying recurrence and/or relapse of depression in a subject in need thereof, comprising administering to the subject an agent that increases the level of epoxy-fatty acids, or a functional derivative or mimic thereof, as sole active agent or co-administered with a second agent, wherein the agent that increases the level of epoxy-fatty acids, or a functional derivative or mimic thereof is a compound having the formula

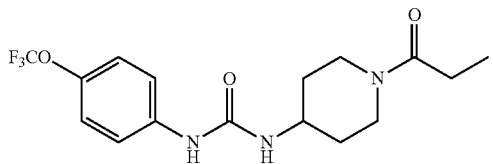 [SMILES: CCC(=O)N1CCC(NC(=O)Nc2ccc(OC(F)(F)F)cc2)CC1]

1-trifluoromethoxyphenyl-3-(1-propionylpiperidin-4-yl) urea (TPPU; compound 1770) or

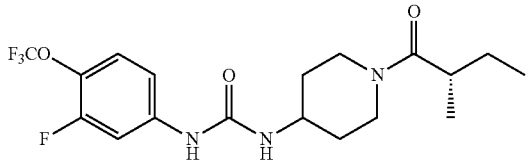 [SMILES: CC[C@H](C)C(=O)N1CCC(NC(=O)Nc2ccc(OC(F)(F)F)c(F)c2)CC1]

(S)-1-(3-fluoro-4-(trifluoromethoxy)phenyl)-3-(1-(2-methylbutanoyl)piperidin-4-yl)urea or a pharmaceutically acceptable salt thereof.

5. The method of claim 4, wherein one or both of the agent that increases the level of epoxy-fatty acids and the second agent are administered at a subtherapeutic or therapeutically ineffective dose.

6. The method of claim 4 wherein the second agent is an antidepressant, a mood stabilizer, an antipsychotic drug or an anxiolytic.

7. The method of claim 6, wherein the mood stabilizer is selected from the group consisting of lithium carbonate, divalproex sodium, valproic acid, valproate semisodium, sodium valproate, tiagabine, levetiracetam, lamotrigine, gabapentin, carbamazepine, oxcarbazepine, topiramate, zonisamide, aripiprazole, risperidone, olanzapine, quetiapine, asenapine, paliperidone, ziprasidone, lurasidone, verapamil, clonidine, propranolol, mexiletine, guanfacine and omega-3 fatty acids.

8. The method of claim 6, wherein the antipsychotic is selected from the group consisting of a butyrophenone, a diphenylbutylpiperidine, a phenothiazine, a thioxanthene, or is an atypical antipsychotic agent.

9. The method of claim 6, wherein the antipsychotic is selected from the group consisting of benperidol, bromperidol, droperidol, haloperidol, moperone, pipamperone, timiperone, fluspirilene, penfluridol, pimozide, phenothiazines, acepromazine, chlorpromazine, cyamemazine, dixyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, thioxanthenes, chlorprothixene, clopenthixol, flupentixol, thiothixene, zuclopenthixol, clotiapine, loxapine, prothipendyl, carpipramine, clocapramine, molindone, mosapramine, sulpiride, sultopride, veralipride, amisulpride, amoxapine, aripiprazole, asenapine, cariprazine, clozapine, blonanserin, iloperidone, lurasidone, melperone, nemonapride, olanzapine, paliperidone, perospirone, quetiapine, remoxipride, risperidone, sertindole, sultopride, trimipramine, ziprasidone, zotepine, brexpiprazole, ITI-007, pimavanserin and RP5063.

10. The method of claim 6, wherein the anxiolytic drug is selected from the group consisting of a barbiturate, a benzodiazepine and a beta-blocker.

11. The method of claim 6, wherein the anxiolytic drug is selected from the group consisting of alprazolam, bromazepam, chlordiazepoxide, clonazepam, clorazepate, diazepam, flurazepam, lorazepam, oxazepam, temazepam, triazolam, tofisopam, clonidine, guanfacine, mebicar, fabomotizole, selank, bromantane, emoxypine, buspirone, tandospirone, hydroxyzine, pregabalin, menthyl isovalerate, cannabidiol (cbd), tetrahydrocannabinol, *Garcinia indica* (kokum), *Scutellaria lateriflora*, *Coriandrum sativum* (coriander), *Salvia elegans* (pineapple sage), picamilon, chlorpheniramine, diphenhydramine, melatonin and myo-inositol.

12. The method of claim 6, wherein the antidepressant is selected from the group consisting of a selective serotonin reuptake inhibitor (SSRI), a serotonin-norepinephrine reuptake inhibitor (SNRI), a tricyclic or tetracyclic antidepressant (TCA), a monoamine oxidase inhibitor (MAOI) and an atypical antidepressant.

13. The method of claim 12, wherein the selective serotonin reuptake inhibitor (SSRI) is selected from the group consisting of citalopram, escitalopram, fluoxetine, fluvoxamine, fluvoxamine CR, paroxetine, paroxetine CR, and sertraline.

14. The method of claim 12, wherein the serotonin-norepinephrine reuptake inhibitor (SNRI) is selected from the group consisting of desvenlafaxine, duloxetine, venlafaxine, venlafaxine XR, milnacipran, and levomilnacipran.

15. The method of claim 12, wherein the tricyclic or tetracyclic antidepressant (TCA) is selected from the group consisting of amitriptyline, amoxapine, desipramine, doxepin, imipramine, nortriptyline, protriptyline, trimipramine and maprotiline.

16. The method of claim 12, wherein the monoamine oxidase inhibitor (MAOI) is selected from the group consisting of as selegiline, moclobemide, tranylcypromine, isocarboxazid and phenylzine.

\* \* \* \* \*